(12) United States Patent
Gangaikondan-Iyer et al.

(10) Patent No.: US 12,387,827 B2
(45) Date of Patent: Aug. 12, 2025

(54) COMPUTERIZED AGGREGATION AND TRANSACTION PROCESSING ARCHITECTURE FOR DIGITAL HEALTH INFRASTRUCTURE

(71) Applicant: Express Scripts Strategic Development, Inc., St. Louis, MO (US)

(72) Inventors: Harry S. Gangaikondan-Iyer, Morris Plains, NJ (US); Mark G. Bini, O'Fallon, MO (US); Zachary A. Goodman, St. Louis, MO (US); Sara A. Raj, St. Louis, MO (US); William S. Patterson, St. Louis, MO (US); Damian Ng, Creve Coeur, MO (US); Daniel C. Casper, Ellisville, MO (US); Ashley M. Jenne, St. Louis, MO (US); Sarah E. Ham, Olivette, MO (US); Jamie Williams, Edwardsville, IL (US); Christina M. Vallery, Austin, TX (US); Sarah Micheletti, St. Louis, MO (US); Glen D. Stettin, St. Louis, MO (US); Snezana Mahon, Creve Coeur, MO (US); Selva Prabhu, Parsippany, NJ (US); Shahnawaz A. Khan, Austin, TX (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 615 days.

(21) Appl. No.: 17/496,945

(22) Filed: Oct. 8, 2021

(65) Prior Publication Data
US 2022/0028513 A1    Jan. 27, 2022

Related U.S. Application Data

(63) Continuation-in-part of application No. 16/875,681, filed on May 15, 2020, now Pat. No. 12,148,014.
(Continued)

(51) Int. Cl.
*G16H 20/10* (2018.01)
*G06F 9/54* (2006.01)
(Continued)

(52) U.S. Cl.
CPC .............. *G16H 20/10* (2018.01); *G06F 9/547* (2013.01); *G06Q 20/405* (2013.01); *G06Q 30/04* (2013.01); *G06Q 40/08* (2013.01)

(58) Field of Classification Search
CPC .......... G16H 20/10; G06F 9/547; G06F 9/54; G06Q 20/405; G06Q 30/04; G06Q 40/08; G06Q 20/40
See application file for complete search history.

(56) References Cited

U.S. PATENT DOCUMENTS

| | | | | | |
|---|---|---|---|---|---|
| 6,068,156 | A | * | 5/2000 | Liff | G06V 20/66 |
| | | | | | 221/129 |
| 7,467,093 | B1 | * | 12/2008 | Newton | G07F 17/0092 |
| | | | | | 705/2 |

(Continued)

FOREIGN PATENT DOCUMENTS

| | | | | | |
|---|---|---|---|---|---|
| CA | 2655490 | A1 | * | 1/2008 | ........... G06Q 10/087 |
| CN | 102792261 | A | * | 11/2012 | .............. G07F 11/00 |

(Continued)

OTHER PUBLICATIONS

JP-2005059984, "Part Inspection System For Part Inspection System, and Part Inspection Method," 2005. (Year: 2005).*

*Primary Examiner* — Kenneth Bartley
(74) *Attorney, Agent, or Firm* — Miller Johnson

(57) ABSTRACT

A digital health solution system includes: a virtual pharmacy comprising one or more processors configured to operate a web portal for user devices via a network, the web portal serving as a marketplace for products and services available from vendors for consumption by users; a transaction processing module configured to: receive, via a network, a transaction from a vendor regarding one or more of the products and services consumed by one or more users via the virtual pharmacy for payment to the vendor; adjudicate the transaction using adjudication rules stored in memory; bill (Continued)

an entity for the use of the one or more of the products and services associated with the one or more users when the adjudication of the transaction passes; and transmit, via a network, a response regarding the transaction to the vendor.

21 Claims, 28 Drawing Sheets

Related U.S. Application Data

(60) Provisional application No. 62/848,543, filed on May 15, 2019.

(51) Int. Cl.
  *G06Q 20/40* (2012.01)
  *G06Q 30/04* (2012.01)
  *G06Q 40/08* (2012.01)

(56) References Cited

U.S. PATENT DOCUMENTS

| | | | | |
|---|---|---|---|---|
| 7,509,288 | B2* | 3/2009 | Bennett | G06Q 20/102 705/40 |
| 8,639,629 | B1* | 1/2014 | Hoffman | G06Q 20/3821 705/64 |
| 9,721,231 | B2 | 8/2017 | Ruszala | |
| 9,734,287 | B2 | 8/2017 | Linn | |
| 10,115,087 | B2 | 10/2018 | Pourfallah | |
| 10,152,761 | B2 | 12/2018 | Kress | |
| 10,346,587 | B2* | 7/2019 | Stamper | G16H 40/67 |
| 10,410,451 | B1* | 9/2019 | Khalil | G16H 10/65 |
| 10,484,376 | B1 | 11/2019 | Laucius | |
| 10,521,778 | B2 | 12/2019 | Bull | |
| 10,540,640 | B1 | 1/2020 | James | |
| 10,547,594 | B2 | 1/2020 | Chang | |
| 10,678,615 | B1* | 6/2020 | Creighton | G06F 9/543 |
| 10,751,254 | B2* | 8/2020 | Joplin | B65B 5/105 |
| 11,348,668 | B2 | 5/2022 | Atreja | |
| 11,538,113 | B1* | 12/2022 | Kessel | G16H 15/00 |
| 11,593,393 | B1* | 2/2023 | Allor | G06Q 40/08 |
| 2002/0002495 | A1 | 1/2002 | Ullman | |
| 2002/0032582 | A1* | 3/2002 | Feeney, Jr. | G07F 17/0092 700/231 |
| 2002/0194081 | A1* | 12/2002 | Perkowski | G06F 16/9554 705/26.1 |
| 2005/0022205 | A1* | 1/2005 | Green | G06F 9/465 719/310 |
| 2006/0020783 | A1* | 1/2006 | Fisher | G06Q 20/367 713/156 |
| 2006/0293927 | A1* | 12/2006 | Tummalapally | G06Q 40/08 705/2 |
| 2007/0027718 | A1* | 2/2007 | Amerantes | G16H 70/00 705/3 |
| 2007/0150480 | A1* | 6/2007 | Hwang | G06Q 50/60 |
| 2007/0168228 | A1* | 7/2007 | Lawless | G06Q 40/08 600/300 |
| 2008/0312957 | A1* | 12/2008 | Luciano, Jr. | G07F 17/0092 705/2 |
| 2009/0259493 | A1 | 10/2009 | Venon | |
| 2009/0307028 | A1* | 12/2009 | Eldon | G06Q 20/4016 705/37 |
| 2010/0031233 | A1* | 2/2010 | Li | G06F 9/541 717/106 |
| 2011/0258004 | A1* | 10/2011 | Dean | G06Q 10/10 705/4 |
| 2011/0295614 | A1* | 12/2011 | Hummer | G06Q 20/102 705/40 |
| 2012/0239560 | A1 | 9/2012 | Pourfallah | |
| 2012/0253829 | A1 | 10/2012 | John | |
| 2012/0265545 | A1* | 10/2012 | Hwang | G16H 20/30 705/1.1 |
| 2012/0265546 | A1* | 10/2012 | Hwang | G16H 20/40 705/2 |
| 2012/0265547 | A1* | 10/2012 | Hwang | G06Q 30/0207 705/2 |
| 2012/0265591 | A1* | 10/2012 | Hwang | G06Q 30/00 705/14.1 |
| 2013/0066650 | A1 | 3/2013 | Ackerman | |
| 2013/0166321 | A1 | 6/2013 | Harrell | |
| 2013/0204638 | A1 | 8/2013 | Matan | |
| 2014/0081652 | A1* | 3/2014 | Klindworth | G06Q 10/0635 705/2 |
| 2014/0089836 | A1 | 3/2014 | Damani | |
| 2014/0244296 | A1 | 8/2014 | Linn | |
| 2014/0278513 | A1 | 9/2014 | Prakash | |
| 2014/0379361 | A1 | 12/2014 | Mahadkar | |
| 2015/0012283 | A1 | 1/2015 | Ryan | |
| 2015/0052009 | A1 | 2/2015 | Ketchell, III | |
| 2015/0100328 | A1 | 4/2015 | Kress | |
| 2015/0104770 | A1 | 4/2015 | Agger | |
| 2015/0112703 | A1 | 4/2015 | Sysko | |
| 2015/0193750 | A1 | 7/2015 | Ivanoff | |
| 2015/0193872 | A1 | 7/2015 | Ivanoff | |
| 2015/0302154 | A1 | 10/2015 | Brooks | |
| 2016/0012194 | A1 | 1/2016 | Prakash | |
| 2016/0012465 | A1* | 1/2016 | Sharp | G06Q 20/321 705/14.17 |
| 2016/0019354 | A1* | 1/2016 | Grant | G16Z 99/00 705/2 |
| 2016/0034668 | A1* | 2/2016 | Rourke | G16H 10/60 705/2 |
| 2016/0042146 | A1 | 2/2016 | Douglass | |
| 2016/0253731 | A1* | 9/2016 | Ketchel, III | G06Q 20/065 705/26.5 |
| 2016/0321406 | A1* | 11/2016 | Timmerman | G06Q 10/10 |
| 2016/0321410 | A1 | 11/2016 | Timmerman | |
| 2016/0351070 | A1 | 12/2016 | Aillon-Sohl | |
| 2017/0039324 | A1 | 2/2017 | Francois | |
| 2017/0147775 | A1 | 5/2017 | Ohnemus | |
| 2017/0161771 | A1 | 6/2017 | Key | |
| 2017/0213269 | A1 | 7/2017 | Setlur | |
| 2017/0220768 | A1* | 8/2017 | Tanner, Jr. | G16H 20/13 |
| 2017/0220782 | A1 | 8/2017 | Alsanousi | |
| 2017/0351840 | A1 | 12/2017 | Goguen | |
| 2018/0075430 | A1* | 3/2018 | Suzuki | G06Q 20/047 |
| 2018/0082029 | A1 | 3/2018 | Bureau | |
| 2018/0108438 | A1 | 4/2018 | Ryan | |
| 2018/0137247 | A1 | 5/2018 | Bore | |
| 2018/0221244 | A1* | 8/2018 | Joplin | B65B 61/20 |
| 2018/0330418 | A1 | 11/2018 | Glasgow | |
| 2018/0342007 | A1 | 11/2018 | Brannigan | |
| 2018/0344215 | A1 | 12/2018 | Ohnemus | |
| 2018/0350451 | A1 | 12/2018 | Ohnemus | |
| 2019/0006037 | A1* | 1/2019 | Jacobs | G16H 20/13 |
| 2019/0026781 | A1* | 1/2019 | Beck | G06Q 20/3224 |
| 2019/0051388 | A1 | 2/2019 | Atreja | |
| 2019/0058697 | A1 | 2/2019 | Chang | |
| 2019/0065970 | A1 | 2/2019 | Bonutti | |
| 2019/0156475 | A1* | 5/2019 | Markson | G06T 7/70 |
| 2019/0214116 | A1 | 7/2019 | Eberting | |
| 2019/0214120 | A1* | 7/2019 | Hoffman | G06Q 10/087 |
| 2019/0304021 | A1 | 10/2019 | Rutherford | |
| 2019/0349261 | A1 | 11/2019 | Smith | |
| 2019/0355036 | A1 | 11/2019 | Ketchel, III | |
| 2019/0367275 | A1* | 12/2019 | Hoffman | B65G 1/1373 |
| 2019/0371463 | A1 | 12/2019 | Asthana | |
| 2019/0374436 | A1 | 12/2019 | Townley | |
| 2020/0013050 | A1 | 1/2020 | Finlow-Bates | |
| 2020/0043070 | A1 | 2/2020 | Ketchel, III | |
| 2020/0118127 | A1 | 4/2020 | Miller | |
| 2020/0160956 | A1 | 5/2020 | Roth | |
| 2020/0185100 | A1 | 6/2020 | Francois | |
| 2020/0257578 | A1* | 8/2020 | Creighton | G06F 9/542 |
| 2020/0315531 | A1 | 10/2020 | Cooper | |
| 2020/0372993 | A1 | 11/2020 | Chu | |
| 2020/0387887 | A1* | 12/2020 | Rathod | G06Q 20/3224 |
| 2022/0007965 | A1 | 1/2022 | Tiron | |
| 2022/0157433 | A1* | 5/2022 | Wu | G06N 20/00 |
| 2022/0246299 | A1 | 8/2022 | Gilvert | |
| 2022/0301664 | A1* | 9/2022 | Belingon | G16H 10/60 |
| 2022/0351842 | A1* | 11/2022 | Zheng | G16H 50/20 |
| 2022/0383325 | A1* | 12/2022 | Hoffman | G06Q 20/4018 |

(56) References Cited

U.S. PATENT DOCUMENTS

| | | | |
|---|---|---|---|
| 2023/0049853 A1* | 2/2023 | Boppana | G16H 40/63 |
| 2023/0050921 A1* | 2/2023 | Boppana | G06N 20/00 |
| 2023/0061020 A1* | 3/2023 | Kim | G06F 3/0482 |
| 2023/0093336 A1* | 3/2023 | Nath | G16H 50/80 |
| | | | 705/2 |
| 2023/0153837 A1* | 5/2023 | Seamster | G16H 10/60 |
| | | | 705/7.29 |
| 2023/0153914 A1* | 5/2023 | Pinsonneault | G06Q 10/10 |
| | | | 705/3 |
| 2023/0238092 A1* | 7/2023 | Rottkamp | G16H 20/00 |
| | | | 705/3 |

FOREIGN PATENT DOCUMENTS

| | | | | |
|---|---|---|---|---|
| EP | 2203908 B1 * | 11/2016 | | B65C 9/44 |
| EP | 36061231 A | 2/2020 | | |
| IN | 201741013738 | 10/2018 | | |
| JP | 2005059984 A * | 3/2005 | | |
| JP | 2019526120 A | 9/2019 | | |
| RU | 2725294 C1 | 6/2020 | | |
| TW | 201810151 A | 3/2018 | | |
| WO | 2016208901 A1 | 12/2016 | | |
| WO | 2018126075 A1 | 7/2018 | | |
| WO | 2018162687 A1 | 9/2018 | | |
| WO | WO-2018234882 A1 * | 12/2018 | | |
| WO | 2019036019 A1 | 2/2019 | | |
| WO | 2019079890 A1 | 5/2019 | | |
| WO | 2019222904 A1 | 11/2019 | | |

\* cited by examiner

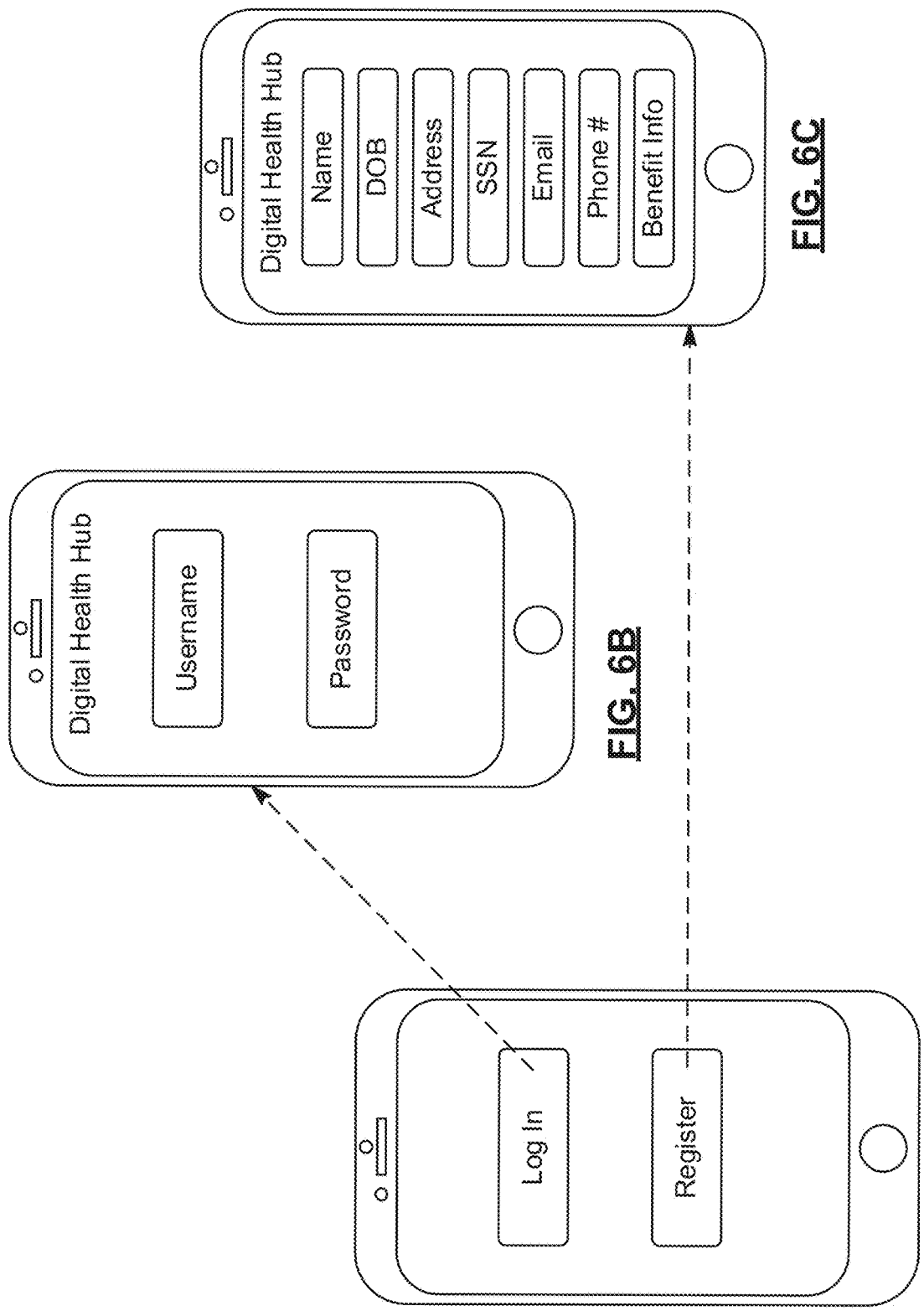

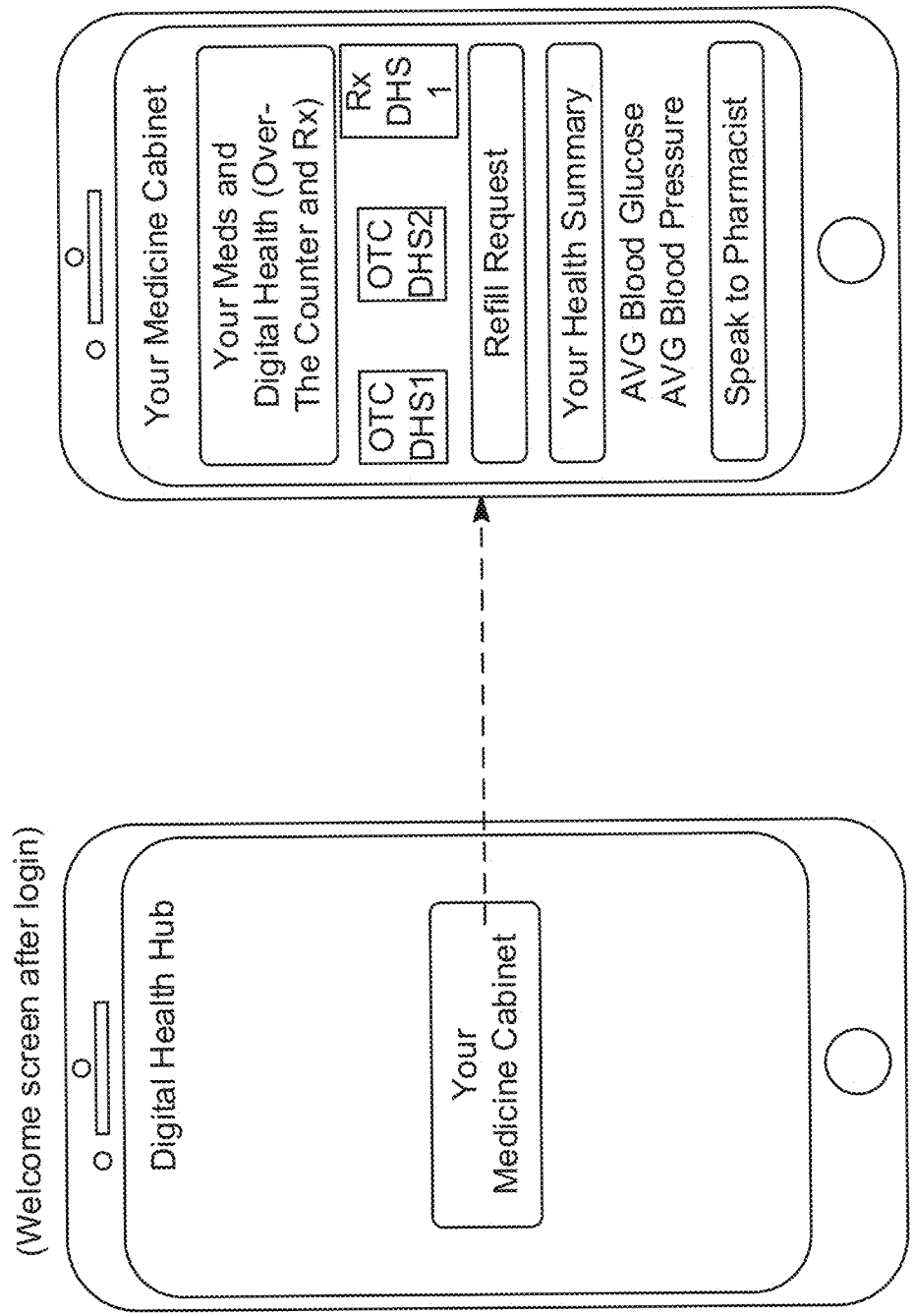

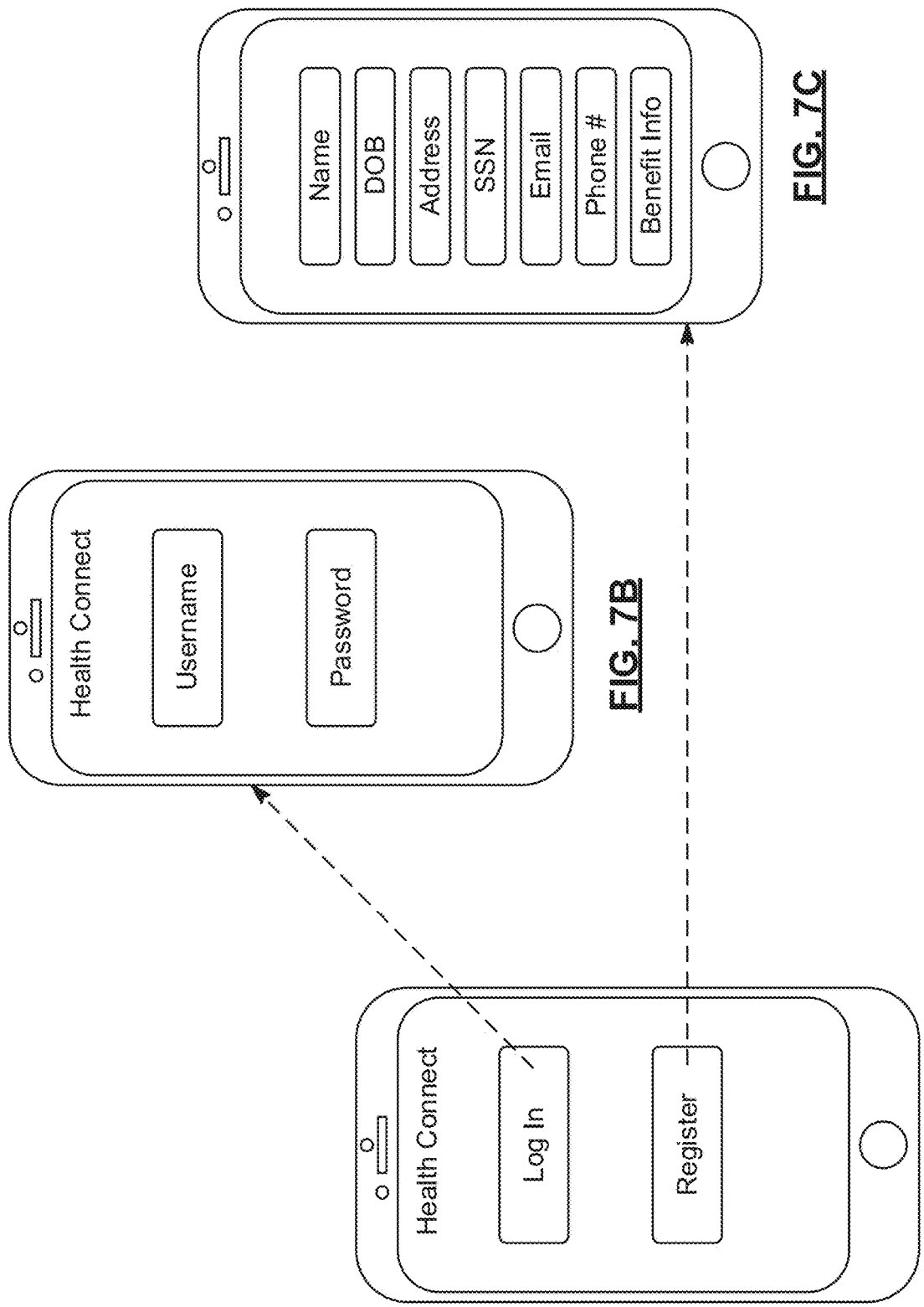

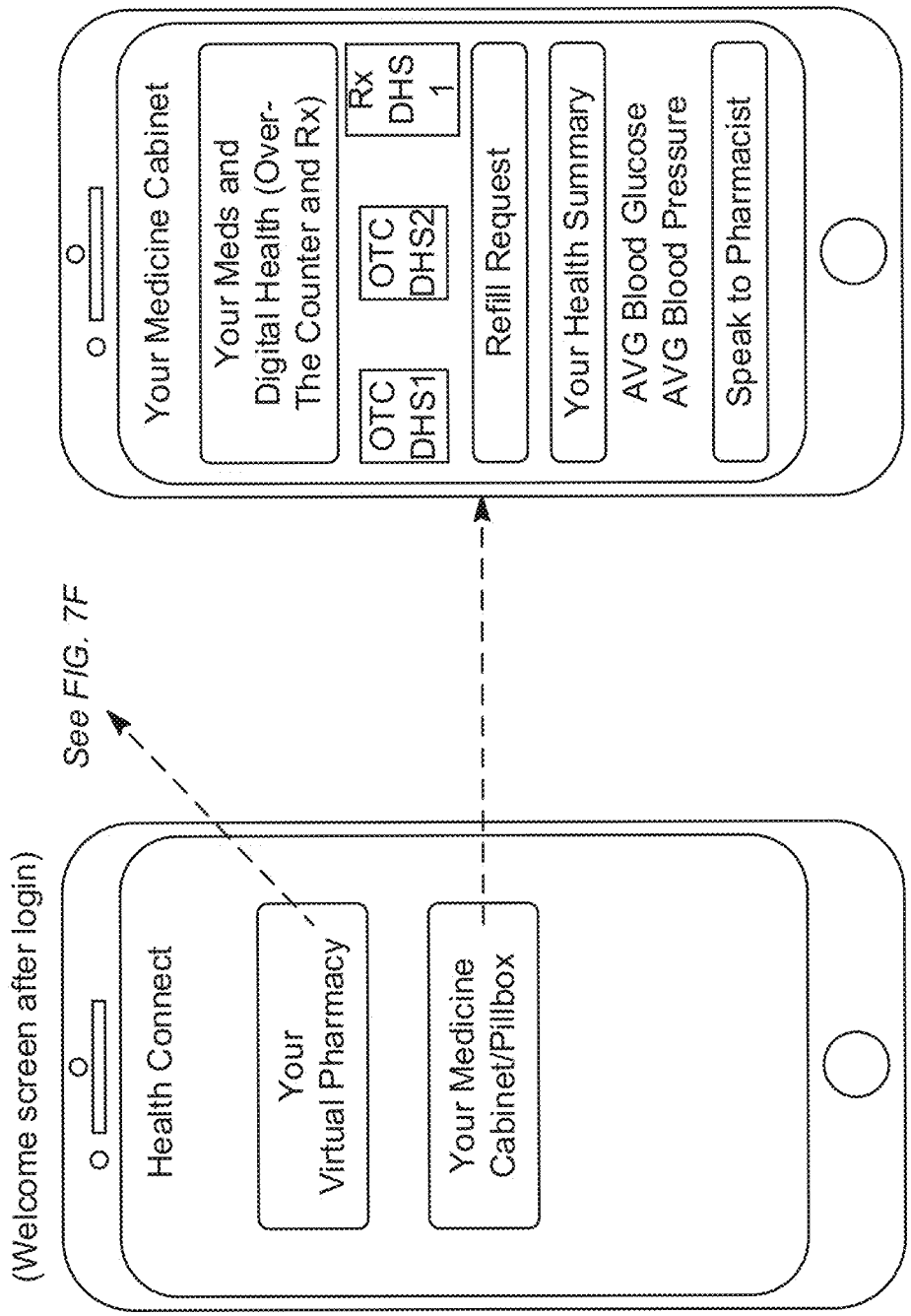

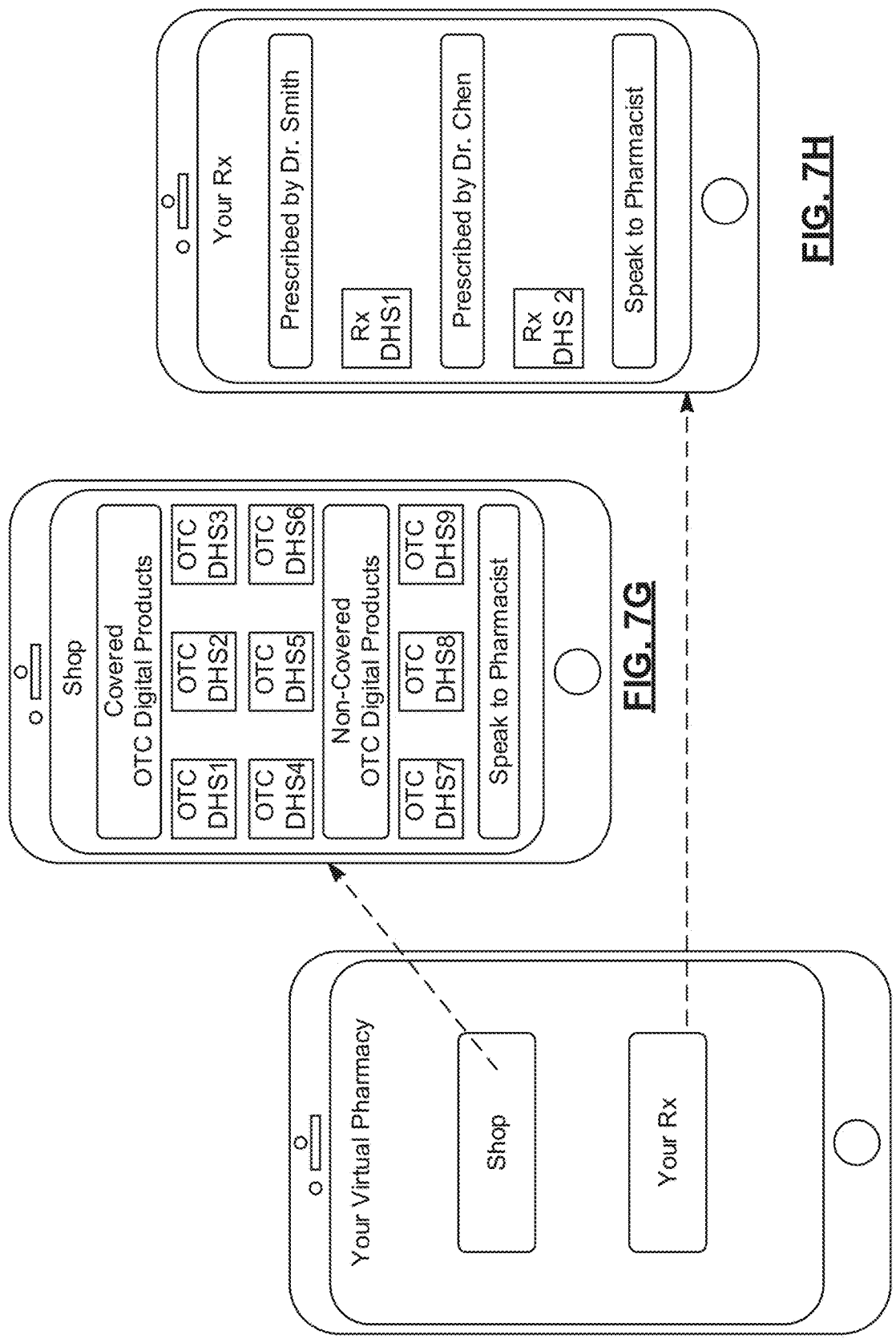

| Health Kit | Google Fit | Samsung Health | Fitbit |
|---|---|---|---|
| Apple Health Kit | Google Fit | Samsung Health | |
| Native iOS Health App That Consolidates Data From Your iPhone, Apple Watch, and Third-Party Apps | Native Android Health-Tracking Platform That Blends Data from Multiple Apps and Devices. | A Free App That Tracks Various Things Such as Physical Activity, Diet, and Sleep. | |
| Connect Apple Health Kit | Connect Google Fit | Connect Samsung Health | |
| Apple Watch | Samsung Galaxy Watch | Polar Watch | OURA |
| Apple Watch | Samsung Galaxy Watch | Polar Watch | |
| Connect Your Apple Watch to Sync Your Activity Data. | Connect Your Samsung Galaxy Watch to Sync Your Activity Data. | Connect Your Polar Watch to Sync Your Activity Data. | |
| Connect Your Apple Watch | Connect Your Samsung Galaxy Watch | Connect Your Polar Watch | |
| Other Wearables | Sleep Number | Eight sleep | |
| | Sleep Number 360 Smart Bed | Eight Sleep Smart Bed | |
| Connect Your Health Devices & Share Daily Health Matrix so we can Serve You Better | Connect Your 360 Smart Bed to Sync Your Sleep Data. | Connect Your Eight Sleep Smart Bed to Sync Your Sleep Data. | |
| Connect Your Devices | Connect Your 360 Smart Bed | Connect Your Eight Sleep Smart Bed | |
| Samsung Family Hub | Smart Fridges | | |
| Samsung Family Hub Smart Fridge | Other Smart Fridges | | |
| Connect Your Smart Fridge to Sync Your Eating Data. | Connect Your Smart Fridge so we can Serve You Better. | | |
| Connect Your Samsung Family Hub | Connect Your Smart Fridge | | |

FIG. 9

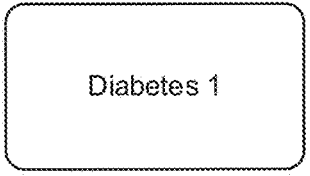

Diabetes 1

OneTouch Diabetes
Remote Monitoring

Insulin Delivery, at any Time
From up to 10 Feet Away
With OneTouch™

View System

Diabetes 2

Livongo Diabetes Insight

Using Personalized Health
Insights to Treat Diabetes
and Hypertension

View Tool

Sleep

Sleep Program

A Digital Sleep-Improvement
Program Featuring Cognitive
Behavioral Therapy
(CBT)Techniques.

Improve Sleep

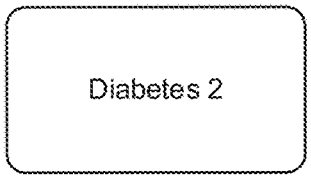

Therapeutic Resource
Centers

Therapy Management
Program for Treating These
Rare Complex Diseases

Sign Up

Therapease Cuisine

Nutritional Services Program
for Those Diagnosed With
Cancer.

Sign Up

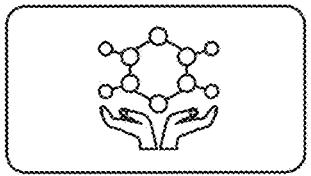

Community Resources

Connect With People Who
Share Similar Health
Condition as Yours.

Explore Communities

Health Tools

Connect Your Health Devices &
Share Daily Health Matrix so we
can Serve You Better Connect Your Devices

FIG. 11

```
HDR20210212115615202001012021021testvendorid4 VENDOR4
DTL1671 FTLVCDH7 D000000000010000000872958500119750401201904014000000 013345678900001
DTL1671 FTLVCDH7 D000000000010000000872958500119750401201904024000000 013345678900001
DTL1671 FTLVCDH7 D000000000010000000872958500119750401201904034000000 013345678900001
TRL000000003
```

FIG. 21A

KIERRA DABROWSKI 0212660691001753122 2020-03-10-16.26.39.656565PATIENTID001
KIERRA DABROWSKI 0212660691001753122 2020-03-10-16.26.39.656565PATIENTID001
KIERRA DABROWSKI 0212660691001753122 2020-03-10-16.26.39.656565PATIENTID001

FIG. 21B

```
{
  "dhfMemTransactionId":
  "header": {
    "date":
    "time":
    "vendorFileId":
    "vendorFileName":
    "dhfVendorFileId":
    "vendorId":
    "vendorName":
  },
  "transaction": {
    "carrierId":
    "eligGroup":
    "paymentType":
    "unitCount":
    "memberid":
    "personNum":
    "dob":
    "activationCode":
    "upcQual":
    "upc":
    "firstName":
    "lastName":
    "patientAgn":
    "contract":
    "claimId":
    "dateOfService":
    "recordNumber":
    "vendMemTimestamp":
    "vendPatientId":
  }
}
```

FIG. 22

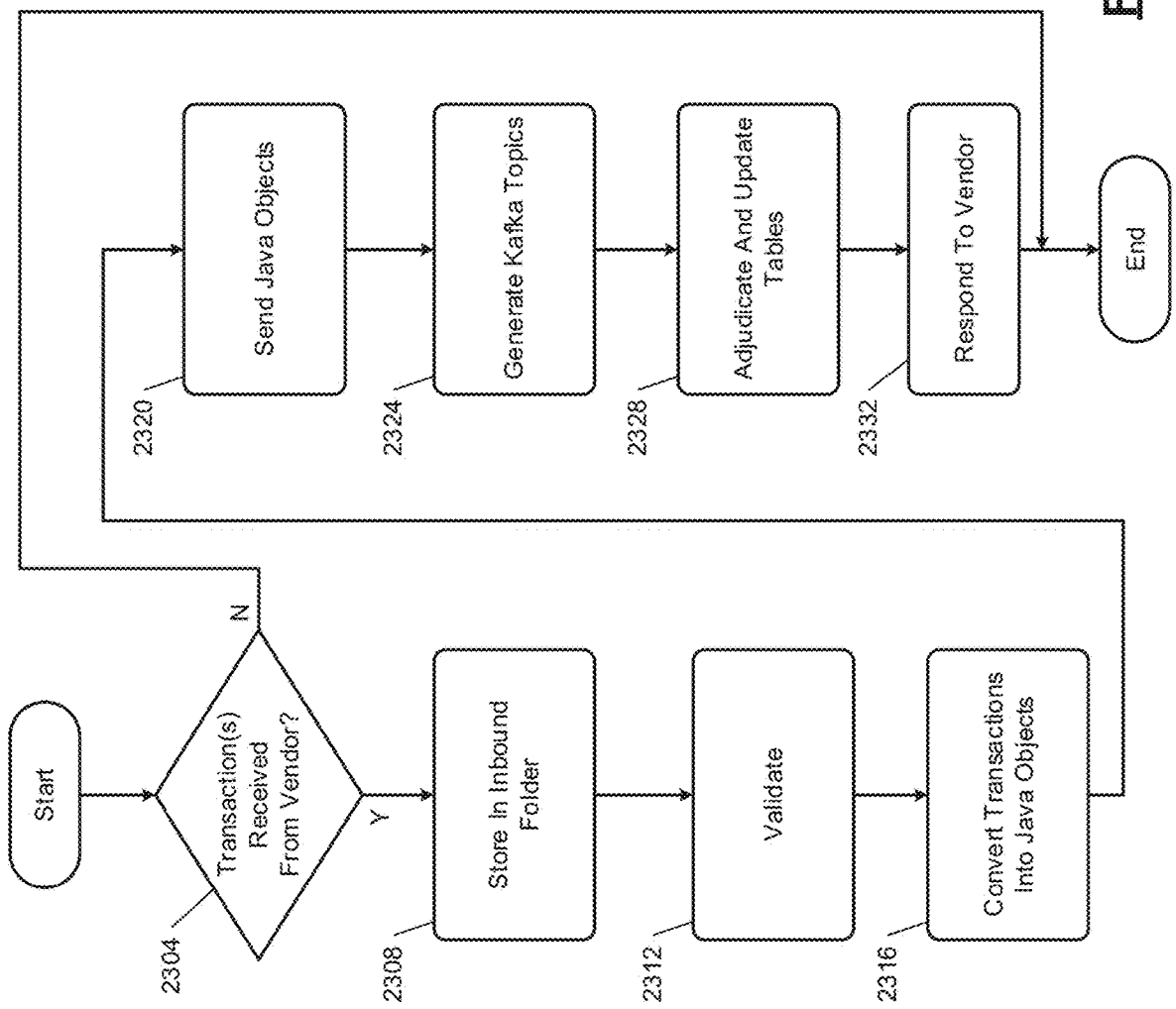

COMPUTERIZED AGGREGATION AND TRANSACTION PROCESSING ARCHITECTURE FOR DIGITAL HEALTH INFRASTRUCTURE

CROSS-REFERENCE TO RELATED APPLICATIONS

This application is a continuation-in-part application of U.S. patent application Ser. No. 16/875,681, filed on May 15, 2020, which claims the benefit of U.S. Provisional Application No. 62/848,543, filed May 15, 2019. The entire disclosures of the applications referenced above are incorporated by reference.

FIELD

The present disclosure relates to computerized health interventions and therapeutics and more particularly to distribution and transaction processing platforms for computerized health interventions and therapeutics.

BACKGROUND

Therapies for patients may take the form of medications, such as pills, whether prescribed by a clinician or obtained by the patient over-the-counter. Recently, digital therapies and digital interventions have become available to supplement the effectiveness of and adherence to medications, to gather medical data, and to treat patients directly.

In fact, there are by some estimates over 318,000 health-related applications (apps) available currently. This makes evaluating the safety and efficacy of apps by interested parties, such as pharmacy benefit managers, very difficult and makes it nearly impossible for an individual patient to identify the best app or apps for their needs.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a feature, a digital health solution system is described. A virtual pharmacy includes one or more processors configured to operate a web portal for user devices via a network, the web portal serving as a marketplace for products and services available from vendors for consumption by users. A transaction processing module is configured to: receive, via a network and a first application programming interface (API), a batch of transactions from a first vendor regarding one or more of the products and services consumed by users via the virtual pharmacy for payment to the first vendor, each of the transactions of the batch of transactions having a first data structure; receive, via a network and a second API, a single transaction from a second vendor regarding one of the products and services consumed by a single user via the virtual pharmacy for payment to the second vendor, the single transaction having a second data structure that is different than the first data structure; adjudicate the batch of transactions and the single transaction using adjudication rules stored in memory; bill a first entity for the use of the one or more of the products and services associated with the one or more users when the adjudication of transactions of the batch of transactions passes; deny one of the transactions of the batch of transactions when the one of the transactions of the batch of transactions does not satisfy one or more of the adjudication rules; bill a second entity for the use of the one or more of the products and services associated with the single user when the adjudication of the single transaction passes; deny the single transaction when the single transaction does not satisfy one or more of the adjudication rules; transmit a first response regarding the adjudication of the batch of transactions to the first vendor; and transmit a second response regarding the adjudication of the single transaction to the second vendor.

In further features, the first data structure includes: a member transaction identifier; a header portion; and a transaction portion.

In further features, the header portion includes: a date; a time; a vendor file identifier; a first vendor file name; a second vendor file identifier; an identifier of the first vendor; and a name of the first vendor.

In further features, the transaction portion includes: a carrier identifier; an eligibility group; a payment type; a unit count; a member identifier; a person number; a date of birth; an activation code; a universal pricing code (UPC) qualifier; a UPC; a first name; a last name; a contract; a claim identifier; a date of service; a record number; a vendor member timestamp; and a vendor patient identifier.

In further features, the second data structure includes: a claim identifier; a timestamp; a vendor identifier; a member portion; and an order portion.

In further features, the member portion includes: an identifier of a member; a first name of the member; a last name of the member; a carrier identifier; an eligibility group; a date of birth of the member; a person number of the member; a contract of the member; and a patient identifier of the member.

In further features, the order portion includes: a UPC; a UPC qualifier; a payment type for the single transaction; an activation code for the single transaction; a unit count for the single transaction; and a date of service of the single transaction.

In further features, the first API is a secure shell (SSH) file transfer protocol (SFTP) ingestion point configured to receive the batch of transactions using SFTP.

In further features, the second API is a representational state transfer (REST) API.

In a feature, a digital health solution system includes: a virtual pharmacy comprising one or more processors configured to operate a web portal for user devices via a network, the web portal serving as a marketplace for products and services available from vendors for consumption by users; a transaction processing module configured to: receive, via a network, a transaction from a vendor regarding one or more of the products and services consumed by one or more users via the virtual pharmacy for payment to the vendor; adjudicate the transaction using adjudication rules stored in memory; bill an entity for the use of the one or more of the products and services associated with the one or more users when the adjudication of the transaction passes; and transmit, via a network, a response regarding the transaction to the vendor.

In further features, the transaction processing module is configured to receive the transaction in a file including multiple transactions received from the vendor via a communication received using SFTP.

In further features, the transaction processing module is configured to convert the transaction into an object.

In further features, the transaction module is configured to convert the transaction into an object using J2C bean conversion.

In further features, the transaction processing module is configured to reject the transaction if a name of the file does not include a name of the vendor, an ID of the vendor, a present year, a present month, a present date, a present hour, a present minute, and a present second.

In further features, the transaction processing module is configured to: receive the transaction via an application programming interface (API); and transmit the response within less than 10 milliseconds of receiving the transaction.

In further features, the transaction processing module is further configured to: receive from the vendor, via the network, a request including a transaction identifier of the transaction using a second API; determine a status of the adjudication of the transaction using the transaction identifier; and transmit, via the network, the status of the transaction to the vendor.

In further features, the transaction processing module is configured to indicate that the transaction is corrupt when the transaction cannot be converted into an object.

In further features, the transaction module is configured to transmit a standard reject response before adjudicating the transaction using the adjudication rules in response to a determination that the transaction includes one or more errors.

In further features, the transaction module is configured to adjudicate multiple transactions in parallel.

In a feature, a digital health solution transaction management method includes: by one or more processors, via a network, operating a web portal for a virtual pharmacy for user devices, the web portal serving as a marketplace for products and services available from vendors for consumption by users; by one or more processors: receiving, via a network, a transaction from a vendor regarding one or more of the products and services consumed by one or more users via the virtual pharmacy for payment to the vendor; adjudicating the transaction using adjudication rules stored in memory; billing an entity for the use of the one or more of the products and services associated with the one or more users when the adjudication of the transaction passes; and transmitting, via a network, a response regarding the transaction to the vendor.

In further features, the receiving the transaction includes receiving the transaction in a file including multiple transactions received from the vendor via a communication received using SFTP.

In further features, the digital health solution transaction management method further includes converting the transaction into an object before the adjudicating.

In further features, the converting includes converting the transaction into an object using J2C bean conversion.

In further features, the digital health solution transaction management method further includes rejecting the transaction when a name of the file does not include a name of the vendor, an ID of the vendor, a present year, a present month, a present date, a present hour, a present minute, and a present second.

In further features: the receiving the transaction includes receiving the transaction via an application programming interface (API); and the transmitting the response includes transmitting the response within less than 10 milliseconds of receiving the transaction.

In further features, the digital health solution transaction management method further includes: receiving from the vendor, via a network, a request including a transaction identifier of the transaction using a second API; determining a status of the adjudication of the transaction using the transaction identifier; and transmitting, via a network, the status of the transaction to the vendor.

In further features, the digital health solution transaction management method further includes indicating that the transaction is corrupt when the transaction cannot be converted into an object.

In further features, the digital health solution transaction management method further includes transmitting a standard reject response before adjudicating the transaction using the adjudication rules in response to a determination that the transaction includes one or more errors.

In further features, the digital health solution transaction management method further includes adjudicating multiple transactions in parallel.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIGS. 6A-6E are graphical representations of example smartphone user interfaces for a digital health hub user interface.

FIGS. 7A-7H are graphical representations of example smartphone user interfaces for a health connect user interface.

FIGS. 9-11 are example smartphone user interfaces.

FIGS. 20A-2B are a functional block diagram of the transaction processing module of FIG. 19.

FIGS. 21A and 21B together include an example input file.

FIG. 22 includes an example of a data schema/structure that is created for sending to a Kafka topic module in JavaScript® Object Notation (JSON) format.

FIG. 23 is a flowchart depicting an example method of adjudicating transactions from vendors.

DETAILED DESCRIPTION

High-Volume Pharmacy

Figure 1:
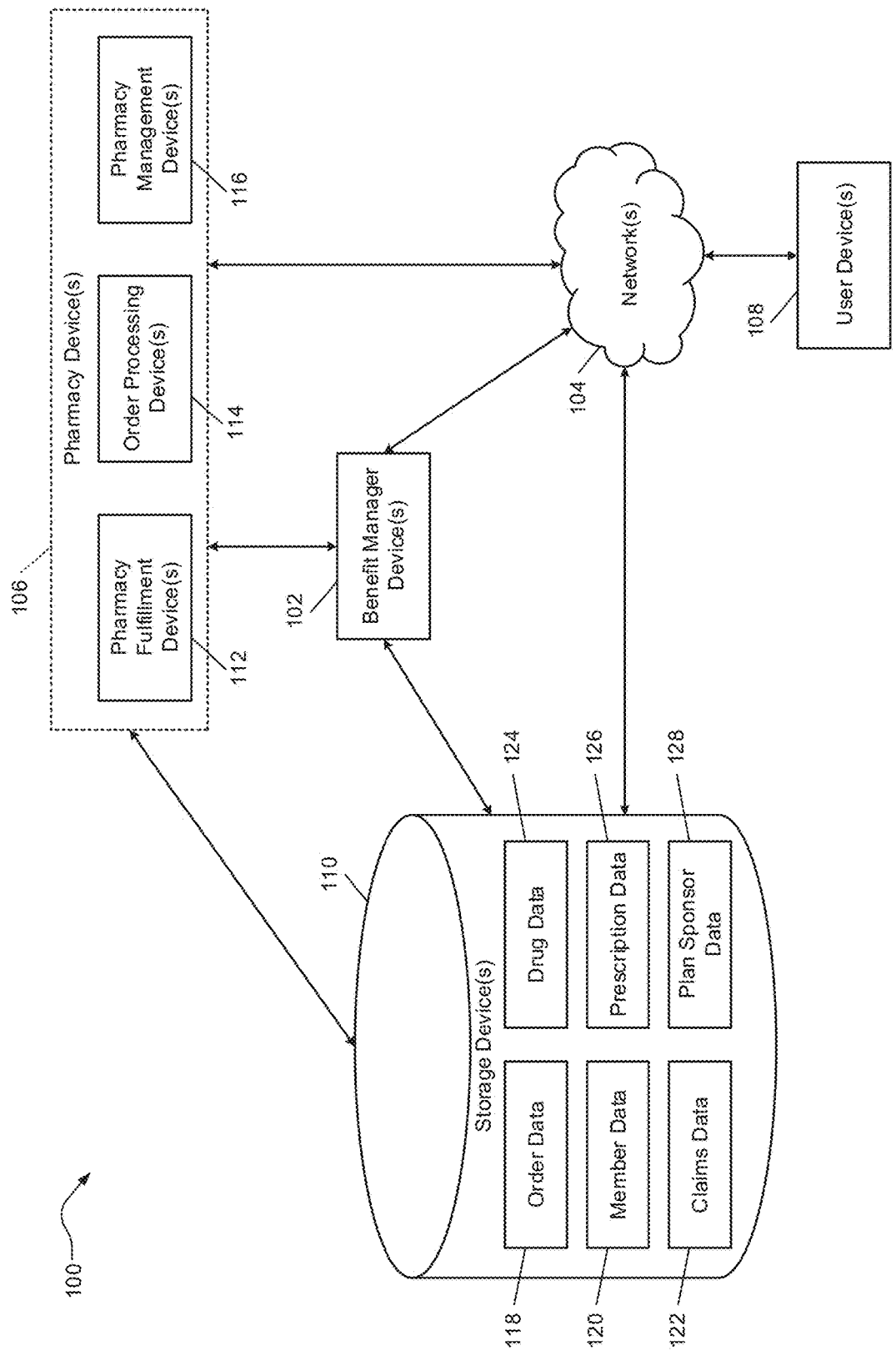
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
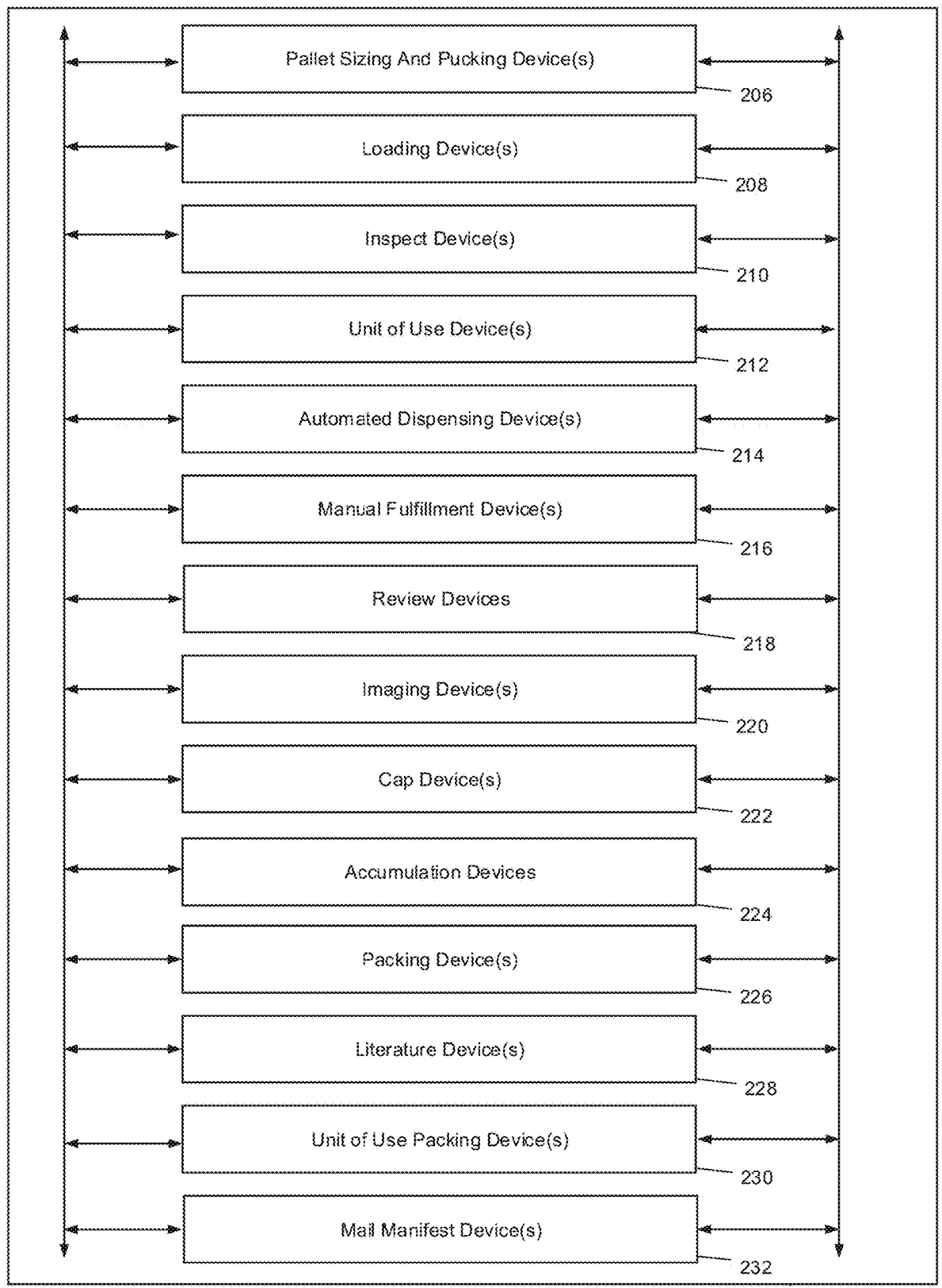
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
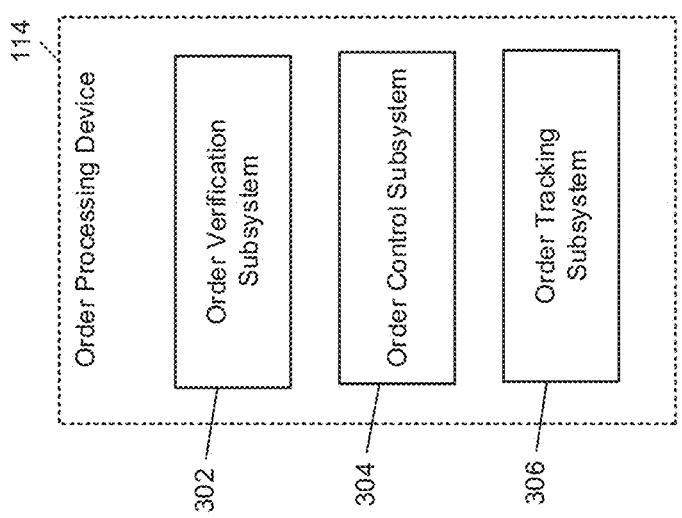
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver a pallet from the loading device 208 to the manual fulfillment device 216, to deliver a pallet from the loading device 208 to the automated dispensing device 214, and, to deliver paperwork from the literature device 228 to the packing device 226.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Digital Health Formulary

Digital therapies and interventions include software that prevents, manages, or treats a medical condition. Such digital health solutions may be used by patients independently or in concert with medications or devices (such as a digital scale or blood glucose monitor) to optimize outcomes. Ideally, the digital health solutions are developed according to, and supported by, objective evidence. Further, digital health solutions may be reviewed or cleared by regulatory bodies with respect to claims regarding risk and efficacy and with respect to guidelines for intended use.

Some digital health solutions may require a prescription from a licensed medical practitioner. For some digital health solutions, a prescription may only be required for certain use cases. Other digital health solutions do not require a prescription, but could be ordered or recommended by a licensed medical practitioner. For example only, digital health solutions can be grouped into 3 groups: those used in concert with medication, those used in concert with a device, and those used independently. An example of a digital health solution that is used in concert with a medication includes a sensor that fits onto a controller or rescue inhaler used to treat asthma. The sensor may monitor the frequency of usage of the inhaler and transmit that data back to an app/digital engagement platform where a person can track their usage over time. An example of a digital health solution that is used in concert with a device includes a cellular-enabled blood glucose meter that tracks a person's blood glucose. The meter sends the blood glucose measurements to an app/digital engagement platform where a person can have a visual/graphical representation of their blood glucose over time. An example of a digital health solution that is used independently includes digital cognitive behavioral therapy. Cognitive behavioral therapy is first line psychotherapy (talk therapy) for depression, anxiety and insomnia. Digital cognitive behavioral therapy is a digital (e.g., application based) version of therapy and a person only has to use a computer or mobile device to engage in treatment.

Evaluating claims made by the developers and providers of digital health solutions is a daunting challenge for interested parties, such as health plans, medical professionals, pharmacy benefit managers, and patients. Many of these parties don't have sufficient expertise in the necessary areas-including data science, medicine, UI/UX (user interface and user experience), privacy, information security, and software licensing-much less the available resources to evaluate the range of digital health solutions.

The present disclosure describes an architecture for aggregating information for a wide array of digital health solutions in a digital health marketplace, facilitating management of health plan coverage for digital health solutions via pharmacy benefit managers, and fulfilling prescribed or over-the-counter (OTC) digital health solutions through a virtual pharmacy.

Block Diagram

Figure 4:
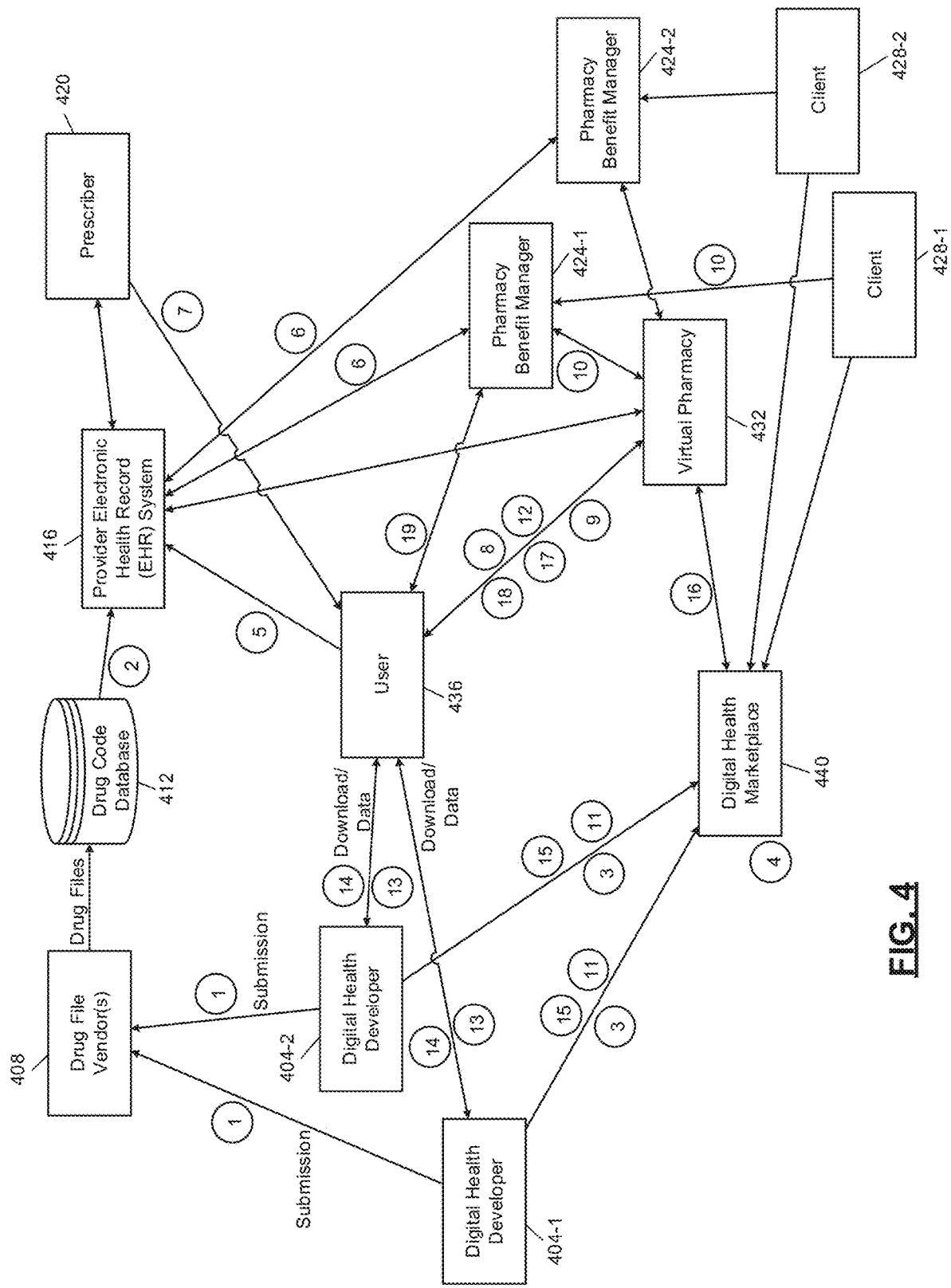
FIG. 4 is a functional block diagram of an example digital health solution distribution architecture.

In FIG. 4, digital health developers 404-1 and 404-2 (collectively, digital health developers 404) have each developed at least one digital health solution. While two are shown for illustration, in practical implementations there will be more digital health developers. The digital health developers 404 submit information about their respective digital health solutions to a drug file vendor 408. While a single rectangle is shown in FIG. 4 for ease of illustration, the digital health developers 404 may submit information to multiple drug file vendors. The drug file vendor 408 may be an existing drug file vendor, such as First Databank (FDB). In various implementations, the digital health developers 404 may submit information to an intermediary for interoperation with existing drug file vendors. In various implementations, one or more new entities may serve the role of a drug file vendor, in some cases in a limited role specific to digital health solutions.

The drug file vendor 408 prepares one or more drug files for a drug code database 412. These drug files may be categorized separately from medications traditionally encoded in drug files. Electronic health record (EHR) systems, such as a provider EHR system 416, rely on the drug code database 412 for populating and displaying data, such as to a prescriber 420. The prescriber 420 may be any medical professional licensed or authored to generate some form of prescription. For example, the prescriber 420 may be a doctor, a physician assistant, a nurse practitioner, etc.

The provider EHR system 416 interacts with one or more pharmacy benefit managers. In FIG. 4, two pharmacy benefit managers are shown for illustration: pharmacy benefit managers 424-1 and 424-2 (collectively, pharmacy benefit managers 424), one or both of which may be implemented by the benefit manager device 102 of FIG. 1. The pharmacy benefit managers 424 allow the provider EHR system 416 to determine coverage and payment information related to digital health solutions. A representative client 428-1 of the pharmacy benefit manager 424-1 is shown for illustration. Similarly, a representative client 428-2 of the pharmacy benefit manager 424-2 is shown for illustration. The clients 428-1 and 428-2 (collectively, clients 428) may be health insurers. The clients 428 supply coverage information to the pharmacy benefit managers 424 so that the pharmacy benefit managers 424 can make coverage and payment determinations.

A virtual pharmacy 432 allows a representative user (device) 436 to browse available digital health solutions, including any prescribed by the prescriber 420. For example only, the virtual pharmacy 432 may be implemented by the pharmacy device 106 of FIG. 1 and include one or more processors. The digital health solutions are aggregated, analyzed, and vetted by a digital health marketplace 440, which receives information about digital health solutions from the digital health developers 404. The digital health marketplace 440 may be embodied by, for example, one or more processors or one or more servers, and serve the virtual pharmacy 432 to users, such as the user 436.

Data Flow

In FIG. 4, circled numbers are displayed at locations (such as arrows indicating data interchange) where additional information will be described. The numbers do not necessarily imply an order. At location 1, the digital health developers 404 submit information for digital health solutions to the drug file vendor 408 for inclusion in the drug code database 412.

At location 2, the drug code database 412 sends information—for example, an NDC (national drug code) (e.g., associated with a digital health solution)—to the provider EHR system 416 for use by health care providers, including the representative prescriber 420. In various implementations, the drug file vendor 408 may not have defined NDCs for digital health solutions and so the digital health marketplace 440 may define proprietary NDCs for the (digital health) solutions from the digital health developers 404.

At location 3, the digital health developers 404 submit their digital health solutions to the digital health marketplace 440 for evaluation. The digital health developers 404 may also transmit other information to the digital health marketplace 440.

At location 4, professionals at or associated with the digital health marketplace 440 evaluate and score the digital health solutions based on criteria such as usability, technical scalability, security, adoption, empirical result data, etc. In various implementations, the digital health marketplace 440 may be configured to evaluate and score the digital health solutions automatically, for example, using machine learning. This information may allow the clients 428 to make informed decisions regarding inclusion of the digital health solutions in a digital health formulary. This information may also permit the virtual pharmacy 432 to prepare a tiered ranking of digital health solutions. For example, the digital health marketplace 440 may allow members to log in and see digital health solutions that the members are eligible for based on meeting predetermined clinical criteria and what the members' health benefits plans have paid for. In various implementations, the virtual pharmacy 432 may be configured to determine the tiered rankings automatically, for example, using machine learning. The digital health solutions that were successfully vetted may be combined into a digital health formulary maintained by the digital health marketplace 440. Carton tiers for each criterion may indicate successful vetting.

The vetting may be performed, for example, by expert panels employed by or coordinated by the digital health marketplace 440 and/or PBMs 424. The expert panels may include doctors, health policy PhD and Pharm.D. degree holders, certified digital usability and accessibility experts, etc. The experts may assess clinical and usability components of the digital health solutions. In addition, a value assessment may be performed on the digital health solutions, which may attempt to determine a return-on-investment based on established efficacy and pricing models of the digital health solutions. In addition, the digital health marketplace 440 may negotiate pricing models with the digital health developers 404, which may include per-person per-month costs with tiered volume discounts. Alternatively, evaluators of the digital health solutions may negotiate pricing models with the digital health developers 404. In various implementations, the digital health marketplace 440 may be configured to perform the vetting automatically, for example, using machine learning.

At location 5, the user 436 visits a medical provider (e.g., prescriber 420) that uses the provider EHR system 416.

At location 6, the medical provider (e.g., prescriber 420) checks for digital health solution formulary and eligibility of the user 436 based on health plan coverage. Depending on the identity of the user 436, the provider EHR system 416 may contact either the pharmacy benefit manager 424-1 or the pharmacy benefit manager 424-2 to perform these checks. In various implementations, the provider EHR system 416 may perform the formulary and eligibility checks for the user 436 in advance of the visit. For example, the provider EHR system 416 may batch process checks overnight for all scheduled visits the following day. In this way, the prescriber 420 can have instant access to eligibility and, in some cases, cost information.

In addition, the pharmacy benefit managers 424 may provide recommendations of digital health solutions relevant to the users to the provider EHR system 416 using, for example, an interface developed based on Fast Healthcare Interoperability Resources (FHIR). In various implementations, the pharmacy benefit managers 424 may determine the recommendations automatically, such as using machine learning. These recommendations could be presented to the prescriber 420 using, for example, a clinical guidance message in the provider EHR system 416. Other capabilities to present opportunities to the prescriber 420 as part of their workflows include HL7 FHIR application programming interfaces (APIs), Substitutable Medical Applications, Reusable Technologies (SMART) on FHIR apps, National Council for Prescription Drug Programs (NCPDP) standard electronic prescribing formats, and Clinical Direct messaging. The digital health market place digital channels and adjudication system may directly interact with the APIs to update data and perform transactions.

In conjunction with, or independent of, a scheduled visit, the pharmacy benefit managers 424 may provide recommendations of relevant prescription digital health solutions directly to the user 436. If interested, the user 436 can directly convey their interest in a prescription digital health solution to the prescriber 420, such as during an in-person visit. Additionally or alternatively, if the user 436 indicates interest in the prescription digital health solution using the virtual pharmacy 432, a prescription request could be provided to the prescriber 420, such as via the provider EHR system 416.

At location 7, the prescriber 420 provides a prescription for a digital health solution to the user 436. The prescription may be paper-based. In various implementations, the prescriber 420 may additionally or alternatively generate an electronic prescription for the user 436. The (electronic) prescription may be entered into the provider EHR system 416, which may communicate the electronic prescription to the virtual pharmacy 432.

At location 8, if the user 436 has already registered with the virtual pharmacy 432, the virtual pharmacy 432 may transmit a notification to the user 436 in response to receiving the prescription. For example, this notification may take the form of one or more of a text (or SMS) message, an email, a smartphone notification, an automated or personal voice call, etc. To access the virtual pharmacy 432, the user 436 may navigate, using a web browser on a smartphone or computer, to a web portal operated by the virtual pharmacy 432. The user 436 may additionally or alternatively access the virtual pharmacy 432 via executing a downloaded mobile application that interfaces with the virtual pharmacy 432. The mobile application may be obtained from a digital distribution platform, such as the GOOGLE PLAY digital distribution platform from Google LLC or the APP STORE digital distribution platform from Apple Inc. Example user interfaces for the mobile application are described below.

If the user 436 received a paper prescription, the paper prescription may include a uniform resource locator (URL)—for example a relatively short URL that can be easily typed—and/or a quick response (QR) code that can be scanned by a smartphone and decoded to reach a corresponding URL. The URL may connect the user 436 to a web portal of the virtual pharmacy 432. Additionally or alternatively, the website at the URL may include instructions regarding downloading a mobile application, including links to popular digital distribution platforms.

At location 9, the user 436 accesses the virtual pharmacy 432 to review digital health solutions, including those that have been prescribed as well as potentially others that may be available. In various implementations, the digital health marketplace 440 may display digital health solutions that are found in the same category within the digital health formulary as the prescribed digital health solution. This may be similar to the way that generics are available (or mandated) as alternatives to brand-name medications.

The virtual pharmacy 432 may allow for reviews to be submitted by the community. These reviews may be subject to moderation before or after being posted. The virtual pharmacy 432 may also display usage data collected via the digital health marketplace 440. For example, the usage data may include an average number of monthly users, a total number of lifetime users, monthly retention percentages, etc.

When the user 436 accesses the virtual pharmacy 432 in an over the counter (OTC) model (for example, if no prescriptions have been submitted for the user 436), the virtual pharmacy 432 may ask the user 436 a set of questions. Based on symptoms and needs revealed by answers to this set of questions, the virtual pharmacy 432 can recommend one or more digital health solutions to the user 436. The set of questions may be generated by a decision tree and/or a decision table implemented by a rules engine.

The virtual pharmacy 432 may implement a recommendation engine that takes the answers as inputs and generates a set of recommended digital health solution options for provision to the user 436. The recommendations may indicate whether a particular digital health solution is covered by their plan or not, along with pricing.

With or without recommendations, the user 436 may search through the digital health solutions in the virtual pharmacy 432 by category, symptoms, disease state, etc. The user 436 may be able to filter based on various criteria, including coverage and pricing.

As indicated at location 10, the coverage may be determined in real-time from an adjudication interface of one of the pharmacy benefit managers 424. For example, the adjudication interface of the DHSs may be developed based on FHIR. Additionally or alternatively, pricing may be determined in real-time from the adjudication interface of one of the pharmacy benefit managers 424.

The recommendations may be ranked according to coverage, pricing, and information provided by the digital health marketplace 440. For example, this information may include recommendation tiers (with higher tiers being reserved for digital health solutions that expert panels have determined to be efficacious, user-friendly, and offering a higher return on investment). The information may also include user feedback, social media impressions, adoption rate, etc.

At location 11, the digital health marketplace 440 determines activation criteria for the digital health solutions offered by the digital health developers 404. The activation criteria may include an activation token or activation code. For other digital health solutions, the activation criteria may be tied to unique identifying data. For example, the digital health developer 404-1 may permit access to a user who can demonstrate possession of a particular phone number or email address. In such a case, fulfilling (also referred to as "filling" or "dispensing") an order for the digital health solution on behalf of the user 436 may include the virtual pharmacy 432 providing the email address or phone number of the user 436 to the digital health marketplace 440. The DHM then passes the contact information to the digital health developer 404-1.

In another case, the digital health developer 404-2 may generate an activation token or activation code for each user. The digital health marketplace 440 may obtain an activation token/code in order to fulfill an order by the user 436. For some (or all) of the digital health solutions, the digital health marketplace 440 may instead cache one or more activation tokens/codes that can be immediately provided to the user 436 without requiring any additional communication with the digital health developers 404. Even when communication is not necessary, the respective one of the digital health marketplace 440 may advise the digital health developers 404 when an activation token/code has been assigned.

At location 12, the virtual pharmacy 432 provides the user 436 with a mechanism to access the digital health solution. This access mechanism may include an activation token/code. For example, the activation token/code may be embedded in a URL used to access or download the digital health solution. In other cases, as indicated above, possession of a particular phone number or email address (which may be verified by sending a randomized code via text or email, respectively) or activation code may be sufficient for activation.

The access mechanism may be a link to a digital distribution platform corresponding to an operating system on the device operated by the user 436. By using all-digital channels, the entire fulfillment workflow from prescription to obtaining the digital health solution may be accomplished within minutes. For example, adjudication may be performed by one of the pharmacy benefit managers 424 while a notification is supplied to the user 436 of availability of the digital health solution. In various implementations, that notification can be recalled in the event of unsuccessful adjudication. The user 436 may review terms of service for the digital health solution and then proceed to obtaining the digital health solution with a single click/tap following submission of a prescription by the prescriber 420.

At location 13, the user 436 downloads and activates the digital health solution. If the download is to a mobile device, the download may occur from a digital distribution platform to which the digital health developers 404 have uploaded their mobile apps, rather than from the digital health developers 404 themselves.

At location 14, the digital health developers 404 may collect usage data, which may be used to assess efficacy and comply with regulations. The usage data may include frequency of usage, length of use, etc.

At location 15, the data collected by the digital health developers 404 is shared with the digital health marketplace 440 in near real-time or on a schedule, such as nightly. If one or more predetermined patterns emerge (e.g., repeated elevated blood glucose measurements), this data can be used to trigger an outreach, such as by a pharmacist, to counsel the member, such as discussed further below. The data may be housed in various places and not necessary in the digital health marketplace 440.

At location 16, the digital health marketplace 440 updates rankings of digital health solutions based on usage data. For example, these changes may be made in near-real-time as new usage data is received. These changes may be reflected immediately in results shown by the virtual pharmacy 432.

The digital health marketplace 440 may also be able to, in real time, "recall" the digital health solution from the virtual pharmacy 432 (akin to taking a medication off the shelf in a physical pharmacy). Such a recall may be performed if a security or other issue is identified.

The digital health marketplace 440 and the virtual pharmacy 432 may have a two-way data synchronization, where the digital health marketplace 440 provides aggregated usage data per product (anonymized) and the virtual pharmacy 432 provides aggregated usage data per customer (also anonymized) as well as any community-driven data (e.g. reviews, feedback, etc.).

The digital health marketplace 440 may use the combined data set, as well as analysis of public news and social media through data mining and natural language processing (NLP) technology to provide an analytical view of a preferred ranking recommendation in near-real-time. The digital health marketplace 440 may also leverage the same data analysis technology above to understand any potential product risk, especially those involving non-medical situations (system crash, data leak, etc.). A human representative at the digital health marketplace 440 may be alerted in response to a determination that a digital health solution may need to be temporarily rendered unavailable.

At location 17, the virtual pharmacy 432 may provide real-time notification to the user 436 via their preferred channel on any app or usage updates, recalls, formulary changes, refills, etc.

At location 18, the user 436 may perform a refill through the virtual pharmacy 432, either automatically or with a minimal number of clicks/taps. With a digital health solution already installed on a mobile phone, the user 436 can indicate their desire to refill automatically (which may require reaching agreement on an upper price threshold). In various implementations, the upper price threshold may be set to free so that automatic refills occur so long as the digital health solution is still covered with no co-pay by the health plan. In the context of digital health solutions, a refill may simply be continuing to use the digital health solution, such as for another month or year. When enabled, the refill request and confirmation could be handled completely behind the scenes between the virtual pharmacy 432 and the digital health developers 404.

At location 19, the pharmacy benefit manager 424-1 (assuming that the pharmacy benefit manager 424-1 is the relevant PBM for the user 436) can use real-time and historical claims information to recommend OTC digital health solutions to the user 436 that are in the formulary on their corresponding health plan. For example, the pharmacy benefit manager 424-1 may be programmed to identify symptoms based on claims history for the user 436. Meanwhile, the pharmacy benefit manager 424-1 synchronizes with the digital health marketplace 440 to create a clinical mapping between symptoms and relevant digital health solutions.

As new or better digital health solutions relevant to the user 436 are identified by the pharmacy benefit manager 424-1, a notification can be provided to the user 436. In fact, the notification can be sent to the user 436 even if the user 436 has not yet registered to use the virtual pharmacy 432 or has even heard of the virtual pharmacy 432. In various implementations, other entities may perform similar recommendation functions. However, these entities may need to obtain access to claims data from the pharmacy benefit manager 424-1 or medical data from another source, such as the provider EHR system 416.

User Interface

Figure 5:
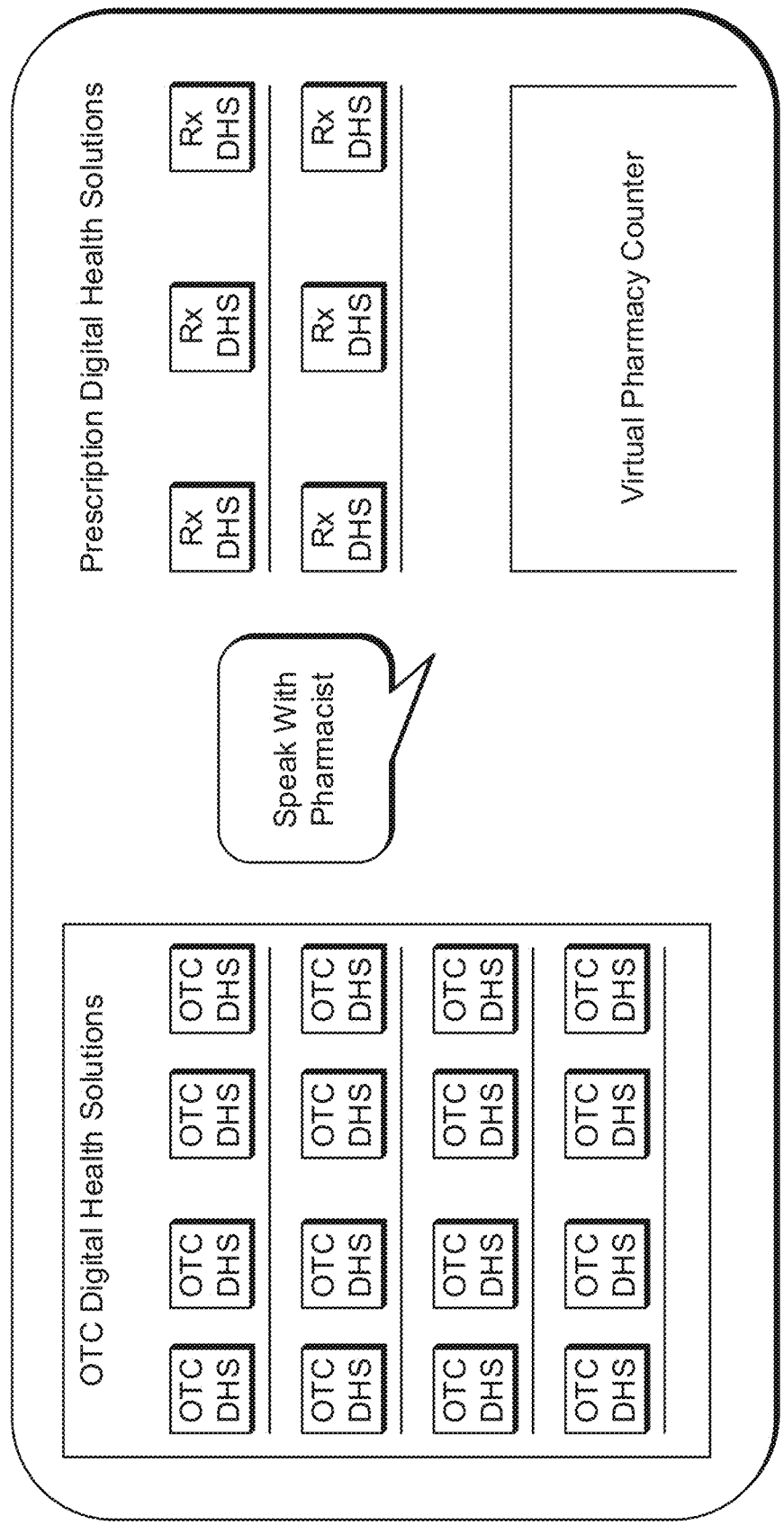
FIG. 5 is a graphical representation of an example web-based interface for the virtual pharmacy.

FIG. 5 is an example web-based interface for the virtual pharmacy 432. The interface includes virtual "shelves" of OTC digital health solutions (abbreviated as DHS), a virtual pharmacy counter with prescription digital health solutions "behind the counter," and a button for the user to request a conversation with a pharmacist chatbot triage. Digital therapeutics (sometimes abbreviated DTx) are a type of digital health solution.

In various implementations, the user is only shown the OTC digital health solutions that are specifically clinically targeted for the user and are covered by their health plan (e.g., as determined by a pharmacy benefit manager). Although covered, the cost may still be non-zero. In other implementations, the user may be presented with all of the OTC digital health solutions by category (e.g., pulmonary, cardiovascular) or by symptom (e.g., depression). Each OTC digital health solution may be displayed with an indication (such as an icon) of whether the OTC digital health solution is covered or not.

If the user selects an OTC digital health solution that is covered, the user may be taken through a clinical eligibility screening via the OTC digital health solution developer. If the user is clinically eligible for the OTC digital health solution, then the user is allowed to enroll and either pays in full personally, pays a copay, or pays nothing, depending on plan coverage. As described above, in response to payment, the user may receive a download link to the digital health solution. The download link may include an embedded activation code. The user may download the digital health solution to a computing device for execution via the download link and/or the activation code.

If the user selects an OTC digital health solution that is not covered by their benefit plan, the user may still be taken through a clinical eligibility screening via the OTC digital health solution developer. If the user is clinically eligible for the OTC digital health solution, then the user is allowed to enroll and pays full price for the OTC digital health solution. The full price may have been negotiated by the digital health marketplace 440.

If the user was prescribed a prescription digital health solution, then an adjudication and drug utilization review (DUR) may have been performed at the time of submission of the prescription digital health solution. Assuming successful adjudication and DUR, the user may see the prescription digital health solution waiting for them "behind the counter" of the virtual pharmacy. Examples of behind the counter prescription digital health solutions are illustrated in FIG. 5 by Rx DHS. The user can then enroll and, depending on plan coverage, either pay nothing, the appropriate co-pay, or in full.

In FIGS. 6A-6E, example smartphone user interfaces for a digital health hub (e.g., digital health marketplace) are shown. The smartphone user interfaces may be displayed to a user via a display of a smartphone, a tablet, or another suitable type of computing device.

In FIG. 6A, the user can select whether to register for the first time (leading to a registration process depicted in FIG. 6C) or log in (leading to a login process depicted in FIG. 6B). In FIG. 6B, the user supplies a username and password and, if multi-factor authentication is enabled, presents another factor. In FIG. 6C, the user supplies personally-identifiable information. If the user is known to the virtual pharmacy, such as if the virtual pharmacy shares personally-identifiable information with a pharmacy benefit manager (as may be the case where they are operated by a common entity), then benefit information may automatically be pulled into the virtual pharmacy from the pharmacy benefit manager. Otherwise, the user may have to enter/input benefit information, such as health plan enrollee or group identifiers, or the personally identifiable information, such as name, date of birth (DOB), address, social security number (SSN), and email.

FIG. 6D depicts an example welcome screen presented to the user upon successful login via inputting a username and a password of a previously registered account. Selecting the button for "Your Medicine Cabinet" causes the application to transition to an interface such as that depicted in FIG. 6E. The selection may be, for example, a touch input received within boundaries of the button.

In FIG. 6E, the user is presented with their OTC and prescription digital health solutions. The user may also be presented with their medication history via a medical-history application programming interface (API). Additionally, a "health summary" section may be displayed with data, such as average blood glucose, average blood pressure, and/or weight over a historical period, such as the prior week or month. Information in the health summary can be displayed pictorially, graphically, or numerically.

The user may be able to directly access each digital health solution through the app by pressing the corresponding button (e.g., OTC DHS 1, OTC DHS, 2, Rx DHS 1). Authentication to the digital health solutions may be handled via a single-sign-on mechanism so that the user does not have to maintain separate credentials for each of the digital health solutions.

The application may accumulate data, such as usage data and medical data, from each of the digital health solutions and feed the accumulated information back to the virtual pharmacy via a real-time API. This may eliminate the need for batch data transfers from or to the digital health solution developers.

Data may also be transferred from the virtual pharmacy or the digital health solution developers to a Health Action Plan (HAP) portal. The HAP portal allows Therapeutic Resource Center (TRC) pharmacists—pharmacists that are disease specialized, answer medication questions from users, and monitor clinical alerts—to view clinical alerts and reach out to users.

FIGS. 7A-7H are example smartphone user interfaces for a health connect application that may be displayed. The smartphone user interfaces may be displayed to a user via a display of a smartphone, a tablet, or another suitable type of computing device. FIG. 7A represents an initial screen presented to the user upon launching of the health connect application. In response to selection of the login option, the user interface of FIG. 7B may be presented. FIG. 7B may allow a user to login by inputting a username and a password associated with a previously registered account. In response to selection of the register option, the user interface of FIG. 7C may be presented. FIG. 7C may allow a user to create and register a new account.

Upon successful login or registration, the user interface of FIG. 7D may be presented. In response to the user selecting "Your Virtual Pharmacy," the user interface of FIG. 7F may be presented. In response to the user selecting "Your Medicine Cabinet/Pillbox," FIG. 7E may be presented.

In FIG. 7F, the user is presented with the choice between their prescriptions and shopping for other digital health solutions. In response to the user selecting "Shop," the user interface of FIG. 7G may be presented. In response to the user selecting "Your Rx," FIG. 7H may be presented. Presentation as used herein may include at least one of a display of information on a display and audible output of information via one or more speakers.

The user interface of FIG. 7G may separate OTC digital health solutions that are covered under the user's benefits coverage from OTC digital health solutions that are not covered under the user's benefit coverage. The user interface of FIG. 7G may also include a button for the user to request a conversation with a pharmacist chatbot triage or live phone call for any medication related questions.

The user interface of FIG. 7H may separate digital health solutions prescribed to the user by prescriber. The user interface of FIG. 7H may also include a button for the user to request a conversation with a pharmacist chatbot triage.

Figure 8:
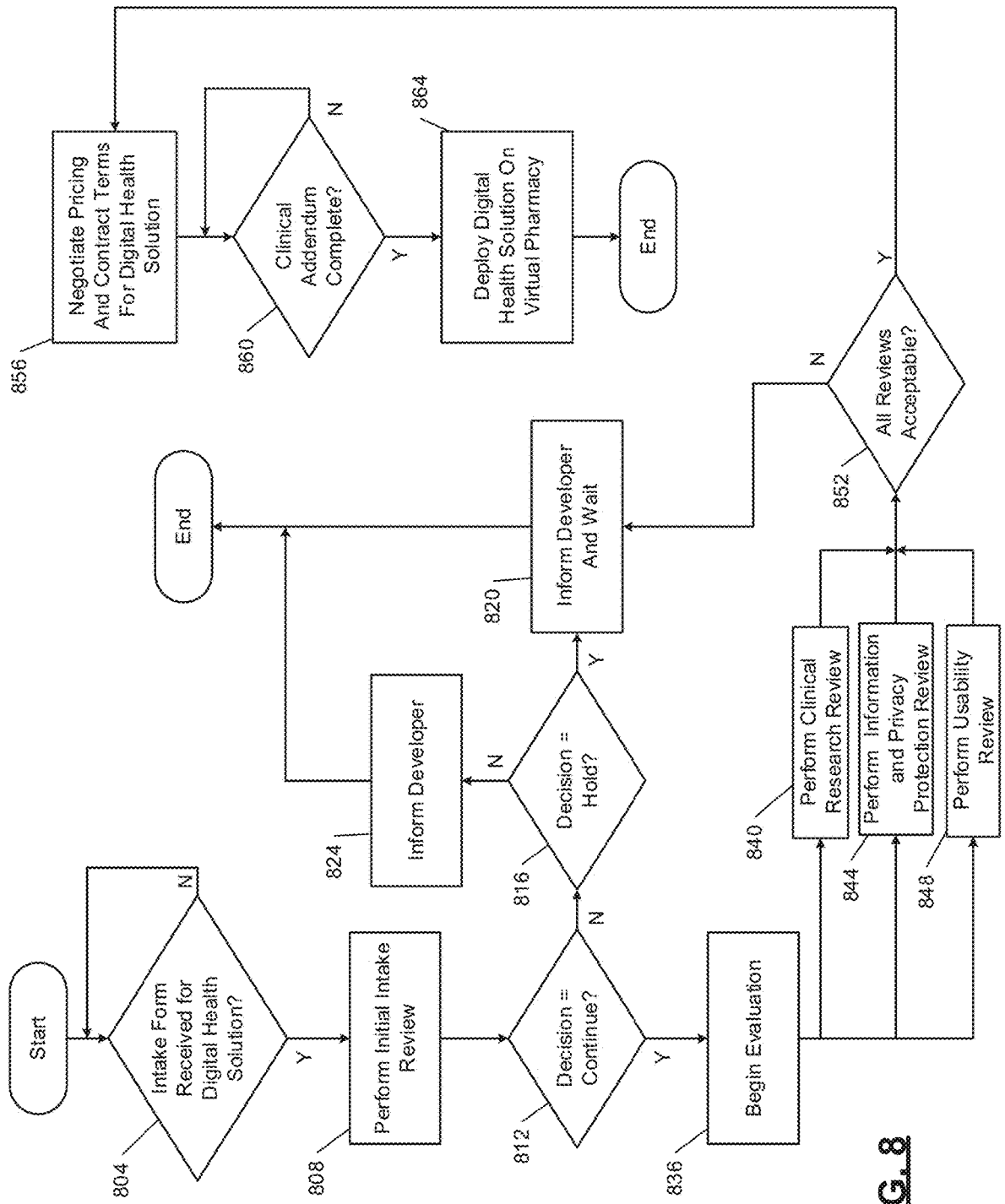
FIG. 8 is a flowchart depicting an example method of deploying a digital health solution on a virtual pharmacy.

FIG. 8 is a flowchart depicting an example method of deploying a digital health solution on the virtual pharmacy 432. Control begins with 804 where the digital health marketplace 440 determines whether an intake form has been received from a digital health developer 404 for a new digital health solution that is proposed to be distributed via the virtual pharmacy 432. If 804 is true, control continues with 808. If 804 is false, control remains at 804 or may end.

At 808, an initial intake review is performed. The initial intake review may be performed via a review of the intake form, for example, by a panel including one or more pharmacists, physicians, health outcomes research professionals having PhDs, a PBM digital product team, and user experience experts with knowledge in usability, accessibility, and member experience. The intake form provides the panel with answers to a set of pertinent questions that guide the determination regarding whether the digital health developer 404 should move on to the next stage of the vetting process. The initial intake review includes: (a) a clinical review, (b) a privacy, security, and stability review, and (c) a business and accountability review. The clinical review includes a review of: (i) credentials of medical personnel on developer's staff, (ii) a review of whether the developer is solving a clinical problem that needs a solution via the digital health solution, (iii) the developer's clinical approach to the solution, (iv) a review of presented clinical evidence, (v) a review of research methodology, (vi) a review of statistical significance of results, and (vii) an effect of the solution if used incorrectly. The privacy, security, and stability review includes reviewing (i) a HITRUST certification or a SOC II mapping to HITRUST certification and (ii) scalability. The business and accessibility review includes reviewing (i) whether the developer has articulated a clinical pain point, problem statement, and proposed solution, (ii) a number of members utilizing the developer's solution, (iii) a length of time that the developer has been in business, and (iv) web content accessibility and guidelines (WCAG) 2.0 compliance of the developer. There may also be a usability review which includes member experience experts that test user-friendliness, tracking and syncing with other devices, and ensure accessibility requirements (e.g., WCAG 2.0) are met.

The initial intake review results in a decision to one of: continue vetting; hold vetting for more information; and reject (at least for now) the opportunity to distribute the digital health solution via the virtual pharmacy 432.

At 812, a determination is made whether the decision (from the initial intake review) is to continue with the vetting of the distributor and the digital health solution. If 812 is true, control continues with 836, which is discussed further below. If 812 is false, control transfers to 816. At 816, a determination is made whether the decision (from the initial intake review) is to hold vetting. If 816 is true, the developer is informed of the decision to wait for more data, public research, or a potential pilot opportunity in the future at 820. If 816 is false, the developer is informed of the decision to deny the opportunity at 824. Feedback and reasoning may be given to the distributor if requested. The feedback may encourage the developer to re-submit an intake form in the future once areas of opportunity and/or weakness are addressed.

At 836 (when the decision from the initial intake review is to continue), evaluation of the developer and the digital health solution is begun. A non-disclosure agreement may also be entered into with the developer. The evaluation includes performing a clinical research review at 840, an information and privacy protection review at 844, and a usability review at 848, 840, 844, and 848 may be performed in parallel, for example, to minimize the period necessary to complete the evaluation, or sequentially, for example, to minimize resources. 840, 844, and 848 may be performed by different groups, for example, for increased accuracy of the results of the evaluation.

The clinical research review may be performed at 840, for example, by a group of health researchers (e.g., PhD level), medical doctors, and others. 840 may include reviewing all public studies, posters, published outcomes, ROI methodology, food and drug association (FDA) dossiers if any, and pre-released documents provided by the developer. The information and privacy protection review may be performed at 844, for example, by digital product and clinical teams. 844 may include a review of usability of the digital health solution. A full, live demo of the digital health solution may be navigated and tested by the digital product and clinical teams. Others may also test the demo, such as individuals living with or directly impacted by the condition mitigated by the digital health solution. The following areas may be examined during 844: (i) flow and logic of the digital health solution, (ii) engagement strategy of the digital health solution, (iii) ease of syncing of any (external) devices to the digital health solution, (iv) ability of the digital health solution to integrate into the flow of a potential users everyday life, and (v) whether any clinical language and recommendations made within the digital health solution satisfy one or more standards. 844 may also include ensuring that the digital health solution is compliant with one or more accessibility guidelines, such as to ensure that the digital health solution could be made available to all users of the virtual pharmacy 432.

Because the developer may be able to access protected health information (PHI) and personally identifiable information (PII) if the digital health solution is deployed, 848 may include reviewing security of the developer to ensure that the developer satisfies one or more security standards. This may include completion and review of a security questionnaire, assessment of security capabilities and maturity of the developer, a vulnerability assessment of the digital health solution, inspection of evidence of compliance with the security standard(s), security alignment to service industry standards, such as HITRUST, NIST, HIPPA, and payment card industry standards. 848 may also include completion of a risk assessment of the developer.

In various implementations, the reviews of 840-848 may be performed automatically, for example, using trained machine learning models or in another suitable automated manner.

At 852, control determines whether the reviews of 840-848 have all indicated that the digital health solution, developer, or both are acceptable. If 852 is false, control may transfer to 820, as discussed above. If 852 is true, control may continue with 856.

At 856, contract terms and pricing for the digital health solution are negotiated with the developer of the digital health solution. At 860, a determination is made regarding whether a clinical addendum has been completed, if necessary. If 860 is true, the digital health marketplace 440 makes the digital health solution available via the virtual pharmacy 432 at 864, and control may end. If 860 is false, control may remain at 860. In various implementations, 860 may be omitted.

In FIG. 9, another example smartphone user interface for a digital health hub (e.g., virtual pharmacy) is shown. As shown in FIG. 9, the virtual pharmacy may also display devices in addition to digital health solutions (applications). The devices may be connectable to user devices or available for purchase via the virtual pharmacy.

Figure 10:
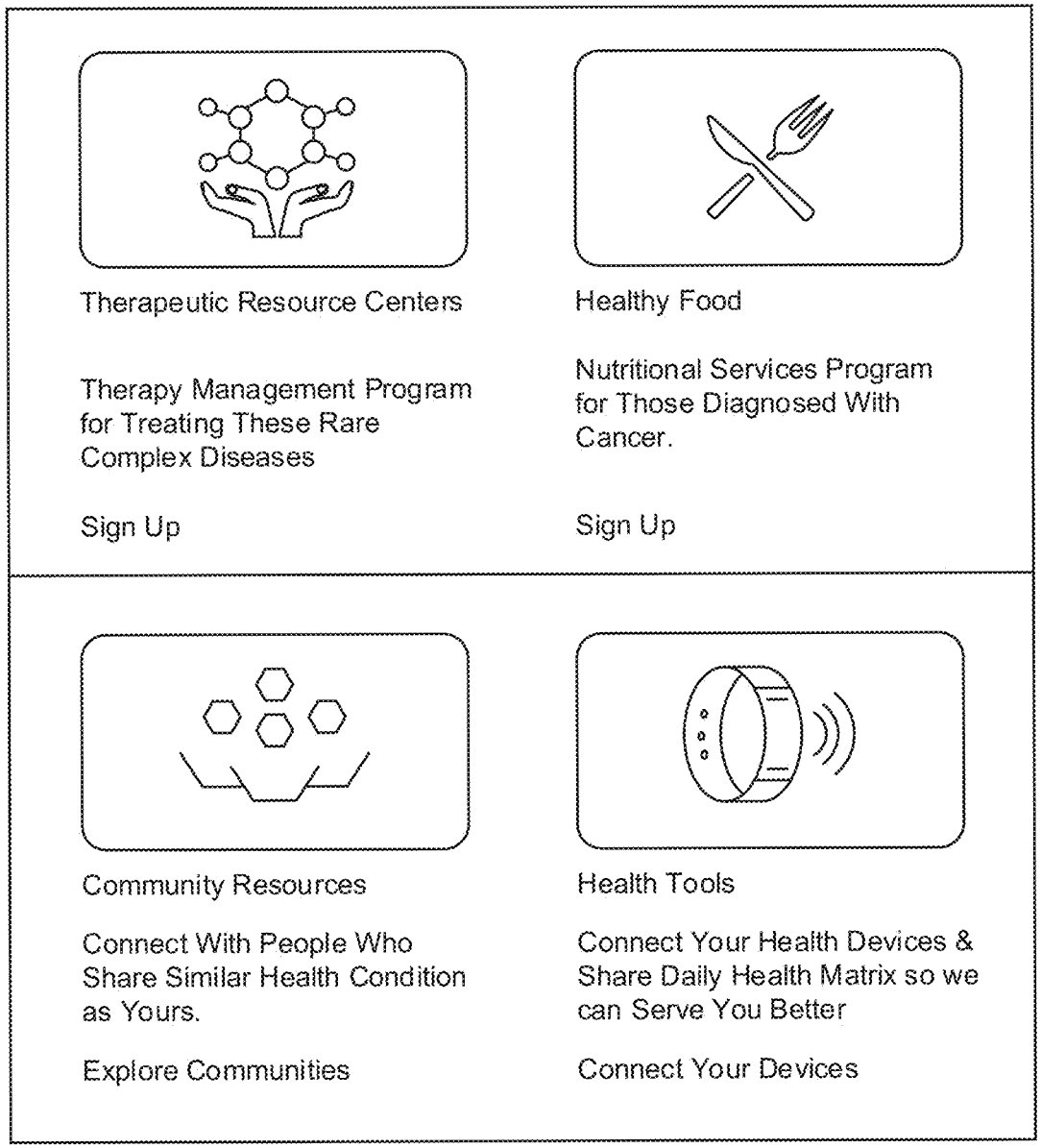

In FIGS. 10 and 11 other example smartphone user interfaces for a digital health hub (e.g., virtual pharmacy) are shown. As shown in FIG. 10, the virtual pharmacy may also display links to resources that are non-disease specific (general). These may be referred to as general wellness resources. As shown in FIG. 11, the virtual pharmacy may also display links to resources that are disease specific (i.e., specific to a disease of the user). Examples include disease specific partner programs, disease specific therapeutic resources, disease specific cuisine (e.g., via a partner, such as Therapease cuisine), disease specific community resources, etc.

Figure 12:
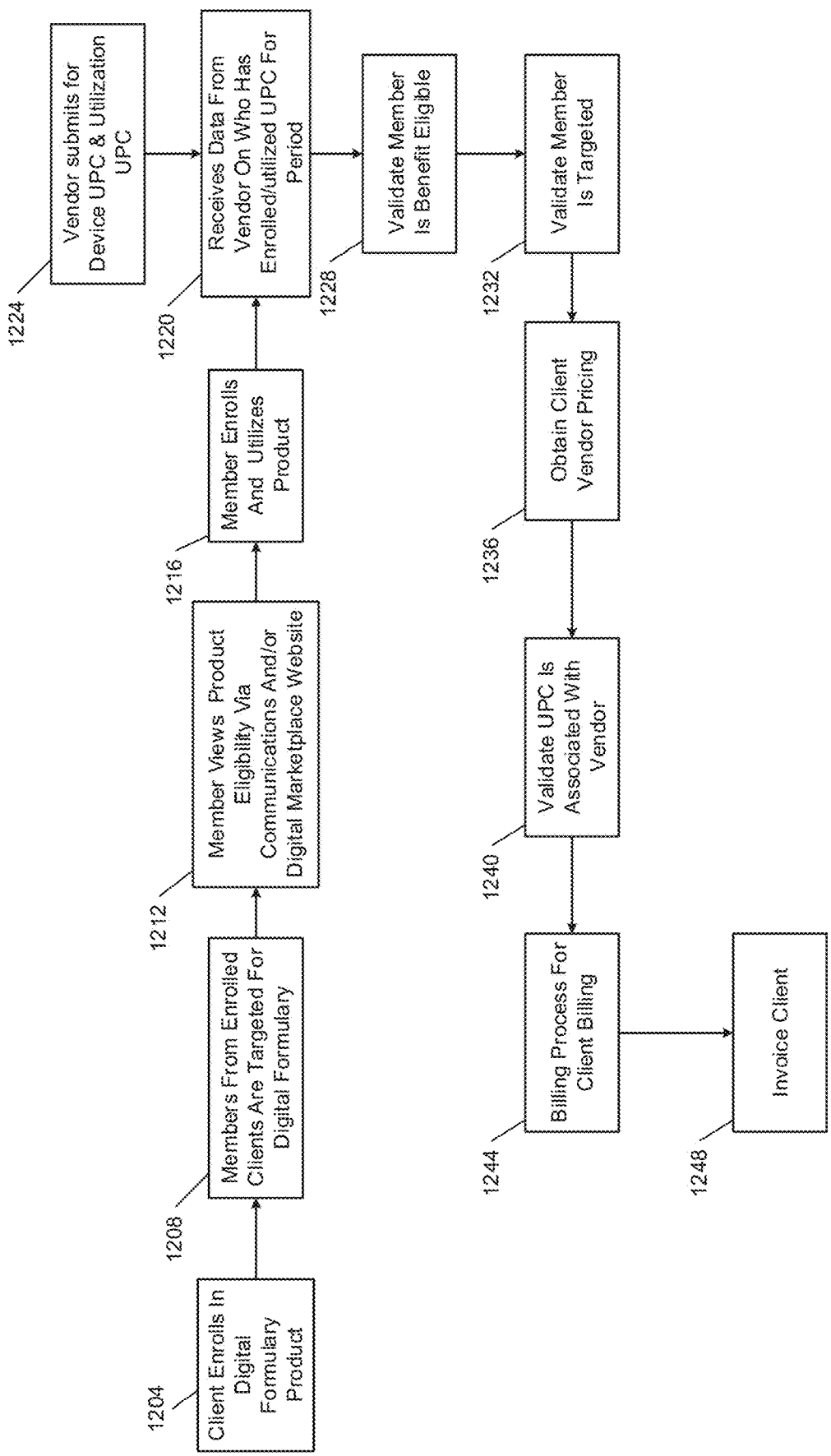
FIGS. 12-17 are flowcharts depicting examples of managing member communications, member enrollments, and control of digital pharmacy products.

FIG. 12 is a flowchart depicting an example method of digital health solution (product) distribution, control, and billing. Control begins with 1204 where a client (a user) enrolls in use of a digital formulary product. Digital formulary products include digital health solutions (e.g., applications). At 1208, the virtual pharmacy may target one or more users from enrolled clients are targeted by the virtual pharmacy for use of the digital formulary product. The virtual pharmacy may target users, for example, based on the users having symptoms or diseases that are associated with the digital formulary product.

At 1212, the targeted (or non-targeted) members view product eligibility information for the digital formulary product via communications (e.g., letters, emails, messages, etc.) regarding the digital formulary product and/or other information, such as the digital health marketplace and/or a website associated with the digital formulary product. At 1216, a member enrolls for use in the digital formulary product and utilizes the digital formulary product, such as by executing the digital formulary product on a user device.

At 1220, the virtual pharmacy receives data from the vendor of the digital formulary product regarding which one or more members have used the digital formulary product (e.g., the unique product code, UPC, associated with the digital formulary product for at least a predetermined period (e.g., 1 month). At 1224, the vendor of the digital formulary product submits utilization information (e.g., period of use) for each digital formulary product of the vendor and for each unique user device (e.g., a UPC of the user device) using that digital formulary product.

At 1228, the virtual pharmacy determined whether (or verifies that) the member is eligible for a benefit, such as a price reduction for the digital formulary product etc. At 1232, the virtual pharmacy determines whether (or verifies that) the member has been targeted for use of the digital formulary product.

At 1236, the virtual pharmacy obtains pricing for the digital formulary product between clients (including the member) and the vendor of the digital formulary product. At 1240, the virtual pharmacy validates that the UPC of the digital formulary product is associated with (of) the vendor. This ensures that payment for the digital formulary product is routed to the proper vendor. At 1244, a pharmacy benefit manager performs billing associated with billing a client (e.g., an insurance carrier) for the digital formulary product use by the member. At 1248, the pharmacy benefit manager transmits an invoice to the client for the use of the digital formulary product by the member.

Figure 13:
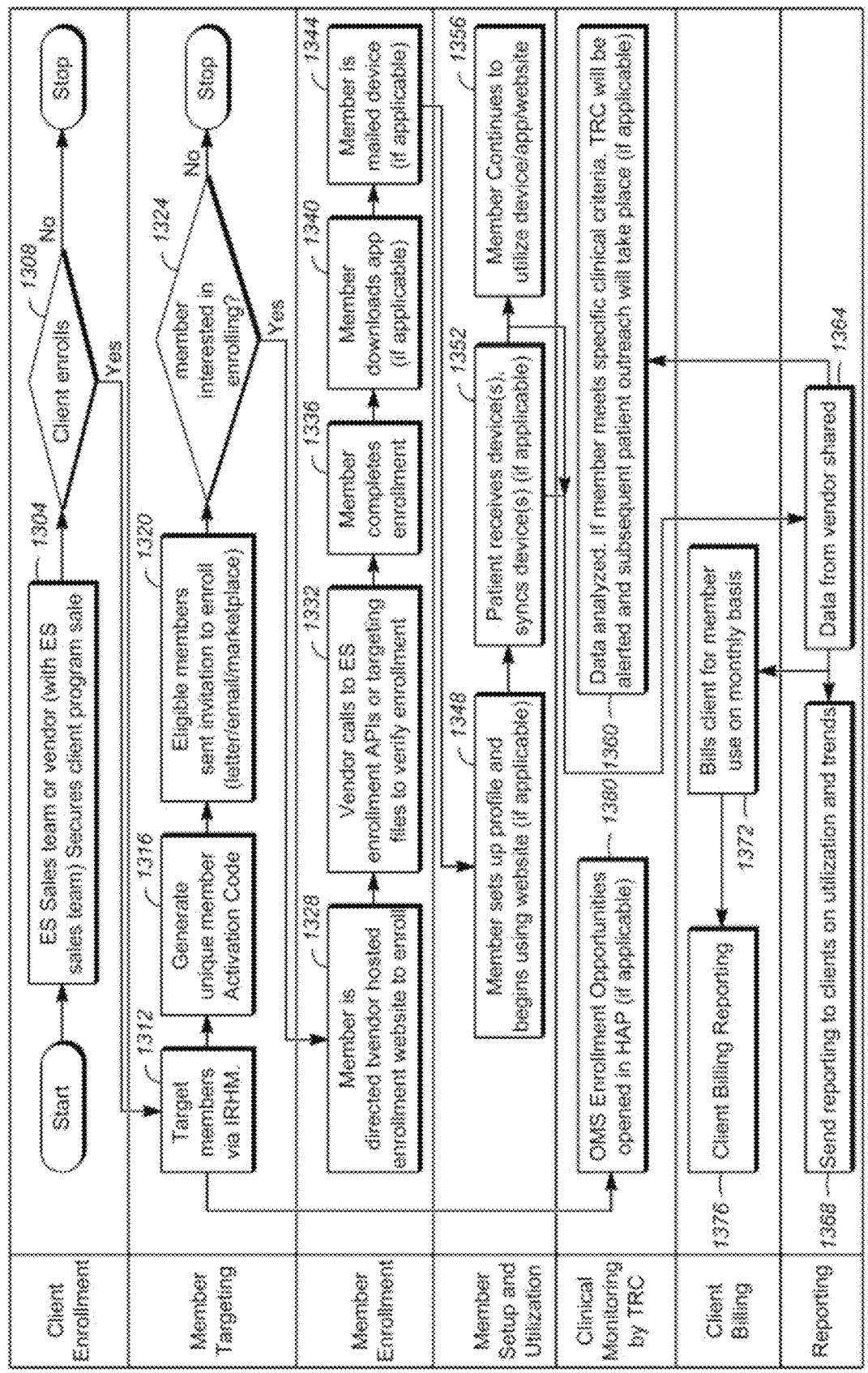

FIG. 13 is flowchart regarding use of a digital formulary product by a member. At 1304, a client program sale is secured, such as by a sales team associated with the virtual pharmacy or vendor along with such a sales team. At 1308, a determination is made regarding whether a client (e.g., an insurance carrier or a member) has enrolled. If 1308 is true, control may continue with 1312. If 1308 is false, control may end.

At 1312, one or more members of the client are targeted using an integrated human resource management (IHRM) system. The IHRM may use machine learning to determine which members to target. Alternatively, one or more individuals may determine which members to target. At 1316, the virtual pharmacy generates activation criteria (e.g., unique member activation codes) for targeted members. At 1320, the virtual pharmacy sends (and the targeted members receive) invitations to enroll in use of the digital pharmacy product and include the unique activation criteria generated for the targeted members. The virtual pharmacy may send, for example, letters, emails, messages, etc. indicative of the offer to enroll for the use of the digital pharmacy product. At 1324, the virtual pharmacy determines whether a targeted member is interested in enrolling for use of the digital pharmacy product. If 1324 is true, control continues with 1328. If 1324, control may end.

At 1328, the member is directed (e.g., via the sent invitation) to a website, such as a website hosted by the vendor of the digital pharmacy product for enrollment. The website may include a logo or other branding of the virtual pharmacy or an affiliate of the virtual pharmacy.

At 1332, the vendor may transmit a call to an API of the virtual pharmacy or targeting files to verify enrolment of the member for use of the digital pharmacy product. If verified, control continues with 1336. At 1336, the member completes the enrolment with the vendor of the digital pharmacy product. At 1340, the member downloads the digital pharmacy product (if necessary) to the user device. At 1344, the member may be mailed a user device for use of the digital pharmacy product (if necessary).

At 1348, the member sets up a profile with the vendor and begins using the digital pharmacy product (e.g., the application, the device, or a website). At 1352, the member receives the device (if sent a device) and syncs the device with one or more other devices, if necessary. At 1356, the member utilizes the digital pharmacy product. The vendor collects usage data indicative of usage of the digital pharmacy product by the member, as discussed above.

At 1364, the usage data regarding usage of the digital pharmacy product by the member (and other instances of the digital pharmacy product by other members) is shared with the virtual pharmacy, such as via a push operation from the vendor or a pull operation by the virtual pharmacy. At 1368, the virtual pharmacy may transmit a report to clients (e.g., insurance carriers) regarding utilization and trends in the usage data.

At 1360, the usage data may be analyzed (e.g., by the virtual pharmacy to determine whether a member (using the digital pharmacy product) meets one or more clinical criteria. If so, the virtual pharmacy or the TRC may reach out to the member, such as by physical mail, email, message, phone call, etc. In various implementations, the TRC may be automated and reach out automatically.

At 1372, the virtual pharmacy may bill clients for use of the digital pharmacy product by members of the client on a periodic basis, such as monthly. At 1376, the virtual pharmacy undergoes client billing reporting.

At 1380, the virtual pharmacy identifies OMS enrolment opportunities and opens instances of the OMS enrolment opportunities in a HAP (e.g., database). The HAP may be an application configured to identify and provide clinically related outreaches to members. The OMS may be computerized (e.g., for example utilizing machine learning) and include a database that includes solution related data configured to trigger designated outreaches.

Figure 14:
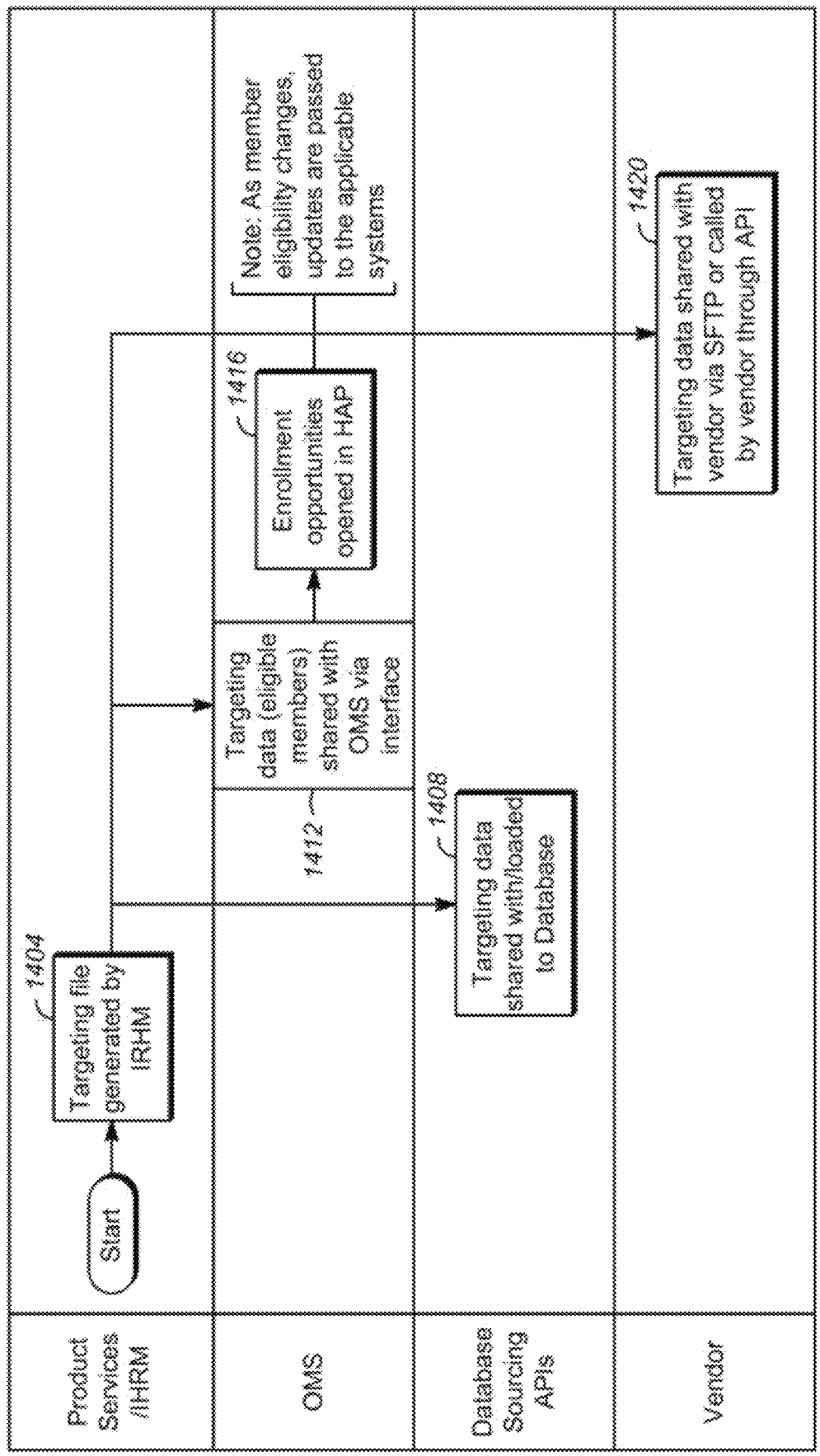
Figure 15:
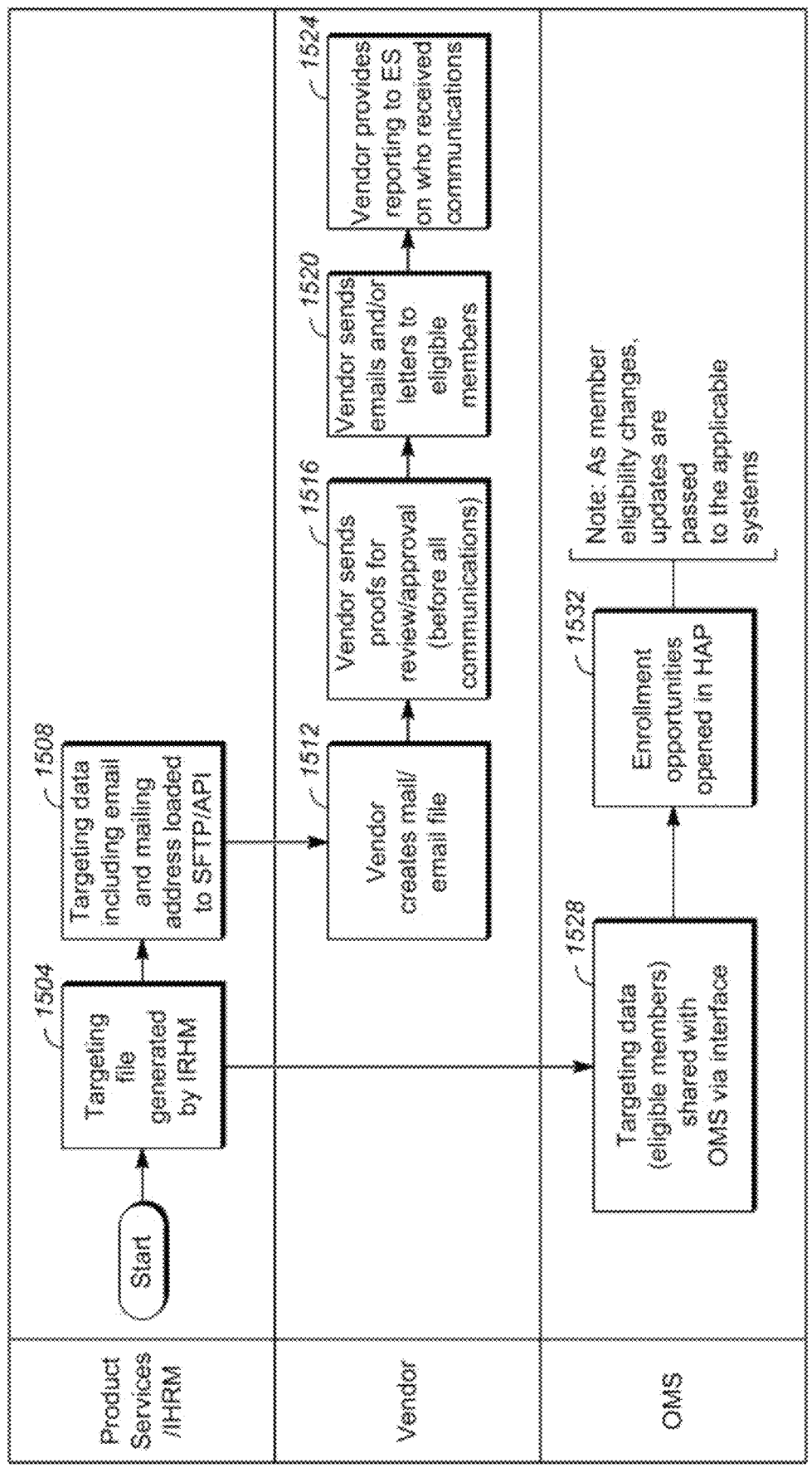

FIG. 14 is a flowchart depicting an example method of managing members for a digital pharmacy product. At 1404 a targeting file regarding targeting a member is generated by, for example, the IRHM system. At 1408, the targeting data/file is shared with or loaded to a database. At 1412, the targeting data/file (or a collection of data/files for multiple targeted members) is shared with an OSM via an interface. At 1416, entries for enrolment opportunities of the members are opened in a HAP. As member eligibility changes, updates are passed to the applicable systems, such as the OSM and the HAP. At 1420, the targeting data/file may be shared with a vendor. The sharing with the vendor may occur over a secured connection, such as through an API or using the secure shell (SSH) file transfer protocol (SFTP) or another suitable protocol for secure data transfer.

FIG. 14 is a flowchart depicting an example method of managing members for a digital pharmacy product. At 1504 a targeting file regarding targeting a member is generated by, for example, the IRHM system. At 1508, targeting data including an email address of the member and a physical mailing address of the member is located, for example, using the API or SFTP.

At 1512, the vendor of the digital pharmacy product creates a mail/email file for contacting the member. At 1516, the vendor sends the mail/email file to the virtual pharmacy for review and approval before contacting the member by mail or email as presented in the mail/email file. If approved, at 120 the vendor sends email and/or physical mail to the member's email address and/or mailing address. At 1524, the vendor provides the virtual pharmacy with information on who received (and/or reviewed) the communications. The vendor may track reviews of the communications sent by email.

At 1528, the targeting data/file (or a collection of data/files for multiple targeted members) is shared with an OSM via an interface. At 1532, entries for enrolment opportunities of the members are opened in a HAP. As member eligibility changes, updates are passed to the applicable systems, such as the OSM and the HAP.

Figure 16:
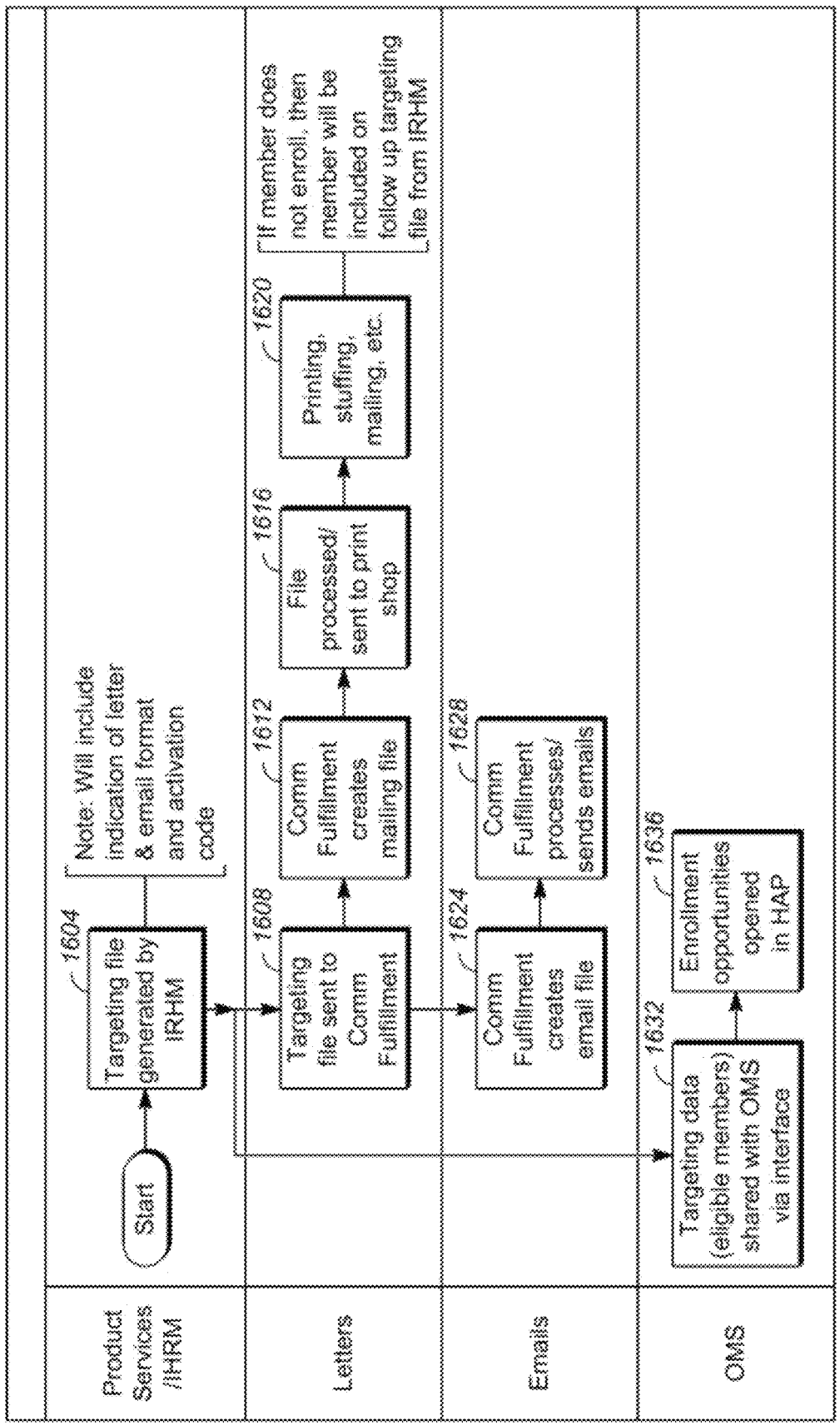

FIG. 16 is a flowchart depicting an example method of managing communication with members regarding a digital pharmacy product. At 1604 a targeting file regarding targeting a member is generated by, for example, the IRHM system. At 1608, the targeting file is transmitted to a communications (comm) system for fulfillment. The communications system may create a mailing file for mailing information regarding the digital pharmacy product to the member at 1612. At 1616, the mailing file is processed and sent to a printer (e.g., a print shop). At 1620, the mailing file is printed, stuffed into an envelope, and mailed to the member. If the member does not enroll for the digital pharmacy product, the member may be followed up with (e.g., by mail or electronically) one or more times.

At 1624, the communications system generates an email file for emailing information regarding the digital pharmacy product to the member. At 1628, the communications system sends an email including the email file to the member at the email address of the member.

At 1632, the targeting data/file (or a collection of data/files for multiple targeted members) is shared with an OSM via an interface. At 1636, entries for enrolment opportunities of the members are opened in a HAP. As member eligibility changes, updates are passed to the applicable systems, such as the OSM and the HAP.

Figure 17:
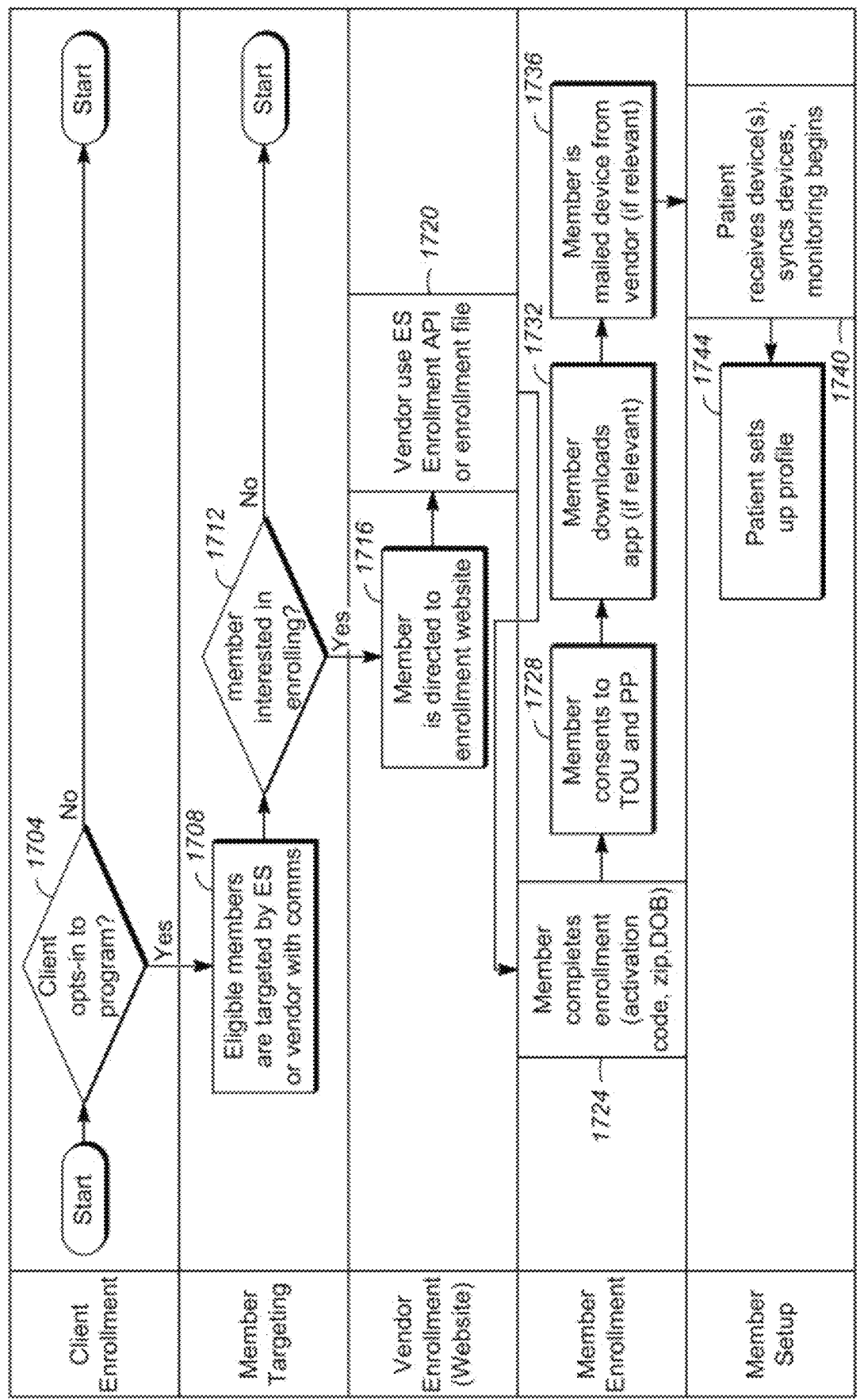

FIG. 17 is a flowchart depicting an example method of targeting and enrolling members for use of a digital pharmacy product. At 1704, a determination is made whether a client (e.g., an insurance carrier) has opted into a program for marketing of the digital pharmacy product. If 1704 is true, control continues with 1708. At 1708, eligible members of the client are targeted by the vendor of the digital pharmacy product or the virtual pharmacy or both as discussed above via one or more communications. At 1712, a determination is made regarding whether a member is interested in enrolling. If 1712 is true, control continues with 1716.

At 1716, the member (that is interested in enrolling) is directed to (e.g., via the sent invitation) to a website, such as a website hosted by the vendor of the digital pharmacy product for enrollment. The website may include a logo or other branding of the virtual pharmacy or an affiliate of the virtual pharmacy. The vendor may interface the virtual pharmacy via an enrollment API of the virtual pharmacy or an enrolment file at 1720.

At 1724, the member completes his or her enrollment. This includes inputting valid activation criteria (e.g., an activation code), a zipcode of the member, and a date of birth (DOB) of the member. At 1728, the member agrees with terms of use (TOU) and a privacy policy (PP) for use of the digital pharmacy product. At 1732, the member downloads the digital pharmacy product (if necessary) to the user device. At 1736, the member may mail a user device for use of the digital pharmacy product (if necessary).

At 1740, the member receives the device (if sent a device) and syncs the device with one or more other devices, if necessary. At 1744, the member sets up a profile with the vendor and begins using the digital pharmacy product (e.g., the application, the device, or a website).

Transaction Processing

Figure 18:
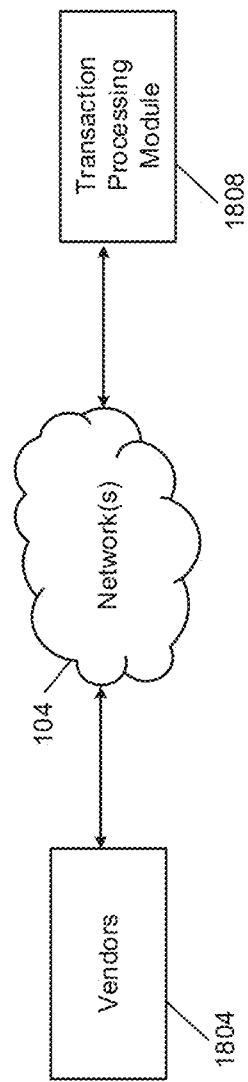
FIG. 18 is a functional block diagram of an example transaction processing system.

FIG. 18 is a functional block diagram of an example transaction processing system. Vendors 1804 include the digital health technology providers and other entities that provide their products and services to members via the virtual pharmacy 432 (or digital health fomulary (DHF)). Clients may be the entities that procure health insurance and services from a provider of the virtual pharmacy 432 and make the virtual pharmacy 432 available to their members (e.g., employees and employees' families). Members include patients utilizing the products and services offered on the virtual pharmacy 432.

The virtual pharmacy 432 includes a transaction processing module 1808 that adjudicates digital health billing claims and bills clients for devices and access to various products on a periodic (e.g., monthly) basis. The transaction processing module 1808 includes multiple claim ingestion points, such as a representational state transfer (REST) API that provides real time (synchronous) feedback (approve/reject status) per claim/transaction (such as in 10 milliseconds or less) and an SFTP ingestion point that provides batch processing of flat files. The transaction processing module 1808 also includes a status API that enables vendors of products and services offered on the virtual pharmacy 432 to check the status (approve/reject) of a transaction later after the transaction is submitted using a unique identifier of the transaction. This provides a system that vendors can use in multiple ways to submit and obtain feedback on transactions, both synchronously and asynchronously.

The transaction processing module 1808 also performs claim/transaction adjudication and generates billing invoices and reversals for clients. The transaction processing module 1808 also generates remittance invoices for vendors and summary reports for vendors. The transaction processing module 1808 also provides a front end portal for transaction data analysis that is accessible internally and may be accessible via vendors. The transaction processing module 1808 also provides other functions, as discussed further below. The vendors 1804 interact and communicate with the transaction processing module 1808 via the network(s) 104.

Figure 19:
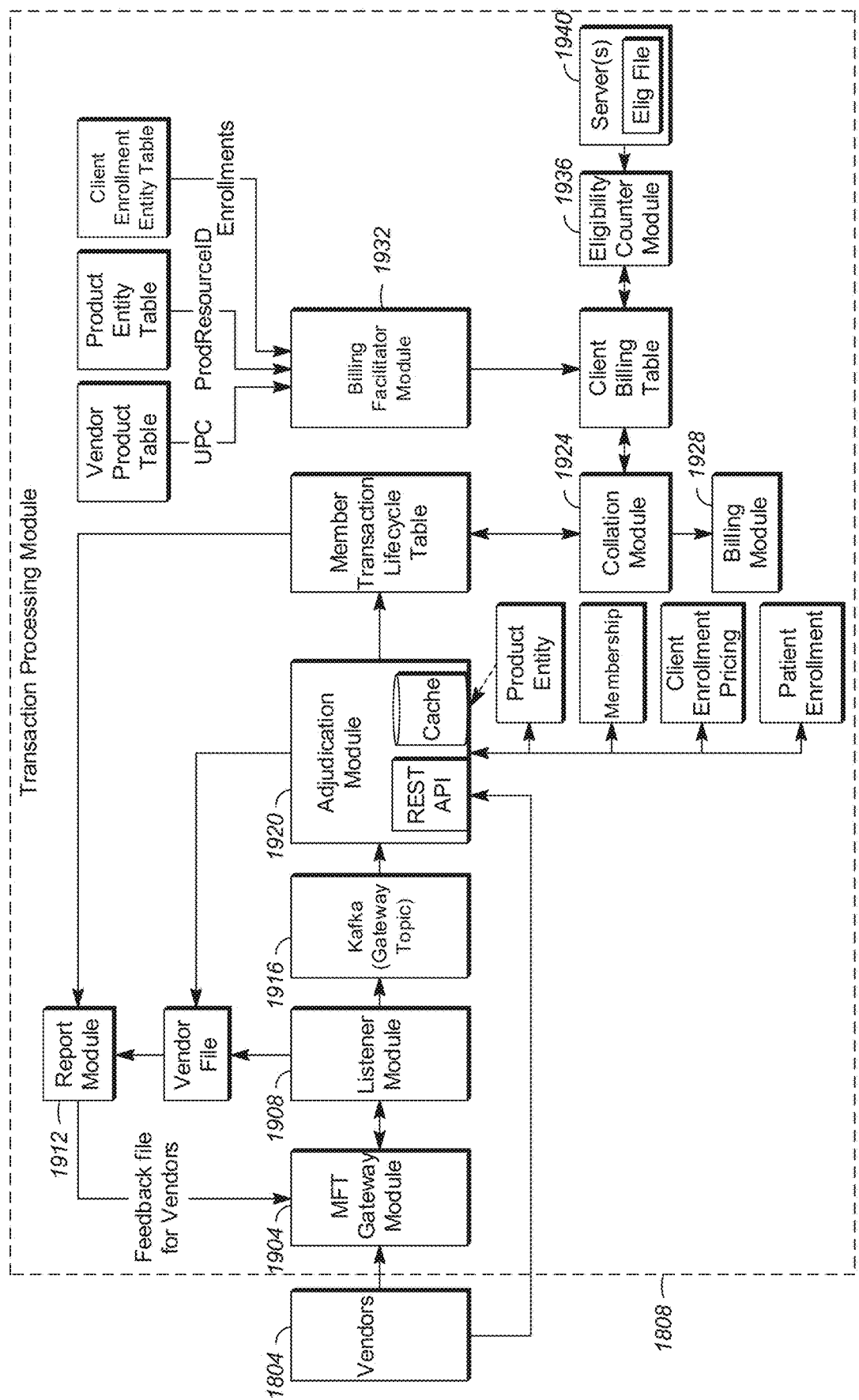
FIG. 19 is a functional block diagram of an example implementation of a transaction processing module.
Figure 20A:
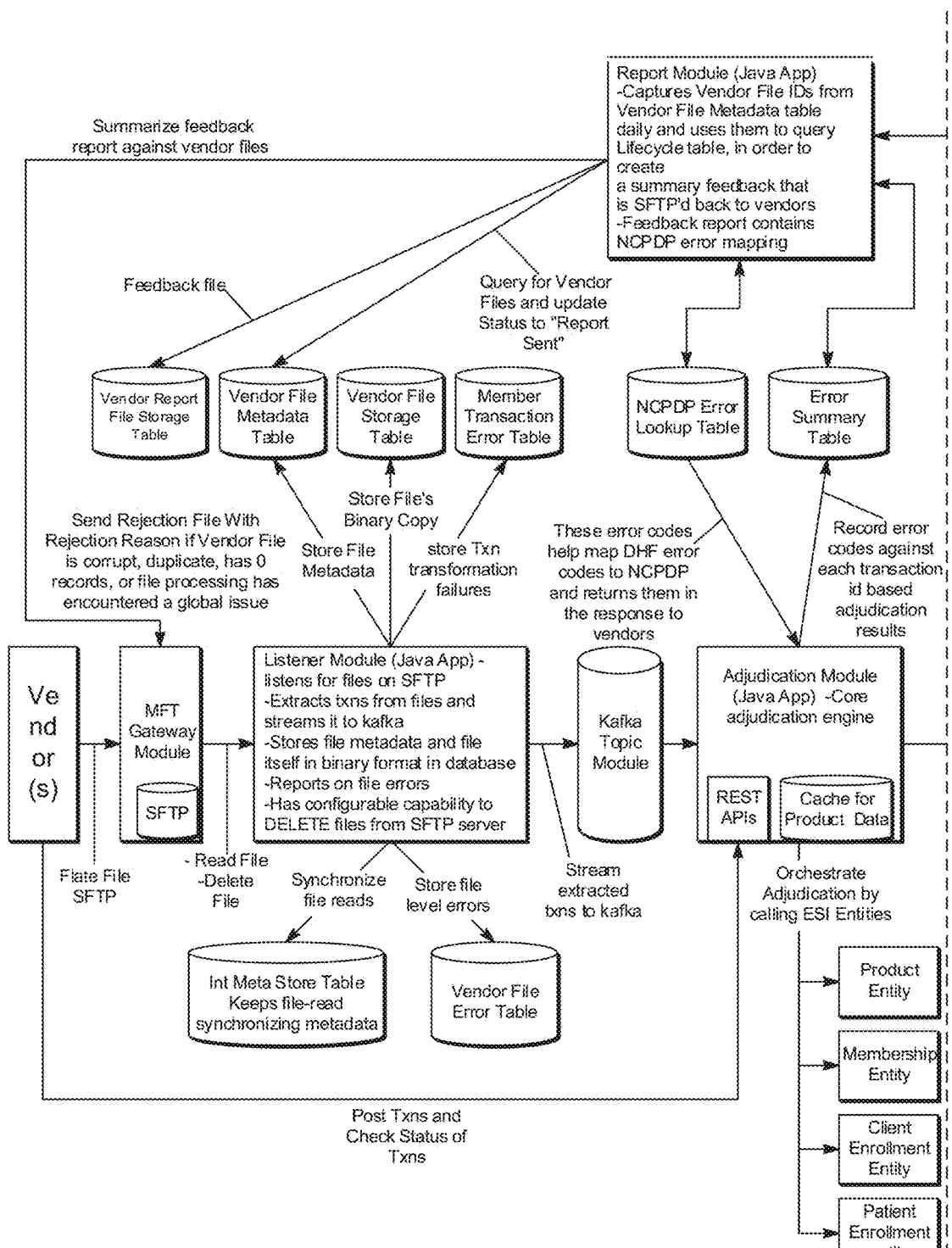
Figure 20B:
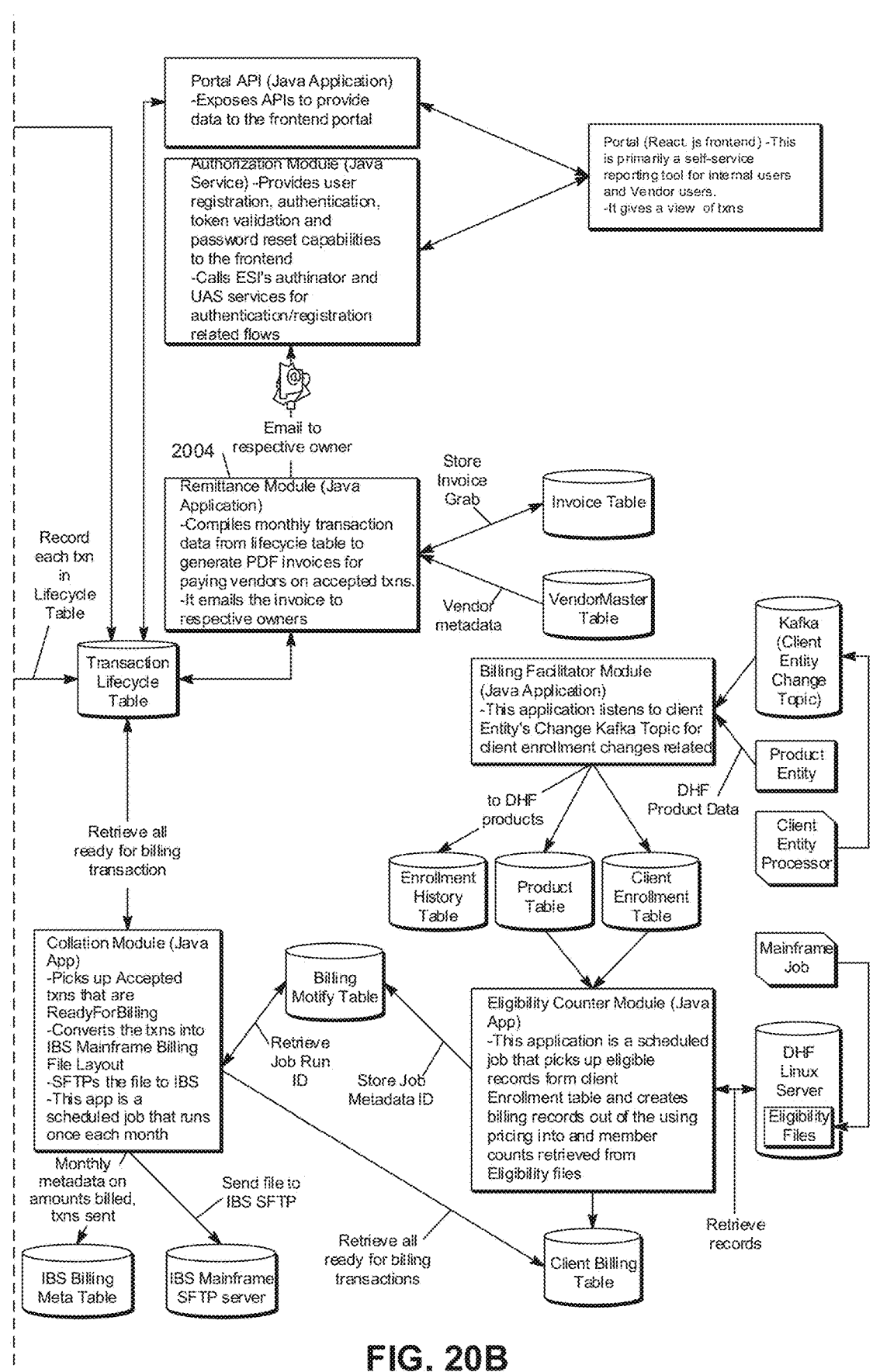

FIG. 19 is a functional block diagram of an example implementation of the transaction processing module 1808. FIGS. 20A-2B are also a functional block diagram of the transaction processing module 1808 of FIG. 19.

Each vendor is provided with an SFTP connection setup for interfacing a managed file transfer (MFT) gateway module 1904. The MFT gateway module 1904 is a gateway to receive files (e.g., flat files) from the vendors 1804 and other entities over one or more networks, such as the Internet. The MFT gateway module 1904 communicates via SFTP, which is a secure file transfer protocol over the internet that enables secure and encrypted transfer of files.

The vendors 1804 can use SFTP to send transactions in a file or use the hyper text transfer protocol (HTTPs) API to send individual transactions. Thus, two different channels of ingesting transactions is provided by the transaction processing module 1808. The HTTPs API is discussed further below.

Once the vendors 1804 are setup with their respective connections, the vendors 1804 can send and receive files over the SFTP via the MFT gateway module 1904. The MFT gateway module 1904 moves the received files/transactions to a desired inbound folder which a listener module 1908 is listening to, to pick up the files.

There's also an outbound folder provided for the MFT gateway module 1904. When the feedback (e.g., rejected files or summary feedback) is to be sent to a vendor, a report module 1912 enters the feedback file into the outbound folder with a routing-id prefix on the file name, which helps the MFT gateway module 1904 to transmit the file externally to the appropriate vendor. More specifically, the MFT gateway module 1904 selects one of the vendors 1804 based on the routing-id prefix of a file and transmits the file to the selected one of the vendors 1804.

Files to be transmitted to vendors are stored in the outbound folder for the MFT gateway module 1904. The vendor files have a predetermined layout and include large volumes of vendor transactions. The vendor files also have a predetermined naming convention that allows the system to recognize the vendor file for processing. The vendor files have a text format, and each transaction is represented by a new row.

For example, input billing files received from vendors (for payment to the vendors) may follow the following naming convention including a vendor name, a vendor ID, a present year, a present month, a present date, a present hour, a present minute, and a present second.

VendorName-VendorID-BILLING-CCYYMMD-DHHMMSS

For example: VENDORXYZ-FS3242A-BILLING-20200110134534

Input files not following the above naming convention may be rejected and reported to the sending vendor. The vendor name and vendorID of a vendor may be provided by an operator of the virtual pharmacy 432.

FIGS. 21A-21B include an example input file. The file data structure is divided into 3 parts:
  Header Row—Begins with HDR
    Header contains metadata about the file and symbolizes the first row in the file Detail Rows—Begins with DTL
  Detail contains that actual data about a transaction.
Trailer Rows—Begins with TRL
  Trailer contains other metadata such a total number no. of transactions and symbolizes the end of the file.

Input files are a fixed length format file, which means that each value has its own specified location across the characters in a row. Each value has its own starting position and ending position. Metadata of the data structure is utilized by the listener module 1908 in order to extract data from an input file.

Once the file reaches the desired MFT location (folder) that the listener module 1908 is listening to, the file gets picked up by the listener module 1908 for processing. The listener module 1908 may be an application hosted on a server and may be written in the Java® programming language. More specifically, the application may be built using the Java 8® programming language and the Spring® software development framework or another suitable type of programming language and/or framework. The listener module 1908 establishes a connectivity Kafka messaging queue and a Postgres database. The listener module 1908 listens to the folder where inbound files from vendors are placed. The listener module 1908 picks up the files, validates them, extracts individual transactions, converts them into an object data structure and sends the converted data structure to a Kafka topic module 1916 for consumption by an adjudication module 1920. The adjudication module 1920 adjudicates transactions using adjudication rules stored in memory.

How often the listener module 1808 polls the folder for new files is configurable and may be, for example, every 1 hour or another suitable period. The listener module 1808 polls the input folder, it may look for a maximum number of files, such as 1 or more than 1 file.

Files in the folder not having the predetermined naming convention will not be picked up (read) by the listener module 1908. Also, files will not be picked by the listener module 1908 if they have already been read by the listener module 1908. This filtering is may be enabled by a cache (e.g., a JdbcMetaDataStore) that uses an INT_METADATA_STORE table in a database as its source of truth. The cache also enables the listener module 1908 to run multiple instances on the server without erroneously ingesting files. Because of particular Spring® software development framework used, there may be three entries to this table per file processed (and one for files that do not meet the predetermined naming criteria conventions). Each of the three entries has a different value. While the example of three entries is provided, the present application is also applicable to other numbers of entries.

The listener module 1908 transfers files from the input (SFTP) folder to local memory of the listener module 1908 when an input file having the predetermined naming convention is identified. Once the file is transferred to the local memory, the listener module 1908 may first retrieve the file's name and make an entry into a VendorFileStorage table. This may help ensure safe operation, for example, even if the listener module 1908 suffers an error and the file needs to be processed again. The listener module 1908 may also use this action to protect against duplicate files. The VendorFileStorage table has a constraint on the file's name, which should be unique based on the vendor name, vendor Id, and the time it was sent. If the file is a duplicate, the listener module 1908 early exits the process and transmits a "Standard Reject Response" (SRR) to the vendor.

A "Standard Reject Response" (SRR) is transmitted when the listener module 1908 exits the process early and makes at least one entry into a VendorFileError table. The listener module 1908 inputs a reject file into the outbound (SFTP) folder for transmission to the vendor by the MFT gateway module 1904. The name of the reject file is the name of the file that was ingested, suffixed with a keyword summary of why it the file was rejected (e.g., DUPLICATE-PROPELLER-VEN0001-BILLING-20200313142359). The contents of the reject file includes text with more detail into the why the listener module 1908 rejected the file.

The listener module 1908 continues to parse and validate the file, such as in the following order: the listener module 1908 may completely parse out the name into smaller pieces of useable data; it extracts and validates the header; it extracts and validates the footer; it inserts one row into a FileMeta table, which also has a duplicate check on the file's name. After each of the above-mentioned steps, the listener module 1908 early exits via SRR if there are one or more errors in the transaction.

Next, the listener module 1908 parses the entirety of the file and tries to put it onto a Gateway Kafka topic module 1916 for the adjudication module 1920 to consume. The listener module 1908 may read the file one line at a time to extract each record. If it successfully transforms a record into an object, it then puts the object onto a Kafka topic. When a record cannot be converted to an object, the listener module 1908 may input an entry into a MemberErrorTransaction table, deeming that record as corrupt.

The transformation of transaction records into objects may be performed by the listener module 1908 using a J2C bean conversion (e.g., algorithm). Metadata on how to convert the line (transaction record string) into an object may be stored in a class, which contains getter and setter methods on how to extract substrings from the line using starting and ending character offsets for each attribute. For example, an eligibility group attribute value is 18 characters long and starts from character 11 and ends at 29. An example of the final data schema/structure that is created for sending to the Kafka topic module 1916 illustrated in FIG. 22 in JavaScript® Object Notation (JSON) format for human readability.

When the listener module 1908 writes the transactions to the Kafka topic module 1916, it does so asynchronously. This may be done so new records do not have to wait for the previous record to complete sending. When the listener module 1908 writes onto the Kafka topic module 1916, it includes a topic composite key (e.g., including Eligibility Group, Payment Type, Member Id, Person Number, and UPC code) to ensure that transactions that have the same member and universal product code (UPC) go to the same partition and therefore are read in sequence. This may help ensure that any updates on the same member and UPC are sent in an order to the same partition and not sent to a parallel partition to avoid data getting updated/persisted out of chronological order. The listener module 1908 attempts to put the transactions onto the Kafka topic module 1916 a predetermined number of times, which may be configured. If the listener module 1908 fails the predetermined number of attempts, the listener module 1908 may write an entry into the MemberErrorTransaction table.

While writing to the Kafka topic module 1916, the listener module 1908 keeps track of the total number lines processed, the total number of successful transformations, and the total number failed transformations. When there are zero total transactions in the file, the listener module 1908 indicates an error and ends the process with an SRR. When there are zero successful transactions, the listener module 1908 makes an entry into the VendorFileError table, and it updates the row it created in the VendorFileStorage table with a status of "FAILED" (a first status). When only some of the transactions successfully processed, the listener module 1908 updates the VendorFileStorage record with a status of "PARTIAL SUCCESS" (a second status). When all of the transactions are successfully transformed, the listener module 1908 updates the VendorFileStorage record with a status of "SUCCESS" (a third status).

Regardless of what happened over the course of processing the file, the listener module 1908 deletes the file from local memory once complete (e.g., setting the status). The listener module 1908 can also send a command to the SFTP server of the MFT gateway module 1904 and delete the file from the MFT gateway module 1904 as well. This feature may be configured to be ON or OFF.

When the listener module 1908 tries to create or update rows in the database, it can try up to the predetermined number of times, as discussed above. This retrying may only done in the case of a TransientDataAccessException, which is an exception that is made when the database cannot be connected to.

Kafka topics are messaging queues where source systems can publish messages and subscribers of those topics can read the messages. The concept of a messaging queue takes away the difficulty of two modules establishing a real-time direct connection with each other and at the same time allows data to be shared. The Kafka topic module 1916 may include a centralized Kafka infrastructure so that different teams can focus on development instead of administrating Kafka and its hardware.

The transaction processing module 180 includes a Kafka topic where the listener module 1908 posts individual transactions for the adjudication module 1920 to pick up. The Kafka topic may have 32 partitions, which allows for fast, parallel processing. The listener module 1908 may use 32 producer threads to write messages to the 32 partitions, and the adjudication module 1920 may uses 32 consumer threads to read the messages from the 32 partitions.

Once the transactions from the listener module 1908 reach the Kafka topic module 1916, they are ready to be read by adjudication module 1920. The adjudication module 1920 also exposes a HTTP REST API endpoint to directly ingest a claim from vendors that transmit transactions via the HTTP interface. Both channels to the adjudication module 1920, whether via the Kafka topic module 1916 or the HTTP interface, have transactions in a similar data structure with the Kafka transactions carrying a little bit more metadata for the file the transaction belongs to. A data structure comparison is provided below. The following transaction schemas are accepted by the adjudication module 1920—the Kafka transaction data structure has been illustrated above also, since its origin is from the listener module 1908.

| Kafka Transaction Data Structure | HTTPs REST API Request Data Structure |
|---|---|
| { | { |
| "dhfMemTransactionId": | "claimId": |
| "header":{ | "timestamp": |
| "date": | "vendorId": |
| "time": | "member":{ |
| "vendorFileId": | "id": |
| "vendorFileName": | "firstName": |
| "dhfVendorFileId": | "lastName": |

| Kafka Transaction Data Structure | HTTPs REST API Request Data Structure |
|---|---|
| "vendorId": | "patientAgn": |
| "vendorName": | "carrierId": |
| }, | "eligibilityGroup": |
| "transaction":{ | "dateOfBirth": |
| "carrierId": | "personNumber": |
| "eligGroup": | "contract": |
| "paymentType": | "patientId": |
| "unitCount": | }, |
| "memberId": | "order":{ |
| "personNum": | "upc": |
| "dob": | "upcQualifier": |
| "activationCode": | "paymentType": |
| "upcQual": | "activationCode": |
| "upc": | "unitCount": |
| "firstName": | "dateOfService": |
| "lastName": | } |
| "patientAgn": | |
| "contract": | |
| "claimId": | } |
| "dateOfService": | |
| "recordNumber": | |
| "vendMemTimestamp": | |
| "vendPatientId" | |
| } | |
| } | |

As illustrated, each Kafka transaction for a member (which are included in batch files) includes a DHF member transaction identifier (dhfMemTransactionId) and also includes a header portion including a date, a time, a vendor file identifier (vendorFileId—specified by the vendor), a vendor file name (vendorFileName), a DHF vendor file identifier (dhfVendorFileId-corresponding to the vendor file identifier and specified by the system described herein), a vendor identifier (vendorId) and a vendor name (vendorName). Each Kafka transaction for a member also includes a transaction portion including a carrier identifier (carrierId), an eligibility group (eligGroup), a payment type (paymentType), a unit count (unitCount), a member identifier (memberId), a person number (personNum), a date of birth (dob) of the member, an activation code (activation Code), a universal pricing code (UPC) qualifier (upcQual), a UPC, a first name (firstName) of the member, a last name (lastName) of the member, a patient AGN field, a contract, a claim identifier (claimId), a date of service (dateOfService), a record number (recordNumber), a vendor member timestamp (vendMemTimestamp), and a vendor patient identifier (vendorPatientId). Each transaction received via the REST API includes a different data structure than the above and one or more different fields than the above. For example, each transaction for a member received (individually) via the REST API includes a claim identifier, a timestamp, and a vendor identifier. Each transaction received via the REST API also includes a member portion including an identifier of the member, a first name of the member, a last name of the member, a patient AGN, a carrier identifier (carrierID), an eligibility group (eligibilityGroup), a date of birth of the member, a person number of the member, a contract of the member, and a patient identifier (patientId) of the member. Each transaction received via the REST API also includes an order portion including a UPC, a UPC qualifier (upcQualifier, a payment type (paymentType) for the order, an activation code for the order, a unit count for the order, and a date of service of the order.

The adjudication module 1920 may include a Java® application hosted on one or more servers. The adjudication module 1920 may include the Java 8® programming language coding, have the Spring® software development framework, and establishes connectivity with Kafka messaging queue and Postgres database, and expose HTTPs REST APIs over the Internet. This adjudication module 1920 consumes data in real time and responds within a predetermined period, such as less than 10 milliseconds.

The response for an HTTP API request is sent back within the predetermined period, but for the transactions that were extracted from vendor files and streamed to the Kafka topic module 1916 may be sent later. for example, their response may be sent at the end of the day in a summary feedback report. Summary feedback reports are discussed further below. An example of the request/response structure of the HTTP API for claim ingestion is as follows.

```
POST            https://api.XXX.io/dhf/v1/adjudication/claims/
Request
Endpoint
Request         {
Data               "claimId":
Structure          "timestamp":
                   "vendorId":
                   "member":{
                     "id":
                     "firstName":
                     "lastName":
                     "patientAgn":
                     "carrierId":
                     "eligibilityGroup":
                     "dateOfBirth":
                     "personNumber":
                     "contract":
                     "patientId":
                   },
                   "order":{
                     "upc":
                     "upcQualifier":
                     "paymentType":
                     "activationCode":
                     "unitCount":
                     "dateOfService":
                   }
                }
Response        {
Data               "dhfTransactionId": "",
Structure          "claimId": "",
                   "status": "",
                   "description": "",
                   "newRequestWaitTime": "",
                   "errors" ["", ""]
                }
```

As the transaction processing module 1804 may operate on an HTTP POST method there will be corresponding HTTP Response codes for different scenarios, which are described below. The description field may include some details for any erroneous scenarios. The errors section will specify the code which corresponds to an error description from the above-mentioned sections Response Code 200: This indicates transaction accepted.
Response Code 202: This indicates that a timeout occurred during processing the transaction.
Response Code 403: This indicates transaction is duplicate or rejected.

Response Code 500: Internal server error.
Response Code 503: Retry later. In this case the field "newRequestWaitTime" in the response will indicate the wait time before retrying the transaction.

Once the transactions are ingested by the adjudication module 1920, they are transformed into local objects. If the transactions don't meet the predefined data structure, the transformation fails and an appropriate error code is stored against it (in association with it) in the database.

If the transformation passes, then the field level validations by the adjudication module 1920 begin. With an exception of one or more fields, most fields have to pass one or more of the following validations:

required fields
missing fields
data-type check
parse-able dates
special character check
allowed payment type values Failure of some of these validations may not lead to a rejection, but instead the adjudication module 1920 may store a safe-proceed warning code against the transaction. For example, "claimId" from the vendor may not be a mandatory field, but if it's missing, the adjudication module 1920 may add a safe-proceed warning code against that transaction. However, some validation failures will lead to a rejection by the adjudication module, such as when it's a hard error like missing required fields like "carrierId".

Date of service may be the date when the member used the product and it is sent as part of the transaction from the vendor. There may be a business requirement to not entertain transactions that are older than a predetermined period, such as more than 2 years. The adjudication module 1920 may ensure that each transaction's date of service is not older than the predetermined period (e.g., 2 years)—otherwise the adjudication module 1920 may store a reject error code against the transaction.

The adjudication module 1920 may consider a transaction to be a duplicate when there is already a transaction in a Life Cycle table for the same member, group, person, date of service, payment type, and upc with adjudication status=ACCEPT (e.g., a first adjudication status). Duplicate claim check logic used by the adjudication module 1920 may not apply to previously persisted claims that with the status of REJECT or FAILED (e.g., second and third adjudication statuses, respectively). This logic gives another chance to previously rejected/failed transactions to be corrected. If the adjudication module 1920 finds a transaction to be duplicate, the adjudication module 1920 assigns an appropriate error code and sets the transaction status=DUPLICATE (a fourth adjudication status).

The adjudication module 1920 may call entity APIs sequentially and concurrently to collect their response and determine transaction eligibility. The adjudication module 1920 uses a membership API in real-time to check member eligibility for a transaction. The membership API may be a HTTPs REST GET call, and the following are examples of the request and response structures:

```
GET         https://api.XXX.io/v3-
Request     candidate/memberships/member?membershipId=<memberId>&groupId=<groupId>&personNumber=
            <personNo>&profileType=<profileType>
Response    [
              {
                "relativeId": "2da77296-f840-4e48-8da6-cc666636d573",
                "parentResourceId": "75377769-24a5-45a9-97ff-164d86376ab3",
```

```
    "personResourceId": "9884fbc4-818d-4629-b2bc-1934eb97c00d",
    "links": [
      {
        "rel": "parent",
        "href": "v3/memberships/75377769-24a5-45a9-97ff-164d86376ab3"
      },
      {
        "rel": "self",
        "href": "v3/memberships/75377769-24a5-45a9-97ff-164d86376ab3/member/2da77296-f840-4e48-8da6-cc666636d573"
      },
      {
        "rel": "person",
        "href": "/persons/9884fbc4-818d-4629-b2bc-1934eb97c00d"
      }
    ],
    "address": {
      "streetAddress": [
        "415 5TH ST"
      ],
      "postalCode": "38449-9998",
      "city": "ADAMS",
      "state": {
        "code": "TN"
      }
    },
    "agnId": 212660691,
    "birthDate": "1975-04-01",
    "name": {
      "first": "KIERRA",
      "middle": "J",
      "last": "DABROWSKI"
    },
    "personNumber": "001",
    "ssn": "516817470",
    "groupSourceCode": "P",
    "eligibilityStatusList": [
      {
        "effectiveDate": "2017-01-01",
        "eligibilityStatus": "Active"
      }
    ],
    "overallEligibilityStatus": "Active",
    "card": { },
    "relationship": {
      "code": "1"
    },
    "gender": {
      "code": "2",
      "value": "Female"
    },
    "selectedInd": "Yes",
    "coordinationOfBenefits": [
      {
        "effectiveDate": "2017-01-01",
        "paymentLevel": {
          "code": "1",
          "value": "Primary Payer"
        }
      }
    ],
    "clientMembershipId": "917298883",
    "confidentialIndicator": false
  }
]
```

The member eligibility check may be based on date of service of a transaction being in between a membership effectiveDate field and a expiryDate field of the member or the date of service having the month and year between a effectiveDate field and an expiryDate field.

The adjudication module 1920 may call a product entity API every predetermined period (e.g., every 24 hours) and cache the response in an in-memory cache within the adjudication module 1920. This cached data tells whether a product is active or not and provides default UPC attributes, such as billing-type, fee code, client fee, and vendor fee. This may also be a HTTPs REST GET call, and following are examples of the request and response structures:

| | |
|---|---|
| GET Request | https://api-qa.XXX.io/v2/products/clinical?optionName=DHF&optionValue=true |
| Response | ```
[
  {
    "links": [
      {
        "rel": "self",
        "href": "https://api-qa.XXX.io/v2/products/clinical/0b99aadc-2e5b-4ff3-8601-4a2f44ec39cd"
      },
      {
        "rel": "update",
        "href": "https://api-qa.XXX.io/v2/products/clinical"
      }
    ],
    "resourceId": "0b99aadc-2e5b-4ff3-8601-4a2f44ec39cd",
    "enterpriseId": "801",
    "sourceCode": "14",
    "name": "Cognitive Behavioral Therapy - Learn to Live",
    "description": "",
    "enrollmentType": "ClientManaged",
    "status": "Active",
    "options": [
      {
        "name": "vendor",
        "value": "true"
      },
      {
        "name": "hc360",
        "value": "true"
      },
      {
        "name": "DHF",
        "value": "true"
      },
      {
        "name": "standardFeeCode",
        "value": "D001"
      },
      {
        "name": "standardClientFee",
        "value": "0.15"
      },
      {
        "name": "standardBillingType",
        "value": "PPPM"
      {
    ],
    "effectiveDateTime": "2018-08-02,"
    "expirationDateTime": "3000-12-31",
    "billingAttributes": [
      [
        {
          "name": "upc",
          "value": "234567890001"
        },
        {
          "name": "feeCode",
          "value": "D001"
        },
        {
          "name": "clientFeeDollarAmount",
          "value": "0.15"
        },
        {
          "name": "vendorFeeDollarAmount",
          "value": "0.00"
        },
        {
          "name": "description",
          "value": "PPPM Fee"
        },
        {
          "name": "billingType",
          "value": "PPPM"
        }
      ]
    ]
  },
    "links": [
``` |

```
        {
          "rel": "self",
          "href": "https://api-qa.XXX.io/v2/products/clinical/c509f7c4-e366-4054-
8214-fa1b52999345"
        },
        {
          "rel": "update",
          "href": "https://api-qa.XXX.io/v2/products/clinical"
        }
      ],
      "resourceId": "c509f7c4-e366-4054-8214-fa1b52999345",
      "enterpriseId": "802",
      "sourceCode": "14",
      "name": "Cognitive Behavioral Therapy - Silvercloud",
      "description": "",
      "enrollmentType": "ClientManaged",
      "status": "Active",
      "options": [
        {
          "name": "vendor",
          "value": "true"
        },
        {
          "name": "hc360",
          "value": "true"
        },
        {
          "name": "DHF",
          "value": "true"
        },
        {
          "name": "standardBillingType",
          "value": "PMPM"
        },
        {
          "name": "standardClientFee",
          "value": "0.15"
        },
        {
          "name": "standardFeeCode",
          "value": "D001"
        }
      ],
      "effectiveDateTime": "2020-02-01",
      "expirationDateTime": "2999-12-31",
      "billingAttributes": [
        [
          {
            "name": "upc",
            "value": "00860003829745"
          },
          {
            "name": "feeCode",
            "value": "D001"
          },
          {
            "name": "clientFeeDollarAmount",
            "value": "0.15"
          },
          {
            "name": "vendorFeeDollarAmount",
            "value": "30.00"
          },
          {
            "name": "description",
            "value": "Silvercloud True Up"
          },
          {
            "name": "billingType",
            "value": "PMPM"
          }
        ],
        [
          {
            "name": "upc",
            "value": "00860003829738"
          },
          {
            "name": "feeCode",
```

```
            "value": "D001"
        },
        {
            "name": "clientFeeDollarAmount",
            "value": "0.15"
        },
        {
            "name": "vendorFeeDollarAmount",
            "value": "1.00"
        },
        {
            "name": "description",
            "value": "Silvercloud self guided"
        },
        {
            "name": "billingType",
            "value": "PMPM"
        }
      ]
    ]
  }
]
```

The product active check may be based on date of service of a transaction being in between a product effectiveDate field and an expiryDate field or the date of service having a month and year between an effectiveDate field and an expiryDate field.

The adjudication module 1920 may call a client enrollment API in real-time to check whether the client is enrolled in the product of the transaction or not and also extract some overridden attributes about the UPC, such as billing-type, fee code, client fee, and vendor fee. Only overridden UPC attributes may be extracted from here. Default UPC attributes may be extracted from a product entity API. This API may be called using a HTTPs REST GET call and following are examples of the request and response structures.

```
GET       https://api.XXX.io/v2/enrollments/client?carrier=<carr>&contract=<contr>&groupId=<group>&product
Request   ResourceId=<prodId>&upc=<upc>&billingAttributeName=upc&_include=BILLINGATTRIBUTE
Response  [
            {
              "links": [
                {
                  "rel": "self",
                  "href": "https://api-qa.XXX.io/v2/enrollments/client/calccd4f-963f-4ade-b46a-
                  8dfaa018236d"
                },
                {
                  "rel": "update",
                  "href": "https://api-qa.XXX.io/v2/enrollments/client"
                }
              ],
              "resourceId": "calccd4f-963f-4ade-b46a-8dfaa018236d",
              "customId": "c2d73fca-1b1d-4fe9-a008-e0eda2af6870",
              "product": {
                "resourceId": "c509f7c4-e366-4054-8214-fa1b52999345"
              },
              "clientHierarchy": {
                "type": "Standard",
                "levels": [
                  {
                    "type": "Group",
                    "id":"3",
                    "inclusions": {
                      "values": [
                        "DALCATHAACT"
                      ]
                    },
                    "parentId": "2",
                    "userSpecified": true
                  },
                  {
                    "type": "Carrier",
                    "id": "1",
                    "inclusions": {
                      "values": [
                        "1671"
                      ]
                    },
                    "parentId": "",
                    "userSpecified": true
```

```
    },
    {
      "type": "Contract",
      "id": "2",
      "inclusions": {
        "values": [
          "00175312"
        ]
      },
      "parentId": "1",
      "userSpecified": true
    }
  ]
},
"effectiveDateTime": "2020-02-10",
"expirationDateTime": "2020-08-25",
"status": "Enrolled",
"billingAttributes": [
  [
    {
      "name": "upc",
      "value": "00860003829745"
    },
    {
      "name": "feeCode",
      "value": "D001"
    },
    {
      "name": "clientFeeDollarAmount",
      "value": "0.20"
    },
    {
      "name": "vendorFeeDollarAmount",
      "value": "35.00"
    },
    {
      "name": "description",
      "value": "Silvercloud True Up"
    }
  ]
]
}
]
```

The client enrollment eligibility check is based on the date of service of a transaction being in between an effectiveDate field and an expiryDate field or the date of service having a month and year of between an effectiveDate field and an expiryDate field.

The adjudication module 1920 calls a patient enrollment entity API, such as in real time, to check whether a patient (member) is enrolled in the product of a transaction or not. This API may be called using a HTTPs REST GET call and following are examples of the request and response structures.

| GET Request | https://api.XXX.io/v2/enrollments/patient?membershipId=<memberId>&productResourceId=<prodId>&group=<group>&personNumber=<personNo> |
|---|---|
| Response | ```
[
  {
    "links": [
      {
        "rel": "self",
        "href": "https://api-qa.XXX.io/v2/enrollments/patient/6ca6fe2f-5661-4c56-b6cc-08743ecd22f6"
      },
      {
        "rel": "update",
        "href": "https://api-qa.XXX.io/v2/enrollments/patient"
      }
    ],
    "patientEnrollmentResourceId": "6ca6fe2f-5661-4c56-b6cc-08743ecd22f6",
    "productResourceId": "5f869b42-e56f-42a5-9c1f-ab0fc2feb8b5",
    "invitationCode": "40000000",
    "effectiveDateTime": "2021-01-01",
    "expirationDateTime": "3000-12-31",
    "enrollmentStatus": "Enrolled",
    "membershipId": "000008729585",
    "personNumber": "001",
    "personResourceId": "9884fbc4-818d-4629-b2bc-1934eb97c00d",
    "membershipResourceId": "75377769-24a5-45a9-97ff-164d86376ab3",
``` |

```
    "personName": {
       "first": "KIERRA",
       "last": "DABROWSKI",
       "birthDate": "1975-04-01"
    },
    "personAttributes": [
       {
          "name": "groupId",
          "value": "FTLVCDH7"
       },
       {
          "name": "drug1",
          "value": "testDrug1"
       },
       {
          "name": "drug2",
          "value": "testDrug2"
       }
    ]
  }
]
```

The patient enrollment eligibility check may be based on the date of service of a transaction being in between an effectiveDate field and an expiryDate field or the date of service having the month and year between an effectiveDate field and an expiryDate field.

The following pattern may be used by the adjudication module 1920 to handle entities:

Entity Adapter: The adapter exposes method to call an entity API using a search criteria of parameters. This adapter returns the response object.

Response Validator: The response validator runs logic on the response object to accumulate error/safe-proceed warning codes Data Collector: Data collectors for each entity combine the information collected from the entity API response and Errors accumulated during validations The transaction object gets enriched with information from data collectors by the adjudication module and thereby reaches a final state to be persisted.

The sequential and concurrent calling of entities APIs increases processing speed of transactions and vendor files. Entities APIs that depend on data from another entities API are called sequentially, and entities APIs that do not depend on data from any other entities API are called concurrently. This decreases processing time and increases the speed at which transactions and vendor files are processed. The calling of the entities APIs is done by the adjudication module 1920, as described above. In various implementations, the member and product entities APIs are called in parallel and only when the product call succeeds, then the client and patient entities APIs are called in parallel.

Based on the validations and adjudication, the adjudication module 1920 accumulates a list of errors and safe-proceed warnings for each transaction, which are then persisted in an error table referencing the original transaction in the life cycle table. The codes (errors and warnings) represent possible issues with each transaction based on logic and are reported back to the vendors either via an HTTP API response or in the summary feedback report for vendors who use files for transaction submission.

Each validation and adjudication logic has a digital health formulary (DHF) code (e.g. DHF-002, DHF-002) assigned, and some of the DHF codes map to national council for prescription drug programs (NCPDP) codes. In the case where a 1:1 mapping exists between a DHF error code and a NCPDP error code, the vendors receive the NCPDP error code. In the case where no NCPDP code maps to a DHF code, vendors are returned the DHF code. The meaning of the DHF codes and their descriptions are shared with the vendors.

Following are Examples of Error Codes and Logic that Drives them

| Field Name/ Scenario | Required/ Optional | Format | Validation | Rejection (Y/N) | DHF Codes | NCPDP/ Mapped Codes | Description |
|---|---|---|---|---|---|---|---|
| claimId | Optional | Alpha-numeric | If this field is missing or invalid, we will assign an error code/message but the transaction will not be rejected. If this field is present this will part of the response. | N | DHF-016 | 03 | Member Transaction ID is missing or invalid. |
| timestamp | Optional | yyyy-MM-dd-HH.mm.ss SSSSSS | If this field is missing or invalid the transaction won't be rejected but an appropriate error code/message will be returned and | N | DHF-042 | DHF-042 | Missing or Invalid Process Timestamp |

-continued

| Field Name/ Scenario | Required/ Optional | Format | Validation | Rejection (Y/N) | DHF Codes | NCPDP/ Mapped Codes | Description |
|---|---|---|---|---|---|---|---|
| | | | the value will be set to default timestamp. | | | | |
| vendorId | Required | Alpha-numeric | If this field is missing or invalid an error will be sent and the transaction will be rejected. | Y | DHF-013 | 05 | Vendor Id is missing or invalid. |
| Member -> id | Required | Number | If this field is missing or invalid the member transaction will be rejected. | Y | DHF-019 | 07 | Member ID is missing or invalid. |
| | | | If the member is found to be not eligible in the operators system then transaction will be rejected. | Y | DHF-024 | 65 | Member is not eligible. |
| | | | If combination of Member/Group/PersonNo. is not found in operators system the then the transaction will be rejected. | Y | DHF-023 | 52 | Member is not available in system. |
| Member -> firstName | Optional | Alpha | This field will be compared with that of operators system. If they don't match, we will override with operators value. However, if it's missing or invalid, we'll still return an error code/message but Transaction will not be rejected. | N | DHF-001 | CA | First Name is missing or invalid. |
| Member -> lastName | Optional | Alpha | This field will be compared with that of operators system. If they don't match, we will override with operators value. However, if it's missing or invalid, we'll still return an error code/message but Transaction will not be rejected. | N | DHF-002 | CB | Last Name is missing or invalid. |
| Member -> patientAgn | Optional | Alpha-numeric | If this field is missing or invalid, we will store the relevant code but won't reject the transaction. This field will also be compared with operators system. If | N | MEM-AGN | CY | Patient AGN supplied does not match with AGN returned from membership entity |
| | | | the values don't match, an error will be returned but the transaction will not be rejected. | | DHF-009 | CY | Patient AGN is missing or invalid |
| Member -> carrierId | Required | Alpha-numeric | If this field is missing or invalid, the member transaction will be rejected. | Y | DHF-007 | CR | Carrier id is missing or invalid. |

-continued

| Field Name/ Scenario | Required/ Optional | Format | Validation | Rejection (Y/N) | DHF Codes | NCPDP/ Mapped Codes | Description |
|---|---|---|---|---|---|---|---|
| Member -> eligibility Group | Required | Alpha-numeric | If this field is missing or invalid the member transaction will be rejected. | Y | DHF-018 | 06 | Group ID is missing or invalid |
| Member -> dateOfBirth | Required | YYYY-MM-DD (Alpha-numeric) | If DOB is missing or invalid or doesn't match the DOB from operators system then the member transaction will be rejected. | Y | DHF-021 | 09 | Date of Birth is missing or invalid |
| Member -> personNumber | Required | Number | If this field s missing or invalid the member transaction willbe rejected. | Y | DHF-020 | 08 | Person No. is missing or invalid |
| Member -> contract | Required | Alpha-numeric | If this field is missing or invalid, the transaction will be rejected. | Y | DHF-040 | DHF-040 | Contract is missing or invalid |
| Member -> patientid | Optional | Alpha-numeric | If this field is missing the transaction will not be rejected. | N | | N/A | N/A |
| Order -> upc | Required | Alpha-numeric | If this field is missing or invalid then the transaction will be rejected and an appropriate error code/message will be returned. | Y | DHF-022 | 21 | UPC is missing or invalid |
| Order -> upcQualifier | Optional | Alpha-numeric | If this field is missing or invalid or other than 01 a default code 01 will be assigned and the transaction will not be rejected. | N | N/A | N/A | N/A |
| Order -> paymentType | Required | Alpha | If this field is missing or invalid the member transaction will be rejected. Any value other than "D or C" will be rejected. | Y | DHF-033 | 3A | Payment Type is missing or invalid |
| Order -> activation Code | Required | Alpha-numeric | If this field is missing or invalid we assign the code and carry on with transaction. The transaction will not be rejected. | N | DHF-039 | CW | Activation Code is missing or invalid. |
| Order -> unitCount | Required | Number | If this field is missing or invalid the member transaction will be rejected. Value other than 1 to 12 will be rejected. | Y | DHF-012 | E7 | Unit Count is missing or invalid |
| Order -> dateOfService | Required | YYYY-MM-DD (Alpha-numeric) | If DOS from member transaction is before coverage effective date in operators system then the transaction will be rejected unless the month and year of DOS is same that of coverage effective date of operators system. | Y | DHF-025 | 67 | Date of Service is before coverage effective date |

| Field Name/ Scenario | Required/ Optional | Format | Validation | Rejection (Y/N) | DHF Codes | NCPDP/ Mapped Codes | Description |
|---|---|---|---|---|---|---|---|
| | | | If DOS from member transaction is after termination date in operators system then the transaction will be rejected. | Y | DHF-026 | 69 | Date of Service is after coverage expired. |
| | | | Any transaction's DOS that is older than 2 years from NOW is too old and therefore we assign this code, and do a hard rejection. | Y | DHF-029 | 81 | Date of Service is too old |
| | | | If DOS on member transaction is of a future date of a current billing cycle, the transaction will be rejected. | Y | DHF-030 | 82 | Date of Service is post-dated. |
| | | | If the Date of Service is missing or in invalid format the member transaction will be rejected. | Y | DHF-038 | 15 | Date of Service is missing or invalid. |
| Member/ Patient is not enrolled into product | Required | N/A | If the member is not enrolled into the product then it is a hard reject. | Y | DHF-051 | DHF-051 | Patient is not enrolled. |
| Client is not enrolled into product | Required | N/A | If the client is not enrolled into the product then it is a hard reject. | Y | DHF-052 | DHF-052 | Client is not enrolled. |
| Duplicate Transaction | Required | N/A | If any accepted transaction is sent again, it will be marked as DUPLICATE and rejected. | Y | DHF-041 | 83 | Transaction is duplicate. |
| Internal System Errors or Failures | Required | N/A | If any timeouts or unexpected errors occur in any operators peripheral system/infrastructure while adjudicating a transaction, such transactions will be FAILED. To vendors only one error code will be sent, "99" – "Host Processing Error", but internally DHF will store a specific error code that helps in troubleshooting | Y | Several codes are mapped to 99 for various minute data/ system issues. | 99 | Host Processing Error |
| Inactive/ Invalid UPC | Required | N/A | If UPC is inactive, invalid, or not found in operators system then the transaction will be rejected. | Y | DHF-028 | 70 | Product is not found, or active or covered |

-continued

| Field Name/ Scenario | Required/ Optional | Format | Validation | Rejection (Y/N) | DHF Codes | NCPDP/ Mapped Codes | Description |
|---|---|---|---|---|---|---|---|
| Multiple transactions for same Member/ Group/ PersonNo/ UPC with same month and year date-of-service | N/A | N/A | If multiple transactions are submitted for the same Member/Group/ PersonNo/UPC using a date-of-service of same month and year then DHF will assign a safe-proceed warning code. This is because member's usage of a product in a month is usually represented by one transaction. Such transactions won't be rejected but will be kept track of. | N | DHF-064 | DHF-064 | Duplicate member/ product combination submitted for the same month |
| Message Transformation Failure | N/A | N/A | If a transaction fails to get transformed into a local object within the DHF system | Y | DHF-000 | DHF-000 | Transformation Failure |
| Reversals | N/A | N/A | Reversal transactions are meant to offset a previous transaction that was sent in error by the vendor. There are a few reversal specific validations that have to be done, which are called our here, | Y | DHF-058 | DHF-058 | Could not look up original transaction against the reversal-(C beforeD) |
| | | | | N | DHF-059 | DHF-059 | Unit count value on reversal does not match with the original transaction |
| | | | | N | DHF-060 | DHF-060 | Member's First Name on reversal does not match with the original transaction |
| | | | | N | DHF-061 | DHF-061 | Member's Last Name on reversal does not match with the original transaction |
| | | | | N | DHF-062 | DHF-062 | Member's date of birth on reversal does not match with the original transaction |
| | | | | N | DHF-063 | DHF-063 | Activation code on reversal does not match with the original transaction |

The transaction object within the adjudication module 1920 carries all of the information from the original Kafka topic module 1916 or the HTTP API message and data collected from the entities APIs and errors accumulated over the course of its processing. Once the processing is complete, then a AdjudicationStorageService component/class within the adjudication module 1920 uses this transaction object to convert it into Life Cycle table and Error table data-transfer-objects and persists them into the database tables.

The AdjudicationStorageService component/class makes a decision on determining the final status of the transaction (e.g., whether the transaction is Accepted/Rejected/Failed/Duplicate) and the billing and remittance statuses using the error codes. This decision (adjudication) by the adjudication module 1920 may be made as follows:

Final adjudication status is set to 'DUPLICATE' if error list contains an error with code 'DUPLICATE'

Final status adjudication status is set to 'REJECT' if the error list contains at least one error with code REJECT This means that claim is a legitimate REJECT and there could be multiple reasons such as field level reject, or entity response validation reject, such as member not eligible, etc.

Status is set to 'FAILED' if it find there are errors with FAILURE code.
Aa transaction is 'FAILED' may mean that the transaction could not be processed because of one or more (e.g., internal) issues or data errors Status is set to ACCEPT' if it does not fall into the above conditions and only in this case billing status is set to 'ReadyForBilling' and remittance status is set to 'ReadyForRemittance'

The adjudication module 1920 may use Caffeine Cache to store all of the products returned by the Product Entity API may not be present. This may be done, for example, to improve write performance and adhere to the requirement to persist all transactions like a historical log.\

The exposed APIs used by the adjudication module 1920 for claim ingestion and status check may be protected resources using OAUTH 2.0 and an internal server. All entity APIs that the adjudication module 1920 calls may also be OAUTH 2.0 protected resources leveraging the internal server. All calls may be encrypted using transport layer security (TLS) 1.2 or another suitable type of encryption.

Other components like the Kafka topic module 1916 and the Postgres database are hosted by internal encryption modules that provide data encryption at-rest and require certificates for establishing connection and encrypting and decrypting data.

The adjudication module 1920 exposes a claim status check endpoint. This endpoint can be called by a vendor for checking the status of a previously submitted transaction by passing a dhfTransactionId (UUID) as a parameter. dhfTransactionIds are sent back on the response against each claim submission so the vendor will possess this ID before invoking the claim status endpoint. This ID is generated by the transaction processing module 1808. Below are examples of the request and response.

| | |
|---|---|
| GET Request Endpoint | https://api.XXX.io/dhf/v1/adjudication/status?dhfTransactionId=<dhfTransactionId> |
| Response Data Structure | { claimId: "", dhfTransactionId: "", status: "", description: "", newRequestWaitTime:, errors: [error code, error code] } | during the startup. This cache uses a hashmap (Map<String, ClinicalProduct>) for storing the products by UPC. In this sense, the UPC acts as the key and the value against it is an individual product object extracted from the Product Entity API response. Every transaction has a UPC in it and to validate the transaction, we call the cache using the UPC and get the all the attributes from the product object. This cache may be an in-memory cache inside the adjudication module 1920. It may be set to expire every predetermined period (e.g., every 24 hours) and on restart it may clear the cache and reload it by calling the Product Entity API. Caffeine cache is a high performance caching library.

Redis, by Redis Labs, is an external caching service provided via the Internet for data storage outside of application memory. Redis is an open source, in-memory data structure store, used as a database, cache, and message broker. Redis provides data structures such as strings, hashes, lists, sets, sorted sets with range queries, bitmaps, hyperloglogs, geospatial indexes, and streams.

The adjudication module 1920 may use Redis to acquire a lock on a transaction using a key made of attributes that uniquely identify a transaction. This helps to put two or more transactions which were duplicate and were received at the same instance in a sequence so that all of them do not get inserted into the Life Cycle table-because the Life Cycle table is queried for duplicates before data is inserted and if no duplicate exists at the time of parallel queries then all duplicates will get inserted as Accepted transactions. Unique constraints on a transaction's uniquely identifying columns When an HTTP request is received for the claims endpoint from a vendor, a timer is started to return a response. Vendors may be requested to set a timeout of 30 seconds. The period for the transaction processing module 1808 returning a response may be shorter than the timeout period of vendors and may be configured, such as to 5 seconds or another suitable period. If the transaction processing module 1808 has not responded back to the vendor within the period, the transaction processing module 1808 may return a "checkStatusLater" response which is carrying the dhfTransactionId. This ensures that the vendors do not have to timeout while calling our APIs and neither have to ever wait beyond 5 seconds if in the transaction processing module 1808 suffering from one or more errors and/or performance degradation. The vendors can use the dhfTransactionId to check back on the final status of the transaction at a later time.

In various implementations, the adjudication module 1920 may fail a transaction early, such as to protect performance. The adjudication module 1920 may, when a transaction has encountered an error code which causes a hard reject, immediately terminate all subsequent processing for that transaction and persist it in the Life Cycle and Error tables and respond back to vendor.

In various implementations, the adjudication module 1920 may use a retry template, which is a reusable piece of code that is leveraged for all external calls including API calls and database queries, such as to make the system more resilient to intermittent failures. The retry template code allows for configurable number of retries to APIs or databases queries based upon a policy, such as a certain exception and also allows for configurable time gap between each retry.

Regarding parallel processing and thread/memory management, the adjudication module 1920 may be configured based on the principle of non-blocking code leveraging the Java 8® CompletableFuture API, which allows for multi-threaded processing resulting is speed from parallel processing. However, if more than a predetermined number of parallel requests coming in from the Kafka topic module 1916 or the HTTP API, too many threads may be used, which may cause thread starvation and/or a crash. To avoid this, the adjudication module 1920 may limit how many threads can be spun up for certain CompletableFuture processes using thread pool configuration using a TaskExecutor bean. The bean is passed as a parameter to certain CompletableFuture methods in order to maintain a balance between speed and memory.

After the adjudication module 1920 has completed all processing/adjudication for a transaction, the data is persisted in two tables—the Life Cycle and Error tables. The Life Cycle table has a single row against each transaction which includes all the original attributes, additional attributes collected from entities and adjudication statuses for billing, remittance and overall transaction. The Error table may have multiple rows referencing a single transaction and each of these rows represent a separate error/safe-proceed warning code.

If you join these two tables on dhfTransactionId, a more complete picture of the transaction and what were there specific validation and adjudication findings using the error codes can be obtained. The Life Cycle table is the source data for client billing, vendor invoicing, reporting, and the frontend MFT gateway module 1904.

A collation module 1924 may be a single instance application built using the Java 8® programming language and the Spring® software development framework. The collation module 1924 establishes connectivity with the Postgres database and the MFT gateway module 1904 (e.g., the SFTP server). The collation module 1924 collates billable transactions from the Life Cycle table and the Client Billing table and sends them to a billing module 1928. The billing module 1928 is the billing system that bills clients. The client Billing table is discussed hosts data from the billing flow and is discussed elsewhere in this application.

The collation module 1924 runs like a job at a scheduled time based on a configurable Cron expression which adheres to eastern standard time (EST) or another suitable time. It may run, for example, the 1$^{st}$ (date) of every month, such as to adhere to a monthly billing cycle. At the scheduled time, the collation module 1924 queries all transactions that were inserted in the past month that are in 'ReadyForBilling' status in the Life Cycle and Client Billing tables and sets them to 'CollationInProgress' status. It also updates a last-Updated AppName field and lastUpdatedTimestamp field in both of the tables.

The collation module 1924 transforms all of the 'Collation InProgress' records into a string using an IBS prescribed copybook metadata and are written as a row to a fixed length file. The collation module 1924 stores the file in memory as a temporary file until all records are transformed and written to the file. During this processing if any of the records fail to transform, the collation module 1924 updates their status to "TransformationFailure" in the respective table. The file has a header and a trailer row which are created using IBS prescribed copybook metadata.

Once the collation module 1924 completes the file, the collation module 1924 sends the file to the billing module 1928 (e.g., an SFTP server). Metadata related to the file such as bill date, billing total, and billing record count is stored in IBS Billing Meta table, such as for quick reference.

Once the file is successfully sent to the billing module 129 via SFTP, all the records in Life Cycle and Client Billing table with 'CollationInProgress' status are updated by the collation module 1924 to 'QueuedForBilling'.

A remittance module 2004 (FIG. 20A/20B) may be a single instance application built using the Java 8® programming language and the Spring® software development framework. The remittance module 2004 establishes connectivity with the Postgres database. The remittance module 2004 collates all transactions in the Life Cycle table that are in "ReadyForRemittance" status and converts them into an invoice.

The remittance module 2004 runs monthly against the last month's Life Cycle data and generates a PDF invoice on behalf of each vendor and emails the PDF invoice to the respective product owner. The data in the invoice includes UPC code, UPC Description, Payment Type (e.g., credit or debit), Quantity, Rate, Amount and other invoicing details, such as vendor address and product owner name. The address and product owner name and whom to email invoice to, such details may be retrieved by the remittance module 2004 from a vendor master table.

The remittance module 2004 calculates and aggregates the transaction data from the Life Cycle table and extracts the exact remittance amount on behalf of the vendor that needs to be paid to the vendor by the operator of the transaction processing module 1808. Each invoice may also stored in binary format by the remittance module 2004 in the vendor invoice table along with its metadata.

The report module 1912 may be a single instance application built using the Java 8® programming language and the Spring® software development framework. The report module 1912 establishes connectivity with the Postgres database and the MFT gateway module 1904 (e.g., the SFTP server). The report module 1912 sends back summary feedback report each day for transactions in the Life Cycle table which were submitted in the last 24 hours. The report module 1912 generates summary reports against vendor files that were submitted and also against HTTP API transactions that were submitted by vendors.

The report module 1912 is a scheduled job that is invoked using the configurable Cron expression.

The report module 1912 may generate reports for all vendor files for which feedback is not sent. The report module 1912 checks the Report_Status column in File Meta table to verify if a feedback report was sent or not.

Or the report module 1912 can request a report for a specific vendor file by using configurable properties.

Each of the report files generated by the report module 1912 is persisted in the vendor_report_file_storage table with the dhfFileId as the unique-key. This can be used as a way to go back and check what was sent to the vendor for that report. A summary feedback files generated against vendor files and vendor transactions may have a predetermined naming convention. For example, The summary feedback file generated against vendor files may have the naming convention <vendorRoutingId>_<vendorFileName>_Summary Report.csv The summary feedback file generated against vendor transactions that come via HTTP API channel may have the naming convention <vendorRoutingId>_<vendorId>_<timestamp>_ Summary Report.csv.

The report module 1912 picks up all of the File Meta table records for which a report is still not generated and calls the prepareReportAndSftp method. A generateReportAndSftpOneVendorFile function picks up the specific File Meta table record for the given dhfFileId for which a report is required and calls a prepareReportAndSftp. For each File Meta record, the prepareReportAndSftp function obtains all the member error transactions, member life cycle transactions. If the counts match with the File Meta record, the report module 1912 acts, otherwise the report module 1912 will use the failure threshold check to see if report generation needs to continue. This check will be ignored if the call is for a single report generation.

For each of the life cycle transactions, the corresponding member error summary and error master tables are queried by the report module 1912 to populate the error codes based on the column dhfmtc_mem_tran_life_cycle.dhfmtc_completed_with_errors value. Each of the records will be populated with a status by the report module 1912.

The report module 1912 creates a .csv summary feedback file with the sections as detailed and the file will be sent to the MFT gateway module 1904 via SFTP. The report module 1912 will also store the generated file in database for future reference. Also the report module 1912 updates the File Meta table with the status of the report generation.

Mapping of vendor to routing id may be maintained in the configuration settings, such as using the following key/value pair construct {VendorA: 'PROP4325', VendorB: 'SDF233', VendorC: 'SDF987'}. If no mapping is found then a default value may be returned, such as to avoid failing report generation.

When the report module 1912 tries to create or update rows in the database, it may try a predetermined number of times. This retrying may only be for the case of a TransientDataAccessException, which is the exception that is thrown when the database will not connect. The report module 1912 may apply the same retry concept for file SFTP. This implementation may use the same retry template code referenced above.

Clients that enroll into products with PMPM billing type are not billed for individual product usage by its employees/ members, they are billed for the entire population count that the Client enrolls into a PMPM product. The enrolled population count is represented by Carrier, Contract, and Group combination. The role of the PMPM billing flow is to get all PMPM enrollments, fetch the price of the product(s), fetch the population counts against the enrollments, and multiply the counts with the product price and come up with the total billing amount against each enrollment. Once this process is complete, the enrollments with billing amount are sent to billing module 1928 for client billing.

The Client Enrollment entity is a module that maintains all of the data related to client enrollments into products. All of this data is stored in a nosql database and upon a change to any enrollment, an update message is published on the Enrollment Change Kafka topic. The billing facilitator module 1932 is subscribed as a consumer of this topic and it immediately receives the changed enrollment message.

```
key: {
   "messageVersion": "1",
   "header": {
      "operation": "INSERT",
      "transactionId": "3ef5e38e-8f7a-427b-913d-d2330cb2e708"
   },
   "payload": {
      "beforeData": null,
      "afterData": {
         "resourceId": "3ef5e38e-8f7a-427b-913d-d2330cb2e701",
         "customId": "994b0bbc-6e58-49d1-aa6a-79614269d2gt",
         "product": {
            "resourceId": "c509f7c4-e366-4054-8214-falb52999345",
            "options": [
               {
                  "name": "standardBillingType",
                  "value": "PMPM"
               },
               {
                  "name": "standardClientFee",
                  "value": "19.00"
               },
               {
                  "name": "standardFeeCode",
                  "value": "D211"
               }
            ]
         },
         "clientHierarchy": {
            "type": "Standard",
            "orgId": "10037",
            "levels": [
               {
                  "type": "Carrier",
                  "id ": "1",
                  "inclusions": {
                     "values": [
                        "0037"
                     ]
                  },
                  "userSpecified": true
               },
               {
                  "type": "Contract",
                  "id ": "2",
                  "inclusions": {
                     "values": [
                        "00000077"
                     ]
                  },
                  "parentId": "1",
                  "userSpecified": true
               },
               {
                  "type": "Group",
                  "id ": "3 "
                  "inclusions": {
                     "values": [
                        "64 SW050"
                     ]
                  },
                  "parentId": "2",
                  "userSpecified": true
               }
            ]
         },
         "effectiveDateTime": "2017-07-02",
         "expirationDateTime": "2017-07-02",
         "status": "Enrolled",
         "billmgAttributes": [
            [
               {
                  "name": "upc",
                  "value": "00860003829745"
               },
               {
                  "name": "feeCode",
                  "value": "D001"
               },
               {
                  "name": "clientFeeDollarAmount",
                  "value": "15.00"
```

-continued

```
    },
    {
      "name": "vendorFeeDollarAmount",
      "value": "15.00"
    },
    {
      "name": "description",
      "value": "Silvercloud True Up"
    },
    {
      "name": "billingType",
      "value": "PPPM"
    }
      ]
     }
    }
   }
}
```

A billing facilitator module 1932 may be a multi-instance application built using the Java 8® programming language and the Spring® software development framework. The billing facilitator module 1932 establishes connectivity with the Postgres database, a Kafka messaging queue, and the HTTP APIs. The billing facilitator module 1932 starts consuming enrollment messages via a change topic, validates and decides which ones are for per member per month (PMPM) billing and saves such enrollments for further processing. All other type of enrollments may be ignored by the billing facilitator module 1932. An incoming message may be considered valid by the billing facilitator module 1932 for PMPM billing if:

mapped to a DHF Clinical Product (UUID mapping) and standardBillingType is PMPM

StandardBillingType is set at product level and is extracted by the billing facilitator module 1932 either from standard price overrides (from the client enrollment message) or standard price defaults (from clinical product). The Clinical Product data is retrieved from a Product Entity API call and is cached in memory cached called Caffeine. This is the same implementation as in the adjudication module 1920. In this case, however, the hashmap values differ to cater to the billing facilitator module 1932 use case.

If the client enrollment messages fail validations by the billing facilitator module 1932, multiple error codes can be assigned by the billing facilitator module 1932 to the messages and the messages are stored in dhfeh_enrollment_history table and errors are stored in dhfcbe_client_billing_error table. Examples are provided below.

| Field | Error Code | Error Message | Error Type | Severity |
|---|---|---|---|---|
| Missing Header | DHF-201 | Invalid Header - null header | Warning | Safe Proceed |
| Header-Null Kafka Transaction Id | DHF-202 | Invalid Header - No transaction Id | Warning | Safe Proceed |
| Header-Null Operation | DHF-203 | Invalid Header - Operation is not specified | Warning | Safe Proceed |
| payload | DHF-204 | Invalid payload - null payload | Error | FAILED |
| afterData | DHF-205 | Invalid payload - afterData cannot be null for Insert/Update operation | Error | FAILED |
| Enrollment Resource Id | DHF-206 | Invalid Enrollment Resource Id | Error | FAILED |
| Enrollment Effective Date | DHF-207 | Invalid Enrollment Effective Date | Error | FAILED |
| Enrollment Expiration Date | DHF-208 | Invalid Enrollment Expiration Date | Error | FAILED |
| Client Hierarchy | DHF-209 | Not a group level enrollment | Error | FAILED |
| Product | DHF-210 | Product cannot be null | Error | FAILED |
| Product Resource Id | DHF-211 | Invalid Product Resource Id | Error | FAILED |
| standardBillingType | DHF-212 | Not a PMPM Enrollment - Determined via price overrides | Error | FAILED |
| Product Resource Id | DHF-213 | Invalid Product - product is Non-DHF | Error | FAILED |
| standardBillingType | DHF-214 | Invalid Product - Not a PMPM Product determined via default pricing | Error | FAILED |
| Product | DHF-215 | Invalid Product - Both Standard attributes and Overridden attributes are null | Error | FAILED |
| Header-DELETE Operation | DHF-216 | Invalid Header - Delete operation is not allowed | Error | FAILED |
| Client Hierarchy | DHF-217 | Invalid Enrollment - All hierarchy elements are null | Error | FAILED |
| Enrollment Expiration Date | DHF-218 | Missing or Null Expiration Date Received | Warning | Safe Proceed |
| standardBillingType | DHF-219 | Empty or null standardBillingType is received in the client enrollment overrides | Error | FAILED |
| standardClientFee | DHF-220 | Empty or null standardClientFee is received in the client enrollment overrides | Error | FAILED |

-continued

| Field | Error Code | Error Message | Error Type | Severity |
|---|---|---|---|---|
| standardFeeCode | DHF-221 | Empty or null standardFeeCode is received in the client enrollment overrides | Error | FAILED |

When an enrollment is received, the field level validations are performed by the billing facilitator module 1932 and a list of errors is captured. Enrollments with below errors are inserted by the billing facilitator module 1932 in the dhfcbe_client_billing_error table with no further process from the billing facilitator module 1932.

null or missing payload
null or missing afterData
null or missing Product
DELETE operation in header An Enrollment Resource Id may be unique for an enrollment. When a new enrollment (mapped to DHF product and standardBillingType is PMPM) is validated by the billing facilitator module 1932 and no errors were captured against it, the billing facilitator module 1932 saves the enrollment in a dhfce_client_enrollment table. The same enrollment would also be maintained in a dhfeh_enrollment_history table.

When a change enrollment is received on the same enrollment resource Id and if no errors were captured against it, the billing facilitator module 1932 updates that enrollment in the dhfce_client_enrollment table. If any validations failed on the existing enrollment (e.g., invalid enrollment or expirations dates or non-group level hierarchy) is found on the change enrollment, then the billing facilitator module 1932 will make no impact on the existing enrollment. But, the relevant errors and history would be maintained by the billing facilitator module 1932 for such enrollment.

When a change enrollment is received on the same enrollment resource Id and if validations failed due to one or more of the below reasons, then the billing facilitator module 1932 deletes the enrollment from dhfce_client_enrollment table. Also the corresponding errors and history would be maintained by the billing facilitator module 1932 in the dhfcbe_client_billing_error and dhfeh_enrollment_history tables.

Overrides on standardBillingType as Non-PMPM
No overrides and defaulted to standardBillingType as Non-PMPM.
Changed product Resource Id is non-DHF or non-PMPM
For PMPM billing, enrollments' product level standard attributes namely standardBillingType, standardClientFee, and standardFeeCode may be prioritized by the billing facilitator module 1932 over default standard attributes (e.g., defined in clinical product data). The below acronyms are used for Override Level:
BT: Billing Type
CFC: Client Fee Code
CFDA: Client Fee Dollar Amount

| Change Enrollment - options | Default standard pricing attributes | Override Flag | Override Level | Enrollments' final pricing | Comments |
|---|---|---|---|---|---|
| "options": [ {"name": "standardBillingType", "value": "PMPM"}, {"name": "standardClientFee", "value": "19.00" {"name": "standardFeeCode", "value": "D211"}] | standardBillingType=PPM standardClientFee=10.00; standardFeeCode=D001 | True | All | standardBillingType=PPM standardClientFee=19.00; standardFee Code=D211 | Default attributes are not conside red in this case |
| ,"options": [ {"name": "standardBillingType","value": "PMPM"}] | standardBillingType=PPPM standardClientFee=10.00; standardFeeCode=D001 | True | BT | standardBillingType=PMPM standardClientFee=10.00; standardFeeCode=D001 | |
| ,"options": [ {"name": "standardBillingType","value": "PMPM"}] | standardBillingType=PPPM | True | BT | standardBillingType=PMPM standardClientFee=0.00; standardFeeCode="" | When no default clientFee and feecode are not available |
| "options": [ {"name": "standardBillingType","value": "PMPM"}, {"name": "standardClientFee", "value": "19.00"}] | standardBillingType=PPPM standardClientFee=10.00; standardFeeCode=D001 | True | BT;CF DA | standardBillingType=PMPM standardClientFee=19.00; standardFeeCode=D001 | |

| Change Enrollment - options | Default standard pricing attributes | Override Flag | Override Level | Enrollments' final pricing | Comments |
|---|---|---|---|---|---|
| "options": [ {"name": "standardClientFee", "value": "19.00"}, {"name": "standardFeeCode", "value": "D211"}] | standardBillingType=PMPM standardClientFee=10.00; standardFeeCode=D001 | True | CFDA; CFC | standardBillingType=PMPM standardClientFee=19.00; standardFeeCode=D211 | |
| "options": [ {"name": "standardClientFee", "value": "19.00"}, {"name": "standardFeeCode", "value": "D211"}] | standardBillingType=PMPM standardClientFee=10.00; standardFeeCode=D001 | N/A | N/A | N/A | |
| No Overrides (No options/ null options/ empty options) | standardBillingType=PPPM standardClientFee=10.00; standardFeeCode=D001 | false | NONE | N/A | |
| No Overrides | standardBillingType=PMPM standardClientFee=10.00; standardFeeCode=D001 | false | NONE | standardBillingType=PMPM standardClientFee=10.00; standardFeeCode=D001 | |
| No Overrides | No Defaults | false | NONE | N/A | |

The billing facilitator module 1932 selectively calls a clinical product API. A call to Clinical product entity may be made by the billing facilitator module 1932 to fetch the DHF clinical products as and when the loaded cache is expired or on start up. A uniform resource locator (URL) for the product entity API is as follows. https://api-qa.XXX.io/v2/products/clinical?optionName=DHF&option Value=true. Fetched data is cached by the billing facilitator module 1932 in memory cache and is also inserted/updated in a dhfp_product table.

An eligibility counter module 1936 may be a multi-instance application built using the Java 8® programming language and the Spring® software development framework. The eligibility counter module 1936 establishes connectivity with the Postgres database and a server 1940 (e.g., a Linux server) using SFTP. The eligibility counter module 1936 gathers eligible enrollments from the dhfce_client_enrollment table and fetches member population counts using Carrier, Contract, and Group combination fields from eligibility files and calculates the billable amount per Carrier, Contract, Group. The eligibility counter module 1936 runs, for example, on the 1st of each month using a Cron expression.

The eligibility counter module 1936 starts by querying the dhfce_client_enrollment table for all eligible enrollments. The eligibility counter module 1936 also generates a date of service which happens to be the 1st of the previous month, because it is always generating billing data for the past month's enrollments. The eligibility counter module 1936 determines eligibility based on the following conditions:

- Each enrollment is eligible as of the Date of Service (DOS)—this is done by ensuring that the DOS is in between effective and expiry date of the enrollment.
- Each enrollment is enrolled into an active DHF product—this is done by ensuring that the DOS is in between effective and expiry date of the product.
- Each enrollment is indeed at the group level—this is done by ensuring that the hierarchy contains Carrier, Contract and Group.
- The product of the enrollment is DHF and PMPM at the time of the job run Once the enrollments are queried, the eligibility counter module 1936 makes a map using Carrier, Contract, Group (hierarchy) as the key and the enrollment as the value. Using the hierarchy, the eligibility counter module 1936 queries eligibility files that are sitting in the server 1940 and extracts the counts from there.

The eligibility files are generated by one of the servers 1940 that sends the files to the prescribed location in the Linux Server. Since the eligibility data may be large, the one of the servers 1940 may split the data into multiple (e.g., 6) files with a predetermined naming convention-<env>.eligent_<file-no>_<yyyyMMdd>_<hhmmss>.txt (prod.eligcnt_5_20210425_152009.txt). The file-no. in the file name is used by the eligibility counter module 1936 to determine which instance of the eligibility counter module 1936 will pick up the file. As there are the same number of instances as files (e.g., 6) running, each with an instance Id starting from 0 to 5, the eligibility counter module 1936 uses this instance to create an exclusive read connection with the file of the same file no. This helps speed up the reads and helps keep memory usage at a minimum.

Once each instance is done reading the files, the eligibility counter module 1936 copies the member counts over and a final calculation of unit amount is done per hierarchy. Once this processing is complete, all records that have a unit amount of greater than $0.00 are written by the eligibility counter module 1936 to the dhfcb_client_billing table with a status of "ReadyForBilling". This is the cue for collation module 1924 to pick up these records for billing by the billing module 1928. The collation module 1924 runs after the billing facilitator module 1932 completes its process.

The eligibility counter module 1936 keeps track of each run in dhfbn_billing_notify table. The eligibility counter module 1936 generates a JobID with start and end dates and also sends out an email notification when it's done processing. If there are any errors with the job, it keeps a track of them in the dhfcbe_client_billing_error table.

The collation module collates data from both PMPM and per participant per month (PPPM) flows and sends them out to the billing module 1928.

The MFT gateway module 1904 may be a React.js based front-end application that provides reporting capabilities to product owners and vendors regarding the transactions that are submitted. This MFT gateway module 1904 may be powered by two backend apps, which may be named DHF-Portal-API and DHF-Portal-Auth. The DHF-Portal-API app provides data by exposing HTTP APIs. It queries the database to fetch the transaction data. The DHF-Portal-Auth application provides user registration and login capabilities.

The dhfmtc_mem_tran_life_cycle table stores all the vendor transactions that are written to it by the adjudication module 1920 and is also utilized for read and/or update operations by collation module 1924, the report module 1912, the remittance module 2004, and DHF-Portal-API apps. Following are some of the constraints and indexes applied on the table to aid in application querying. Each transaction that is ingested by the transaction processing module 1808—whether it may be transaction from files or transactions from HTTP API—has a universally unique identifier (UUID) assigned to it, which may be called dhfTransactionId. Even duplicate transactions received will have a unique transaction id assigned. To ensure that the same transaction will not be entered twice, a unique constraint on dhfTransactionId may be used. If during a high volume period, a transaction is somehow inserted twice in database, the database will throw a unique constraint violation exception and the MFT gateway module 1904 will catch it and raise an alert.

Before the adjudication module 1920 inserts a record in the lifecycle table, the adjudication module 1920 executes a read on the table to ensure there aren't any duplicates. This read operation is performed quickly. A unique transaction is defined by memberId, group, personCode, upc, DOS, and paymentType, therefore an index is created on a combination of these columns.

The collation module 1924 queries transactions from the lifecycle table to generate a billing file for the billing module 1928 using the billing status column. When the value of Billing Status is "ReadyForBilling" will the collation module 1924 pick up the transaction. Due to a high volume of rejects and non-billable transactions, multiple values may be used for billing status. This index helps speed up querying and quickly get the desired set of transactions.

The report module 1912 reads transactions for reporting based on file_id—these are transactions that were submitted by vendors using files. Therefore all such transactions can be identified by their file_id, which includes metadata about the transaction stored against it. When the report module 1912's job triggers, the report module 1912 fetches all file_Ids from file_meta table which were received in the last 24 hours, and the report module 1912 begins generating summary reports against it. At this moment the report module 1912 fetches all transactions by the file_ids therefore an index has been created on it to speed up querying.

When the remittance module 2004's job triigers, such as on the 1st of a month, the remittance module 2004 queries all transactions for a prior month against each vendor where the remittance status is "ReadyForRemittance". The query generates remittance invoice on behalf of the vendors. To speed up this query, an index has been created on vendorId, insertTimestamp, and remittanceStatus.

The Member Error Summary table is written to by the adjudication module 1920 when a transaction has error codes assigned to it. Each transaction can have multiple error codes, therefore these error codes are stored against a transaction in this separate table. The dhfTransactionId is the common column in Life Cycle and Member Error Summary. The index is created on dhfTransactionId because when report module 1912 or MFT gateway module 1904 query the Life Cycle table, they tjoin that data with error codes data from the Member Error Summary table. Having an index here on dhfTransactionId speeds up the joins.

The report module 1912, the adjudication module 1920, and the MFT gateway module 1904 all map the internal DHF error codes to their NCPDP counterpart while reporting and responding back to vendors. The common column between NCPDP Error Master and Member Error Summary tables is dhf_error_code. To speed up the joins and index is used on dhf_error_code. The listener module 1908 writes file metadata information to this table/index when it intercepts a vendor file. The file name column here is used for querying for duplicates, therefore an index may be used on this column to speed up querying.

The listener module 1908 may have a remote file delete feature and a local file delete feature. Both of these delete features may be triggered when the listener module 1908 verifies that an entry has been made against the file in Vendor File Storage table. This is the table where the file is stored in binary format. To ensure that the file was indeed stored, the listener module 1908 uses the complete_vendor_file_name to query the table, therefore an index has been placed on this column to speed up querying. In various implementations, data definition language (DDL) schema scripts may be executed by the transaction processing module 1908.

FIG. 23 is a flowchart depicting an example method of adjudicating transactions from vendors. Loops of the example of FIG. 23 may be started each predetermined period, such as every 1 hour. Control begins with 2304 where the MFT gateway module 1904 determines whether a file including transactions has been received from a vendor. If 2304 is true, control continues with 2308. If 2304 is false, control may end.

At 2308, the MFT gateway module 1904 stores the file in the inbound folder that the listener module 1908 monitors. At 2312, the listener module 1908 determines whether any new files are in the monitored folder. If so, the listener module 1908 validates the transactions in the file at 2312. At 2316, the listener module 1908 converts the transactions into objects.

At 2320, the listener module 1908 transmits the objects for the transactions, respectively, to the Kafka topic module 1916. At 2324, the Kafka topic module 1916 generates Kafka topics for the transactions based on the objects, respectively. At 2328, the adjudication module 1920 adjudicates the transactions and updates the tables, as described above. At 2332, the report module 1912 responds to the vendor that submitted the file of transactions using data from the tables, as discussed above. While the example of FIG. 23 is shown as ending, loops of FIG. 23 may be started each predetermined period, as discussed above.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A digital health solution system, comprising:
a virtual pharmacy comprising one or more processors configured to operate a web portal for user devices via one of a set of networks, the web portal serving as a marketplace for products and services available from vendors for consumption by users;
a transaction processing module configured to:
receive, via one of the set of networks, and a first application programming interface (API), a batch of transactions from a first vendor regarding a first set of products and services, wherein:
the first set of products and services are consumed by users via the virtual pharmacy for payment to the first vendor, and
each transaction of the batch of transactions has a first data structure;
receive, via one of the set of networks, and a second API, a single transaction from a second vendor regarding payment to the second vendor for a second set of products and services, wherein:
the second set of products and services are consumed by a single user via the virtual pharmacy, and
the single transaction has a second data structure that is different than the first data structure;
perform an adjudication of the batch of transactions and the single transaction using adjudication rules stored in memory, wherein the adjudication includes transmitting a notification regarding a subset of the first set of products and services and the second set of products and services;
determine whether the adjudication has been successful;
in response to a determination that the adjudication has not been successful, recall the notification;
bill a first entity for use of the first set of products and services associated with the users when the batch of transactions passes adjudication;
deny a respective transaction of the batch of transactions when the respective transaction does not satisfy one or more of the adjudication rules;
bill a second entity for use of the second set of products and services associated with the single user when the single transaction passes adjudication;
deny the single transaction when the single transaction does not satisfy one or more of the adjudication rules;
transmit a first response regarding the adjudication of the batch of transactions to the first vendor, wherein transmitting the first response includes:
before the adjudication of the batch of transactions, determining whether the batch of transactions includes one or more errors, and
in response to a determination that the batch of transactions includes one or more errors, transmitting a standard reject response; and
transmit a second response regarding the adjudication of the single transaction to the second vendor; and
a prescription fulfillment system including one or more processors configured to automatically control an automated dispensing device by:
identifying a prescription drug associated with the first set of products and services, and
fulfilling the prescription drug without operator intervention by:
controlling movement of a set of containers relative to the automated dispensing device, and
automatically dispensing, via the automated dispensing device, the prescription drug into a container of the set of containers.

2. The digital health solution system of claim 1 wherein the first data structure includes:
a member transaction identifier;
a header portion; and
a transaction portion.

3. The digital health solution system of claim 2 wherein the header portion includes:
a date;
a time;
a vendor file identifier;
a first vendor file name;
a second vendor file identifier;
an identifier of the first vendor; and
a name of the first vendor.

4. The digital health solution system of claim 2 wherein the transaction portion includes:
a carrier identifier;
an eligibility group;
a payment type;
a unit count;
a member identifier;
a person number;
a date of birth;
an activation code;
a universal pricing code (UPC);
a UPC qualifier;
a first name;
a last name;
a contract;
a claim identifier;
a date of service;
a record number;
a vendor member timestamp; and
a vendor patient identifier.

5. The digital health solution system of claim 1 wherein the second data structure includes:
a claim identifier;
a timestamp;
a vendor identifier;
a member portion; and
an order portion.

6. The digital health solution system of claim 5 wherein the member portion includes:
an identifier of a member;
a first name of the member;
a last name of the member;
a carrier identifier;
an eligibility group;
a date of birth of the member;
a person number of the member;

a contract of the member; and
a patient identifier of the member.

7. The digital health solution system of claim 5 wherein the order portion includes:
a universal pricing code (UPC);
a UPC qualifier;
a payment type for the single transaction;
an activation code for the single transaction;
a unit count for the single transaction; and
a date of service of the single transaction.

8. The digital health solution system of claim 1 wherein the first API is a secure shell (SSH) file transfer protocol (SFTP) ingestion point configured to receive the batch of transactions using SFTP.

9. The digital health solution system of claim 1 wherein the second API is a representational state transfer (REST) API.

10. A digital health solution system, comprising:
a virtual pharmacy comprising one or more processors configured to operate a web portal for user devices via one of a set of networks, the web portal serving as a marketplace for a set of products and services available from vendors for consumption by users;
a transaction processing module configured to:
  receive, via one of the set of networks, a transaction from a vendor regarding one or more products and services of the set of products and services consumed by one or more users via the virtual pharmacy for payment to the vendor;
  perform an adjudication of the transaction using adjudication rules stored in memory, wherein the adjudication includes transmitting a notification regarding the one or more products and services;
  determine whether the adjudication has been successful;
  in response to a determination that the adjudication has not been successful, recall the notification;
  bill an entity for use of the one or more products and services associated with the one or more users when the transaction passes adjudication; and
  transmit, via one of the set of networks, a response regarding the transaction to the vendor, wherein transmitting the response includes:
    before the adjudication of the transaction, determining whether the transaction includes one or more errors, and
    in response to a determination that the transaction includes one or more errors, transmitting a standard reject response; and
a prescription fulfillment system including one or more processors configured to automatically control an automated dispensing device by:
  identifying a prescription drug associated with the one or more products and services, and
  fulfilling the prescription drug without operator intervention by:
    controlling movement of a set of containers relative to the automated dispensing device, and
    automatically dispensing, via the automated dispensing device, the prescription drug into a container of the set of containers.

11. The digital health solution system of claim 10 wherein the transaction processing module is configured to receive the transaction in a file including multiple transactions received from the vendor via a communication received using a secure shell (SSH) file transfer protocol (SFTP).

12. The digital health solution system of claim 11 wherein the transaction processing module is configured to reject the transaction if a name of the file does not include a name of the vendor, an ID of the vendor, a present year, a present month, a present date, a present hour, a present minute, and a present second.

13. The digital health solution system of claim 10 wherein the transaction processing module is configured to:
receive the transaction via an application programming interface (API); and
transmit the response within less than 10 milliseconds of receiving the transaction.

14. The digital health solution system of claim 13 wherein the transaction processing module is configured to:
receive from the vendor, via one of the set of networks, a request including a transaction identifier of the transaction using a second API;
determine a status of the adjudication of the transaction using the transaction identifier; and
transmit, via one of the set of networks, the status of the transaction to the vendor.

15. The digital health solution system of claim 10 wherein the transaction processing module is configured to adjudicate multiple transactions in parallel.

16. A digital health solution transaction management method comprising, by one or more processors:
operating, via one of a set of networks, a web portal for a virtual pharmacy for user devices, the web portal serving as a marketplace for a set of products and services available from vendors for consumption by users;
receiving, via one of the set of networks, a transaction from a vendor regarding one or more products and services of the set of products and services consumed by one or more users via the virtual pharmacy for payment to the vendor;
perform an adjudication of the transaction using adjudication rules stored in memory, wherein the adjudication includes transmitting a notification regarding the one or more products and services;
determining whether the adjudication has been successful;
in response to a determination that the adjudication has not been successful, recalling the notification;
billing an entity for use of the one or more products and services associated with the one or more users when the transaction passes adjudication;
transmitting, via one of the set of networks, a response regarding the transaction to the vendor, wherein transmitting the response includes:
  before the adjudication of the transaction, determining whether the transaction includes one or more errors, and
  in response to a determination that the transaction includes one or more errors, transmitting a standard reject response;
identifying a prescription drug associated with the one or more products and services, and
fulfilling the prescription drug without operator intervention by:
  controlling movement of a set of containers, and
  automatically dispensing the prescription drug into a container of the set of containers.

17. The digital health solution transaction management method of claim 16 wherein receiving the transaction includes receiving the transaction in a file including multiple transactions received from the vendor via a communication received using a secure shell (SSH) file transfer protocol (SFTP).

18. The digital health solution transaction management method of claim 17 further comprising rejecting the transaction when a name of the file does not include a name of the vendor, an ID of the vendor, a present year, a present month, a present date, a present hour, a present minute, and a present second.

19. The digital health solution transaction management method of claim 16 wherein:
   the receiving the transaction includes receiving the transaction via an application programming interface (API); and
   the transmitting includes transmitting the response within less than 10 milliseconds of receiving the transaction.

20. The digital health solution transaction management method of claim 19 further comprising:
   receiving from the vendor, via one of the set of networks, a request including a transaction identifier of the transaction using a second API;
   determining a status of the adjudication of the transaction using the transaction identifier; and
   transmitting, via one of the set of networks, the status of the transaction to the vendor.

21. The digital health solution transaction management method of claim 16 further comprising adjudicating multiple transactions in parallel.

* * * * *